US009199965B2

(12) United States Patent
Kim et al.

(10) Patent No.: US 9,199,965 B2
(45) Date of Patent: *Dec. 1, 2015

(54) BENZOIMIDAZOLE DERIVATIVES AND PHARMACEUTICAL COMPOSITION COMPRISING THE SAME

(75) Inventors: Ji Duck Kim, Yongin-si (KR); Hong Chul Yoon, Seongnam-si (KR); In Woo Kim, Seoul (KR); Hyae Jung Hyun, Yongin-si (KR)

(73) Assignee: Daewoong Co., Ltd., Seongnam-si (KR)

( * ) Notice: Subject to any disclaimer, the term of this patent is extended or adjusted under 35 U.S.C. 154(b) by 284 days.

This patent is subject to a terminal disclaimer.

(21) Appl. No.: 11/815,009

(22) PCT Filed: Jan. 27, 2006

(86) PCT No.: PCT/KR2006/000324
§ 371 (c)(1),
(2), (4) Date: Jul. 27, 2007

(87) PCT Pub. No.: WO2006/080821
PCT Pub. Date: Aug. 3, 2006

(65) Prior Publication Data
US 2009/0018124 A1 Jan. 15, 2009

(30) Foreign Application Priority Data

Jan. 28, 2005 (KR) .................... 10-2005-0008183
Oct. 18, 2005 (KR) .................... 10-2005-0098349

(51) Int. Cl.
*C07D 401/10* (2006.01)
*C07D 417/14* (2006.01)
*C07D 471/04* (2006.01)
*C07D 403/04* (2006.01)
*C07D 403/14* (2006.01)

(52) U.S. Cl.
CPC ............ *C07D 401/10* (2013.01); *C07D 417/14* (2013.01); *C07D 471/04* (2013.01)

(58) Field of Classification Search
CPC .. C07D 401/10; C07D 417/14; C07D 471/04; C07D 403/04; C07D 403/14
See application file for complete search history.

(56) References Cited

U.S. PATENT DOCUMENTS

| | | | | |
|---|---|---|---|---|
| 2,488,094 | A | * 11/1949 | Ackermann et al. | 548/305.7 |
| 3,317,382 | A | * 5/1967 | Brunner et al. | 514/159 |
| 3,641,051 | A | 2/1972 | Frischkorn et al. | |
| 4,263,441 | A | 4/1981 | Pintschovius et al. | |
| 4,603,139 | A | * 7/1986 | King | 514/337 |
| 5,942,532 | A | * 8/1999 | Ohemeng et al. | 514/396 |
| 6,696,437 | B1 | 2/2004 | Lubisch et al. | |
| 7,622,479 | B2 | 11/2009 | Oda et al. | |
| 2003/0069292 | A1* | 4/2003 | Hogenkamp et al. | 514/365 |
| 2003/0100582 | A1 | 5/2003 | Sircar et al. | |
| 2005/0101647 | A1* | 5/2005 | Oda et al. | 514/367 |
| 2005/0148646 | A1* | 7/2005 | Boykin et al. | 514/394 |
| 2006/0160799 | A1* | 7/2006 | Alekshun et al. | 514/233.5 |
| 2007/0112020 | A1 | 5/2007 | Vanotti | |

FOREIGN PATENT DOCUMENTS

| | | | |
|---|---|---|---|
| CN | 1506355 | | 6/2004 |
| DE | CA 2349227 | * | 5/2000 |
| EP | 0 012 866 A1 | | 11/1979 |
| EP | WO0026192 A1 | | 5/2000 |
| FR | 1 488 286 A | | 7/1967 |
| GB | 2164648 A | | 3/1986 |
| JP | 05-230674 | | 9/1993 |
| JP | 06-299374 | | 10/1994 |
| JP | WO 03/045929 | * | 5/2003 |
| JP | 2004-203804 | | 7/2004 |
| KR | 10-2004-0034804 | | 4/2004 |
| WO | WO 88/02367 | | 4/1988 |
| WO | WO 98/20007 | | 5/1998 |
| WO | WO 99/07703 | | 2/1999 |
| WO | WO 99/11627 | | 3/1999 |
| WO | WO 00/57877 | | 10/2000 |
| WO | WO 02/08221 | | 1/2002 |
| WO | WO 02/16317 | | 2/2002 |
| WO | WO 02/072536 | | 9/2002 |
| WO | WO 02/076438 | * | 10/2002 |
| WO | WO 02/076946 | | 10/2002 |
| WO | WO 02/090326 | | 11/2002 |
| WO | WO 03/014064 | | 2/2003 |
| WO | WO 03/022809 | | 3/2003 |

(Continued)

OTHER PUBLICATIONS

Jordan, V. C. Nature Reviews: Drug Discovery, 2, 2003, pp. 205-213.*
Jordan, V. C. Nature Reviews: Drug Discovery, 2, 2003, p. 205-213.*
Dörwald, F. Zaragoza. Side Reactions in Organic Synthesis: A Guide to Successful Synthesis Design, Weinheim: Wiley-VCH Verlag GmbH & Co. KGaA, 2005, Preface.*
Alcalde et al. (Eur. J. Med. Chem. (1990), 25 (4); p. 309-319).*
Yu et al. (Heterocycles (2003), 60 (6); p. 1457-1460.*
Gangjee et al. (J. Med. Chem. (1997), 40; p. 3032-3039.*

(Continued)

*Primary Examiner* — Valerie Rodriguez-Garcia
(74) *Attorney, Agent, or Firm* — Seed IP Law Group PLLC

(57) ABSTRACT

Disclosed herein are novel benzoimidazole derivatives functioning as antagonists to vanilloid receptor-1, and a pharmaceutical composition comprising the same. They are useful in preventing or treating pain, acute pain, chronic pain, neuropathic pain, postoperative pain, migraines, arthralgia, neuropathy, nerve injury, diabetic neuropathy, neurological illness, neurodermatitis, strokes, bladder hypersensitivity, irritable bowel syndrome, respiratory disorders such as asthma, chronic obstructive pulmonary disease, etc., burns, psoriasis, itching, vomiting, irritation of the skin, eyes, and mucous membranes, gastric-duodenal ulcers, inflammatory intestinal diseases, and inflammatory diseases.

10 Claims, No Drawings

(56) References Cited

FOREIGN PATENT DOCUMENTS

| WO | WO 03/029199 | | 4/2003 |
|---|---|---|---|
| WO | WO 03/032984 | * | 4/2003 |
| WO | WO 03/032984 A1 | | 4/2003 |
| WO | WO 03/055484 | | 7/2003 |
| WO | WO 03/057696 A1 | | 7/2003 |
| WO | WO 03/062209 | | 7/2003 |
| WO | WO 03/066673 | | 8/2003 |
| WO | WO 03/068749 | | 8/2003 |
| WO | WO 03/070247 | | 8/2003 |
| WO | WO 03/080578 | | 10/2003 |
| WO | WO 03/097586 | | 11/2003 |
| WO | WO 03/099284 | | 12/2003 |
| WO | WO 2004/002983 | | 1/2004 |
| WO | WO 2004/011439 | | 2/2004 |
| WO | WO 2004/014871 | | 2/2004 |
| WO | WO 2004/016611 A1 | | 2/2004 |
| WO | WO 2004/024897 A2 | | 3/2004 |
| WO | WO 2004/033435 | | 4/2004 |
| WO | WO 2004/035549 | | 4/2004 |
| WO | WO 2004/055003 | | 7/2004 |
| WO | WO 2004/055004 | | 7/2004 |
| WO | WO 2004/093873 A1 | | 11/2004 |
| WO | WO 2005/002503 | * | 1/2005 |

OTHER PUBLICATIONS

Cymerman-Craig et al. (British Journal of Experimental Pathology (1955), 36, 261-267.*
Arienti et al. (J. Med. Chem. 2005, 48, 1873-1885-published on the web on Nov. 5, 2004).*
Anderson et al. (Biochemistry (1973), 12 (10), 1895-1900).*
Plutzer et al. (Phys. Chem. Chem. Phys., 2002, 4, 4877-4882).*
Todorova et al. (Trudove na Nauchnoizsledovatelskiya Khimikofarmatsevtichen Institut, 10 (1978), p. 85-94).*
Caterina et al, "The capsaicin receptor: a heat-activated ion channel in the pain pathway," Nature 389:816-824, Oct. 23, 1997.
Buck and Burks, "The Neuropharmacology of Capsaicin; Review of Some Recent Observations" Pharmacological Reviews 38(3):179-226.
Ito et al. "Pharmacological Studies of a new Non-steroidal Antiinflammatory Drug: 2-(5-Ethylpyridin-2-yl)benzimidazole (KB-1043)," Drug Res. 32(1), Nr. 1:49-55, 1982.
Mezey et al., "Distribution of mRNA for vanilloid receptor subtype 1 (VR1) and VR1-like immunoreactivity, in the central nervous system of the rat human," PNAS 97(7):3655-3660, Mar. 28, 2000.
Tapolcsanyi et al., "Synthesis of some diazino-fused tricyclic systems via Suzuki cross-coupling and regioselective nitrene insertion reactions," Tetrahedron 58:10137-10143, 2002.
Yiangou et al,, "Vanilloid receptor 1 immunoreactivity in inflamed human bowel," The Lancet 357:1338-1339, Apr. 28, 2001.
Szallasi and Appendino, "Vanilloid Receptor TRPV1 Antagonists as the Next Generation of Painkillers. Are We Putting the Cart before the Horse?," J. of Medicinal Chemistry, 47(11):2717-2723, May 20, 2004.

Birder et al., "Vanilloid receptor expression suggests a sensory role for urinary badder epithelial cells," PNAS, 98(23):13396-13401, Nov. 6, 2001.
Premkumar and Ahern, "Induction of vanilloid receptor channel activity by protein kinase C," Nature 408:985-990, Dec. 2000.
Lu et al., "Microwave Irradiation Synthesis of 2-Substituted Benzimidazoles using PPA as a Catalyst under Solvent-Free Conditions," Synthetic Communications 32(24):3703-3709, 2002.
Nozawa et al., "Distribution and characterization of vanilloid receptors in the rat stomach," Neuroscience Letters 309:33-36, 2001.
Ries et al., "6-Substituted Benzimidazoles as New Nonpeptide Angiotensin II Receptor Antagonists: Synthesis, Biological Activity, and Structure-Activity Relationships," J. Med. Chem. 36:4040-4051, 1993.
Tominaga et al., "The Cloned Capsaicin Receptor Integrates Multiple Pain-Producing Stimuli," Neuron, 21;531-543, Sep. 1998.
Caterina et al,, "Impaired Nociception and Pain Sensation in Mice Lacking Capsaicin Receptor," Science 288:306-313, Apr. 14, 2000.
Sharma et al., "Aromatic Analogs of Arcaine Inhibit MK-801 Binding to the NMDA Receptor," Bioorganic & Medicinal Chemistry Letters 8:3459-3464, 1998.
Perry R J: Journal of Organic Chemistry, American Chemical Society, Easton.; vol. 58, Jan. 1, 1993, pp. 7016-7021.
Pla-Dalmau A: Journal of Organic Chemistry, American Chemical Society, Easton.; vol. 60, No. 17, Sep. 25, 1995, p. 5468-5473.
Krebs et al.: Tetrahedron Letters, vol. 42, 2001, pp. 6753-6757.
Bauer, Cymerman: Journal of the Chemical Society, 1950, pp. 2078-2080.
Ito et al., "Pharmacological Studies of a New Non-Steroidal Antiinflammatory Drug: 2-(5-Ethylpyridin-2-yl) Benzimidazole (KB-1043)," Arzneim.—Forsch./Drug Res., 32(1):49-55, 1982.
Denny et al., "Potential Antitumor Agents. 59. Structure-Activity Relationships for 2-Phenylbenzidazole-4-carboxamides, a New Class of "Minimal" DNA-Intercalating Agents which may not Act Via Topoisomerase II," J. Med. Chem, 33:814-819, 1990.
Frischkorn et al., "Naphthylenedi(heteroarenes), III1).—Synthesis and Spectroscopic Properties of 2,2'—Naphthylenedibenzazoles," Liebigs Ann. Chem. 1129-1136, 1984.
Vodenicharov et al., "Spectral Behaviour of 2-Substituted Benzimidazole Derivatives of Biphenyl and Biphenylether," Doklady Bolgarskoi Akademii Nauk., 31(4):441-444, 1978.
Roberston et al., "Structure-Activity Relationships of Arylimidazopyridine Cardiotonics: Discovery and Inotropic Activity of 2-[2-Methoxy-4-(methylsulfinyl) phenyl]-1H-imidazo[4,5-c] pyridine1," American Chemical Society, 28(6):717-727, 1985.
Kane, et al., "Polymorphism in 2,2'-Diphenyl-5,5'-bibenzimidazole." J Heterocyclic Chem, 7(4):943-946, 1970.
Blettner, et al., "Parallel Synthesis of Polyethylene Glycol Supported Biaryl Benzimidazoles and Imidazopyridines," Synlett, 3:307-310, 1999.
Yu, et al., "Microwave-Assisted Synthesis of Aryl and Heteroaryl Derivatives of Benzimidazole," Heterocycles, 60(6)1457-1460, 2003.

* cited by examiner

BENZOIMIDAZOLE DERIVATIVES AND PHARMACEUTICAL COMPOSITION COMPRISING THE SAME

TECHNICAL FIELD

The present invention relates, in general, to novel benzoimidazole derivatives and, more particularly, to novel benzoimidazole derivatives functioning as antagonists to a vanilloid receptor (capsaicin receptor; Transient Receptor Potential Channel, Vanilloid subfamily member 1; TRPV-1; Vanilloid receptor-1; VR-1). Also, the present invention is concerned with a method for preparing the benzoimidazole derivatives, uses of the derivatives and pharmaceutical compositions comprising the derivatives as active ingredients.

BACKGROUND ART

The vanilloid receptor, the receptor for capsaicin (trans-8-methyl-N-vanillyl-6-nonenamide), has long been assumed to exist. Finally, it was cloned in 1997 and called vanilloid receptor subtype 1 (hereinafter referred to as "VR-1") by Caterina et al. (Caterina et al., Nature, 1997, 389, 816). Located on small unmyelinated nerve fibers (C-fibers) and myelinated nerve fibers (A-fibers), VR-1 is known as an ion channel which plays an important role in sensitizing pain stimuli by introducing the strong influx of cations such as calcium and sodium ions into the nerve endings upon activation in response to external or internal stimuli. External stimuli capable of activating VR-1 are reported to include heat and acids as well as vanilloid compounds (Tominaga et al., Neuron, 1998, 21, 531). As internal stimuli to VR-1, there are leukotriene metabolites such as 12-hydroperoxyeicosa tetraenoic acid (12-HPETE) (Hwang at al., PNAS, 2000, 97, 3655), and arachidonic acid derivatives such as anandamide (Premkumar et al., Nature, 2000, 408, 985).

On the basis of these physiological activities, VR1 has attracted intensive attention as an integral controller playing a pivotal role in transferring various external injurable stimuli into nerve cells. According to a report, VR1 knock-out mice responded like normal mice to general stimuli, but showed greatly reduced pain response to heat or thermal hyperalgesia, which reflects the importance of VR1 against noxious stimuli (Caterina et al., Science, 2000, 288, 306).

VR1 is concentratively expressed in primary sensory neurons (Caterina et al., Nature, 1997, 389, 816), which are responsible for controlling functions of internal organs such as the skin, the bones, the bladder, the gastrointestinal tract, the lungs, and so on. In addition, being distributed in other neurons on the central nervous system, the kidneys, the stomach, and T-cells (Nozawa et al., Neuroscience Letter, 2001, 309, 33; Yiangou et al., Lancet (North America Edition), 2001, 357, 1338; Birder et al., PNAS, 2001, 98, 13396) and throughout the entire body, VR1 is inferred to play an important role in cell division and cellular signal control.

Indications found, thus far, to be associated with the control mechanism of the activity of VR1 include pain, acute pain, chronic pain, neuropathic pain, postoperative pain, migraines, arthralgia, neuropathy, nerve injury, diabetic neuropathy, neurological illness, neurodermatitis, strokes, bladder hypersensitivity, irritable bowel syndrome, respiratory disorders such as asthma, chronic obstructive pulmonary disease, etc., irritation to the skin, eyes, and mucous membranes, itching, fever, gastric-duodenal ulcer, inflammatory intestinal diseases, and urge incontinence (Korean Pat. Laid-Open Publication No. 10-2004-0034804), and an anti-obestic effect (Pharmacol. Rev., 1986, 38, 179).

Based on pharmaceutical mechanisms, both agonists and antagonists of VR1 may be used for the treatment of the above-mentioned diseases. Pain alleviating effects of VR1 agonists show the pharmaceutical mechanism based on the desensitization of capsaicin-sensitive sensory nerves. That is, VR1 agonists cause pain and irritation of sensory nerves so as to desensitize them to other noxious stimuli. Due to the induction of pain in the early stage, VR1 agonists are developed only as local analgesics. In contrast, acting through the mechanism of blocking sensory nerves from recognizing pain signals, VR1 antagonists do not cause early pain or irritation, and have been studied for use in the treatment of systemic diseases.

As compounds capable of modulating VR1 activity, agonists such as capsaicin, DA-5018, resiniferatoxin, etc. are used as pain drugs or are under clinical study (Szallasi, J. Med chem., 2004, 47, 2717), while 20 VR1 antagonists including capsazepine and iodoresiniferatoxin are under pre-clinical study (WO0208221, WO03062209, WO2004055003, WO2004055004, WO2004002983, WO0216317, WO2004035549, WO2004014871, WO03099284, WO03022809, WO02090326, WO02072536, WO03068749, WO2004033435, WO02076946, WO0095420, WO03055484, WO03014064, WO03080578, WO03097586, WO03070247, WO03029199).

Featuring superior VR-1 antagonistic effects, the novel benzoimidazole derivatives according to the present invention have chemical structures different from those of the VR1 antagonists reported thus far.

Although the compounds included within the scope of the present invention themselves are VR1 antagonists, the possibility is not excluded that modified forms thereof in an intracellular environment or metabolites thereof act as effective principles responsible for the medicinal activity.

DISCLOSURE OF THE INVENTION

Leading to the present invention, intensive and thorough research on the modulation of the activity of VR-1, conducted by the present inventors, resulted in the finding that benzoimidazole derivatives different in chemical structure from antagonists known in the art can act as excellent antagonists having potent medicinal effects (pain and inflammation relief and anti-ulcer effect) and are accepted as highly safe from measurements in animal models.

Therefore, it is an object of the present invention to provide novel benzoimidazole derivatives highly inhibitory of the activity of VR-1, or innoxious salts or solvates thereof.

It is another object of the present invention to provide a method for preparing the novel benzoimidazole derivatives, or innoxious salts or solvates thereof.

It is a further object of the present invention to provide pharmaceutical compositions inhibitory of the activity of VR-1, comprising the novel benzoimidazole derivatives, or innoxious salts or solvates thereof.

BEST MODE FOR CARRYING OUT THE INVENTION

In accordance with an aspect of the present invention, provided is a novel benzoimidazole derivative represented by the following chemical formula 1:

Chemical Formula 1

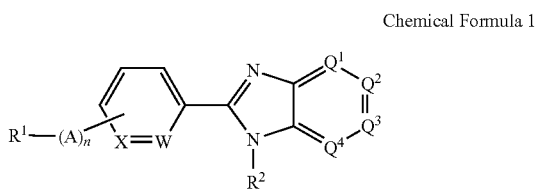

wherein

R¹ is hydrogen; a lower alkyl having 1 to 8 carbon atoms; a lower alkenyl having 2 to 6 carbon atoms; a lower alkoxy having 1 to 8 carbon atoms; a haloalkyl having 1 to 6 carbon atoms; a haloalkoxy having 1 to 6 carbon atoms; a halogen atom; a nitro; a hydroxy; a hydroxymethyl; a cyano; an amino or amide group which is mono- or di-substituted with an alkyl having 1 to 6 carbon atoms, or is non-substituted; cycloalkyl, pyridine, pyrimidine, pyrazole, pyrazine, phenyl, benzyl, imidazole, morpholine, benzodioxole, benzothiazole, benzoimidazole, indole, pyrazolone, thiophene, furan, thiazole, isothiazole, oxazole, isooxazole, triazole, oxodiazole, thiadiazole, indazole, pyrrolidine, chromonyl, piperidine, morpholmethyl, dihydropyrazole or pyrrole group which is non-substituted or substituted with one or more $R^a$; or $(CH_2)pAr$ group, Each $R^a$ is independently selected from among a lower alkyl having 1 to 8 carbon atoms; a lower alkenyl having 2 to 6 carbon atoms; a lower alkoxy having 1 to 8 carbon atoms; a haloalkyl having 1 to 6 carbon atoms; a haloalkoxy having 1 to 6 carbon atoms; a halogen atom; a nitro; a hydroxyl; a cyano; or an amino or amide or a sulfonamide group which is mono- or di-substituted with an alkyl having 1 to 6 carbon atoms or is non-substituted, A is O, NH, NHCO, CO, $CO_2$, SO, $SO_2$, or $NHSO_2$, n is an integer equal to 0 or 1, W is N or $CR^3$, X is N or $CR^4$, $R^2$ is hydrogen; a lower alkyl having 1 to 8 carbon atoms; a lower alkenyl having 2 to 6 carbon atoms; a lower alkoxy having 1 to 8 carbon atoms; a haloalkyl having 1 to 6 carbon atoms; a haloalkoxy having 1 to 6 carbon atoms; a halogen atom; nitro; hydroxy; hydroxymethyl; cyano; phosphoric acid; phosphateester; an amino or amide which is mono- or di-substituted with a lower alkyl having 1 to 6 carbon atoms; sulfanyl; sulfone; sulfoxide; sulfonamide; urea, carbamate, carbonate; ketone; ester; carboxylic acid; methoxyethanol group; cycloalkyl, pyridine, pyrimidine, pyrazole, pyrazine, phenyl, benzyl, imidazole, morpholine, benzodioxole, benzothiazole, benzoimidazole, indole, pyrazolone, thiophene, furan, thiazole, isothiazole, oxazole, isooxazole, triazole, oxodiazole, thiadiazole, indazole, pyrrolidine, chromonyl, piperidine, morpholmethyl, or dihydropyrazole group which is non-substituted or substituted with one or more $R^b$, Each $R^b$ is independently selected from among a lower alkyl having 1 to 8 carbon atoms; a lower alkenyl having 2 to 6 carbon atoms; a lower alkoxy having 1 to 8 carbon atoms; a haloalkyl having 1 to 6 carbon atoms; a haloalkoxy having 1 to 6 carbon atoms; a halogen atom; nitro; hydroxyl; cyano; sulfanyl, sulfone, sulfoxide, sulfonamide, urea, carbamate, carbonate, ketone, ester, carboxylic acid, an amino or amide which is mono- or di-substituted with a lower alkyl having 1 to 6 carbon atoms or non-substituted, $R^3$ and $R^4$ may be the same or different, and are independently hydrogen; a lower alkyl having 1 to 8 carbon atoms; a lower alkenyl having 2 to 6 carbon atoms; a lower alkoxy having 1 to 6 carbon atoms; a haloalkyl having 1 to 6 carbon atoms; a haloalkoxy having 1 to 6 carbon atoms; a halogen atom; nitro; hydroxy; cyano; sulfanyl; sulfone; sulfoxide; sulfonamide; urea; carbamate; carbonate; ketone; ester; carboxylic acid; an amino or amide group which is mono- or di-substituted with an alkyl having 1 to 3 carbon atoms or is non-substituted; or a phenyl or benzyl group which is non-substituted or substituted with $R^c$, or $R^3$ and $R^4$ form together a saturated, partially saturated, or unsaturated 5-, 6- or 7-membered heteromonocyclic ring or a saturated, partially saturated, or unsaturated 6-, 7-, 8-, 9-, 10- or 11-membered heterobicyclic ring compound which is mono-, di-, tri- or tetra-substituted with a nitrogen atom, an oxygen atom or a sulfur atom, or is non-substituted, $R^c$ is selected from among a lower alkyl having 1 to 6 carbon atoms; a lower alkenyl having 2 to 4 carbon atoms; a lower alkoxy having 1 to 6 carbon atoms; a haloalkyl having 1 to 6 carbon atoms; a haloalkoxy having 1 to 6 carbon atoms or a halogen atom, $Q_1$ is N or $CR^6$,
$Q_2$ is N or $CR^7$,
$Q_3$ is N or $CR^8$,
$Q_4$ is N or $CR^9$, Ar is selected from among

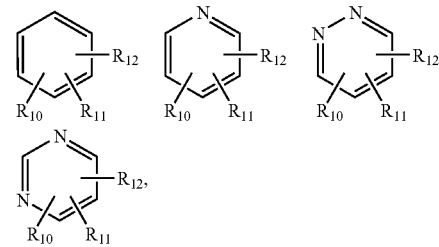

p is an integer of 0, 1, 2, 3 or 4, $R^6$, $R^7$, $R^8$, and $R^9$ may be the same or different, and are independently hydrogen; a lower alkyl having 1 to 8 carbon atoms; a lower alkenyl having 2 to 6 carbon atoms; a lower alkoxy having 1 to 8 carbon atoms; a haloalkyl having 1 to 6 carbon atoms; a haloalkoxy having 1 to 6 carbon atoms; a halogen atom; a nitro; hydroxy; hydroxymethyl; cyano; an amino or amide which is mono- or di-substituted with a lower alkyl having 1 to 6 carbon atoms or is non-substituted; sulfanyl; sulfone; sulfoxide; sulfonamide; urea; carbamate; carbonate; ketone; ester; carboxylic acid group; cycloalkyl, pyridine, pyrimidine, pyrazole, phenyl, benzyl, imidazole, morpholine, benzodioxole, benzothiazole, benzoimidazole, indole, pyrazolone, thiophene, furan, thiazole, isothiazole, oxazole, isooxazole, triazole, oxodiazole, thiadiazole, indazole, thiomorpholine, thiazolidine, oxazolidine, pyrrolidine, chromonyl, piperidine, morpholmethyl, or dihydropyrazole group which is non-substituted or substituted with one or more $R^d$, or any two of $R^6$, $R^7$, $R^8$, and $R^9$ form together a saturated, partially saturated or unsaturated 5-, 6- or 7-membered heteromonocyclic or a saturated, partially saturated or unsaturated 6-, 7-, 8-, 9-, 10- or 11-membered heterobicyclic ring compound which is mono-, di-, tri- or tetra-substituted with a nitrogen atom, an oxygen atom or a sulfur atom or is non-substituted, Each $R^d$ is independently selected from among a lower alkyl having 1 to 8 carbon atoms; a lower alkenyl having 2 to 6 carbon atoms; a lower alkoxy having 1 to 8 carbon atoms; a haloalkyl having 1 to 6 carbon atoms; a haloalkoxy having 1 to 6 carbon atoms; a halogen atom; a nitro; a hydroxyl; a cyano; an amino, amide, sulfanyl, sulfone, sulfoxide, sulfonamide, urea, carbamate, carbonate, ketone, ester, or carboxylic acid which is mono- or di-substituted with a lower alkyl having 1 to 6 carbon atoms or is non-substituted, $R^{10}$, $R^{11}$ and $R^{12}$ may be the same or different, and are independently hydrogen; a lower alkyl having 1 to 8 carbon atoms; a cycloalkyl; a lower alkenyl having 2 to 6 carbon atoms; a lower alkoxy having 1 to 6 carbon atoms; a haloalkyl having 1 to 6 carbon atoms; a halogen atom; nitro; hydroxy; hydroxymethyl; cyano; sulfanyl; sulfone; sulfoxide; sulfonamide; urea; carbamate; carbonate; ketone; an amino, amide, carboxylic acid, or carboxyester group which is mono- or di-substituted with a lower alkyl having 1 to 3 carbon atoms or is non-substituted, or any two of $R^{10}$, $R^{11}$, and $R^{12}$ form together a saturated or unsaturated heteromonocyclic or heterobicyclic ring compound.

In a preferred embodiment, the novel benzoimidazole derivative of the present invention comprise the compounds of Chemical Formula 1 and isomers thereof, concrete examples of which include:

2-[4-(3-chloropyridin-2-yl)phenyl]-6-trifluoromethyl-1H-benzoimidazole,
6-chloro-2-[4-(3-chloropyridin-2-yl)phenyl]-1H-benzoimidazole,
6-tert-butyl-2-[4-(3-chloropyridin-2-yl)phenyl]-1H-benzoimidazole,
2-[4-(3-chloropyridin-2-yl)phenyl]-6-fluoro-1H-benzoimidazole,
2-[4-(3-chloropyridin-2-yl)phenyl]-6-methoxy-1H-benzoimidazole,
4-chloro-2-[4-(3-chloropyridin-2-yl)phenyl]-6-trifluoromethyl-1H-benzoimidazole,
2-[4-(3-chloropyridin-2-yl)phenyl]-4,6-bistrifluoromethyl-1H-benzoimidazole,
2-[4-(3-chloropyridin-2-yl)phenyl]-6-trifluoromethyl-1H-imidazo[4,5-b]pyridine,
2-[4-(3-chloropyridin-2-yl)phenyl]-3H-imidazo[4,5-b]pyridine,
2-[4-(3-chloropyridin-2-yl)phenyl]-6,7-dimethyl-1H-benzoimidazole,
2-[4-(3-chloropyridin-2-yl)phenyl]-1H-benzoimidazole,
2-[4-(3-chloropyridin-2-yl)phenyl]-5,6-dichloro-1H-benzoimidazole,
6-bromo-2-(4-(3-chloropyridin-2-yl)phenyl)-1H-benzoimidazole,
4-bromo-2-(4-(3-chloropyridin-2-yl)phenyl)-6-(trifluoromethyl)-1H-benzoimidazole,
6-bromo-2-(4-(3-chloropyridin-2-yl)phenyl-1H-imidazo[4,5-b]pyridine,
4,6-dibromo-2-[4-(3-chloropyridin-2-yl)phenyl]-1H-benzoimidazole,
2-[4-(3-chloropyridin-2-yl)phenyl]-6-morpholin-4-yl-1H-benzoimidazole,
2-[4-(3-chloropyridin-2-yl)phenyl]-6-thiomorpholin-4-yl-1H-benzoimidazole,
2-[4-(3-chloropyridin-2-yl)phenyl]-4-morpholin-4-yl-6-trifluoromethyl-1H-benzoimidazole,
2-[4-(3-chloropyridin-2-yl)phenyl]-4-thiomorpholin-4-yl-6-trifluoromethyl-1H-benzoimidazole,
2-[4-(3-chloropyridin-2-yl)phenyl]-4-pyrrolidin-1-yl-6-trifluoromethyl-1H-benzoimidazole,
{2-[4-(3-chloropyridin-2-yl)phenyl]-6-trifluoromethyl-1H-benzoimidazole-4-yl}diethylamine,
2-[4-(3-chloropyridin-2-yl)phenyl]-6-morpholin-4-yl-1H-imidazo[4,5-b]pyridine,
2-[4-(3-chloropyridin-2-yl)phenyl]-6-pyrrolidin-1-yl-1H-imidazo[4,5-b]pyridine,
6-tert-butyl-2-[4-(3,5-dichloropyridin-2-yl)phenyl]-1H-benzoimidazole,
2-[4-(3,5-dichloropyridin-2-yl)phenyl]-4,6-bistrifluoromethyl-1H-benzoimidazole,
6-tert-butyl-2-[4-(3-chloro-5-trifluoromethylpyridin-2-yl)phenyl]-1H-benzoimidazole,
2-[4-(3-chloro-5-trifluoromethylpyridin-2-yl)phenyl]-4,6-bistrifluoromethyl-1H-benzoimidazole,
2-[4-(3-chloro-5-trifluoromethylpyridin-2-yl)phenyl]-5,7-bistrifluoromethyl-1H-benzoimidazole,
N-[4'-(4,6-bistrifluoromethyl-1H-benzoimidazole-2-yl)-3-fluorobiphenyl-4-yl]methanesulfonamide,
6-tert-butyl-2-[4-(3-trifluoromethylpyridin-2-yl)phenyl]-1H-benzoimidazole,
4-chloro-6-trifluoromethyl-2-[4-(3-trifluoromethylpyridin-2-yl)phenyl]-1H-benzoimidazole,
6-chloro-2-[4-(3-trifluoromethylpyridin-2-yl)phenyl]-1H-benzoimidazole,
4,6-bistrifluoromethyl-2-[4-(3-trifluoromethyl pyridin-2-yl)phenyl]-1H-benzoimidazole,
6-trifluoromethyl-2-[4-(3-trifluoromethylpyridin-2-yl)phenyl]-1H-imidazo[4,5-b]pyridine,
5,6-dichloro-2-[4-(3-trifluoromethylpyridin-2-yl)phenyl]-1H-benzoimidazole,
4-bromo-6-(trifluoromethyl)-2-(4-(3-(trifluoromethyl)pyridin-2-yl)phenyl)-1H-benzoimidazole,
6-bromo-2-(4-(3-(trifluoromethyl)pyridin-2-yl)phenyl)-1H-benzoimidazole,
6-fluoro-2-(4-(3-(trifluoromethyl)pyridin-2-yl)phenyl)-1H-benzoimidazole,
6-bromo-2-(4-(3-(trifluoromethyl)pyridin-2-yl)phenyl-1H-imidazo[4,5-b]pyridine,
4,6-dibromo-2-[4-(3-trifluoromethylpyridin-2-yl)phenyl]-1H-benzoimidazole,
6-morpholin-4-yl-2-[4-(3-trifluoromethylpyridin-2-yl)phenyl]-1H-benzoimidazole,
6-thiomorpholin-4-yl-2-[4-(3-trifluoromethylpyridin-2-yl)phenyl]-1H-benzoimidazole,
diethyl-{2-[4-(3-trifluoromethylpyridin-2-yl)phenyl]-3H-benzoimidazo-5-yl}amine,
4-morpholin-4-yl-6-trifluoromethyl-2-[4-(3-trifluoromethylpyridin-2-yl)phenyl]-1H-benzoimidazole,
4-thiomorpholin-4-yl-6-trifluoromethyl-2-[4-(3-trifluoromethylpyridin-2-yl)phenyl]-1H-benzoimidazole,
4-pyrrolidin-1-yl-6-trifluoromethyl-2-[4-(3-trifluoromethylpyridin-2-yl)phenyl]-1H-benzoimidazole,
6-tert-butyl-2-(4-pyridin-2-ylphenyl)-1H-benzoimidazole,
6-(trifluoromethyl)-2-(4-(pyridin-2-yl)phenyl)-1H-benzoimidazole,
4-chloro-6-(trifluoromethyl)-2-(4-(pyridin-2-yl)phenyl)-1H-benzoimidazole,
5,6-dichloro-2-(4-(pyridin-2-yl)phenyl)-1H-benzoimidazole,
4,6-bis(trifluoromethyl)-2-(4-(pyridin-2-yl)phenyl)-1H-benzoimidazole,
6-fluoro-2-(4-(pyridin-2-yl)phenyl)-1H-benzoimidazole,
6-bromo-2-(4-(pyridin-2-yl)phenyl)-1H-imidazo[4,5-b]pyridine,
4,6-dibromo-2-(4-pyridin-2-ylphenyl)-1H-benzoimidazole,
2-[4-(6-chloro-5-methylpyridazin-3-yl)phenyl]-4,6-bistrifluoromethyl-1H-benzoimidazole,
2-[4-(6-chloro-5-methylpyridazin-3-yl)phenyl]-5,7-bistrifluoromethyl-1H-benzoimidazole,
4-bromo-6-(trifluoromethyl)-2-(4-(4-(trifluoromethyl)pyrimidin-2-yl)phenyl)-1H-benzoimidazole, 4,6-dibromo-2-[4-(4-trifluoromethylpyrimidin-2-yl)phenyl]-1H-benzoimidazole,
6-tert-butyl-2-(4-(pyrimidin-2-yl)phenyl)-1H-benzoimidazole,
2-(4-(6-(trifluoromethyl)-1H-benzoimidazole-2-yl)phenyl)pyridin-3-carbonitrile,
2-(4-(6-(tert-butyl-1H-benzoimidazole-2-yl)phenyl)pyridin-3-carbonitrile,
6'-(4,6-dibromo-1H-benzoimidazole-2-yl)-[2,3']bipyridyl-3-carbonitrile,
2-[4-(3-chloropyrazin-2-yl)phenyl]-6-trifluoromethyl-1H-benzoimidazole,
6-tert-butyl-2-[4-(3-chloropyrazin-2-yl)phenyl]-1H-benzoimidazole,
6-bromo-2-[4-(3-chloropyrazin-2-yl)phenyl]-1H-benzoimidazole,
5,6-dichloro-2-[4-(3-chloropyrazin-2-yl)phenyl]-1H-benzoimidazole,
6-bromo-2-[4-(3-chloropyrazin-2-yl)phenyl]-1H-imidazo[4,5-b]pyridine,
6-tert-butyl-2-[4-(3-chloropyridin-2-yl)-2-fluorophenyl]-1H-benzoimidazole,
4-chloro-2-[4-(3-chloropyridin-2-yl)-2-fluorophenyl]-6-trifluoromethyl-1H-benzoimidazole,
2-[4-(3-chloropyridin-2-yl)-2-fluorophenyl]-6-methoxy-1H-benzoimidazole,
6-tert-butyl-2-[4-(3,5-dichloropyridin-2-yl)-2-fluorophenyl]-1H-benzoimidazole,
4-chloro-2-[4-(3,5-dichloropyridin-2-yl)-2-fluorophenyl]-6-trifluoromethyl-1H-benzoimidazole,
2-[4-(3,5-dichloropyridin-2-yl)-2-fluorophenyl]-4,6-bistrifluoromethyl-1H-benzoimidazole,
4-chloro-2-[4-(3-chloro-5-trifluoromethylpyridin-2-yl)-2-fluorophenyl]-6-trifluoromethyl-1H-benzoimidazole,
2-[4-(3-chloro-5-trifluoromethylpyridin-2-yl)-2-fluorophenyl]-6-trifluoromethyl-1H-imidazo[4,5-b]pyridine,
2-[4-(3-chloro-5-trifluoromethylpyridin-2-yl)-2-fluorophenyl]-6-methoxy-1H-benzoimidazole,
N-[3,3'-difluoro-4'-(6-methoxy-1H-benzoimidazole-2-yl)biphenyl-4-yl]methanesulfonamide,
2-[2-fluoro-4-(3-trifluoromethylpyridin-2-yl)phenyl]-6-trifluoromethyl-1H-benzoimidazole,
6-tert-butyl-2-[2-fluoro-4-(3-trifluoromethylpyridin-2-yl)phenyl]-1H-benzoimidazole,
6-chloro-2-[2-fluoro-4-(3-trifluoromethylpyridin-2-yl)phenyl]-1H-benzoimidazole,
5-chloro-2-[2-fluoro-4-(3-trifluoromethylpyridin-2-yl)phenyl]-1H-benzoimidazole,
4-chloro-2-[2-fluoro-4-(3-trifluoromethylpyridin-2-yl)phenyl]-6-trifluoromethyl-1H-benzoimidazole,
7-chloro-2-[2-fluoro-4-(3-trifluoromethylpyridin-2-yl)phenyl]-5-trifluoromethyl-1H-benzoimidazole,
2-(2-fluoro-4-pyridin-2-yl)phenyl-6-trifluoromethyl-1H-benzoimidazole,
6-tert-butyl-2-(2-fluoro-4-pyridin-2-yl)phenyl-1H-benzoimidazole,
6-chloro-2-(2-fluoro-4-pyridin-2-yl)phenyl-1H-benzoimidazole,
2-(2-fluoro-4-pyridin-2-yl)phenyl-4,6-bistrifluoromethyl-1H-benzoimidazole,
2-[2-chloro-4-(3-chloropyridin-2-yl)phenyl]-6-trifluoromethyl-1H-benzoimidazole,
4-chloro-2-[2-chloro-4-(3-chloropyridin-2-yl)phenyl]-6-trifluoromethyl-1H-benzoimidazole,
2-[2-chloro-4-(3-chloropyridin-2-yl)phenyl]-6-trifluoromethyl-1H-imidazo[4,5-b]pyridine,
2-[2-chloro-4-(3,5-dichloropyridin-2-yl)phenyl]-6-trifluoromethyl-1H-benzoimidazole,
4-chloro-2-[2-chloro-4-(3,5-dichloropyridin-2-yl)phenyl]-6-trifluoromethyl-1H-benzoimidazole,
2-[2-chloro-4-(3,5-dichloropyridin-2-yl)phenyl]-4,6-bistrifluoromethyl-1H-benzoimidazole,
2-[2-chloro-4-(3,5-dichloropyridin-2-yl)phenyl]-6-trifluoromethyl-1H-imidazo[4,5-b]pyridine,
2-[2-chloro-4-(3-chloro-5-trifluoromethylpyridin-2-yl)phenyl]-6-trifluoromethyl-1H-benzoimidazole,
4-chloro-2-[2-chloro-4-(3-chloro-5-trifluoromethylpyridin-2-yl)phenyl]-6-trifluoromethyl-1H-benzoimidazole,
N-[4'-(6-tert-butyl-1H-benzoimidazole-2-yl)-3'-chloro-3-fluorobiphenyl-4-yl]methanesulfonamide,
N-[3'-chloro-4'-(4-chloro-6-trifluoromethyl-1H-benzoimidazole-2-yl)-3-fluorobiphenyl-4-yl]methanesulfonamide,
N-[4'-(4,6-bistrifluoromethyl-1H-benzoimidazole-2-yl)-3'-chloro-3-fluorobiphenyl-4-yl]methanesulfonamide,
2-[2-chloro-4-(3-trifluoromethylpyridin-2-yl)phenyl]-6-trifluoromethyl-1H-benzoimidazole,
4-chloro-2-[2-chloro-4-(3-trifluoromethylpyridin-2-yl)phenyl]-6-trifluoromethyl-1H-benzoimidazole,
2-[2-chloro-4-(3-trifluoromethylpyridin-2-yl)phenyl]-4,6-bistrifluoromethyl-1H-benzoimidazole,
6-tert-butyl-2-[2-chloro-4-(3-methylpyridin-2-yl)phenyl]-1H-benzoimidazole,
6-chloro-2-(2-chloro-4-pyridin-2-ylphenyl)-1H-benzoimidazole,
2-(2-chloro-4-pyridin-2-ylphenyl)-6-trifluoromethyl-1H-imidazo[4,5-b]pyridine,
2-(2-chloro-4-pyridin-2-ylphenyl)-6-methoxy-1H-benzoimidazole,
2-[4-(3-chloropyridin-2-yl)naphthalen-1-yl]-6-trifluoromethyl-1H-benzoimidazole,
6-tert-butyl-2-[4-(3-chloropyridin-2-yl)naphthalen-1-yl]-1H-benzoimidazole,
2-[4-(3-chloropyridin-2-yl)naphthalen-1-yl]-4,6-bistrifluoromethyl-1H-benzoimidazole,
2-[4-(3-chloropyridin-2-yl)naphthalen-1-yl]-6-trifluoromethyl-1H-imidazo[4,5-b]pyridine,
6-tert-butyl-2-[4-(3,5-dichloropyridin-2-yl)naphthalen-1-yl]-1H-benzoimidazole,
2-[4-(3,5-dichloropyridin-2-yl)naphthalen-1-yl]-4,6-bistrifluoromethyl-1H-benzoimidazole,
6-tert-butyl-2-[4-(3-chloro-5-trifluoromethylpyridin-2-yl)naphthalen-1-yl]-1H-benzoimidazole,
2-[4-(3-chloro-5-trifluoromethylpyridin-2-yl)naphthalen-1-yl]-4,6-bistrifluoromethyl-1H-benzoimidazole,
N-{4-[4-(4,6-bistrifluoromethyl-1H-benzoimidazole-2-yl)naphthalen-1-yl]-2-fluorophenyl}methanesulfonamide,
6-trifluoromethyl-2-[4-(3-trifluoromethylpyridin-2-yl)naphthalen-1-yl]-1H-benzoimidazole,
6-tert-butyl-2-(4-pyridin-2-ylnaphthalen-1-yl)-1H-benzoimidazole,
2-(4-pyridin-2-ylnaphthalen-1-yl)-4,6-bistrifluoromethyl-1H-benzoimidazole,
6-tert-butyl-2-[3-chloro-4-(3-chloropyridin-2-yl)phenyl]-1H-benzoimidazole,
2-[3-chloro-4-(3,5-dichloropyridin-2-yl)phenyl]-6-trifluoromethyl-1H-benzoimidazole,
6-tert-butyl-2-[3-chloro-4-(3,5-dichloropyridin-2-yl)phenyl]-1H-benzoimidazole,
2-[3-chloro-4-(3,5-dichloropyridin-2-yl)phenyl]-6-methoxy-1H-benzoimidazole,
2-[3-chloro-4-(3,5-dichloropyridin-2-yl)phenyl]-5-methoxy-1H-benzoimidazole, 2-[3-chloro-4-(3-chloro-5-trifluoromethylpyridin-2-yl)phenyl]-6-trifluoromethyl-1H-benzoimidazole,
6-tert-butyl-2-[3-chloro-4-(3-chloro-5-trifluoromethylpyridin-2-yl)phenyl]-1H-benzoimidazole,
2-[3-chloro-4-(3-chloro-5-trifluoromethylpyridin-2-yl)phenyl]-6-methoxy-1H-benzoimidazole,
2-[3-chloro-4-(3-chloro-5-trifluoromethylpyridin-2-yl)phenyl]-5-methoxy-1H-benzoimidazole,
N-[2'-chloro-4'-(4-chloro-6-trifluoromethyl-1H-benzoimidazole-2-yl)-3-fluorobiphenyl-4-yl]methanesulfonamide,
N-[4'-(4,6-bistrifluoromethyl-1H-benzoimidazole-2-yl)-2'-chloro-3-fluorobiphenyl-4-yl]methanesulfonamide,
2-(3-chloro-4-pyridin-2-ylphenyl)-6-trifluoromethyl-1H-benzoimidazole,
6-tert-butyl-2-(3-chloro-4-pyridin-2-ylphenyl)-1H-benzoimidazole,
6-chloro-2-(3-chloro-4-pyridin-2-ylphenyl)-1H-benzoimidazole,
4-chloro-2-(3-chloro-4-pyridin-2-ylphenyl)-6-trifluoromethyl-1H-benzoimidazole,
5,6-dichloro-2-(3-chloro-4-(pyridin-2-yl)phenyl)-1H-benzoimidazole,
6-bromo-2-(3-chloro-4-(pyridin-2-yl)phenyl)-1H-benzoimidazole,
2-[3-chloro-4-(3-trifluoromethylpyridin-2-yl)phenyl]-6-trifluoromethyl-1H-benzoimidazole,
6-tert-butyl-2-[3-chloro-4-(3-trifluoromethylpyridin-2-yl)phenyl]-1H-benzoimidazole,
6-chloro-2-[3-chloro-4-(3-trifluoromethylpyridin-2-yl)phenyl]-1H-benzoimidazole,
2-[3-chloro-4-(3-trifluoromethylpyridin-2-yl)phenyl]-6-methoxy-1H-benzoimidazole,
2-[3-chloro-4-(3-methylpyridin-2-yl)phenyl]-6-trifluoromethyl-1H-benzoimidazole,
3-chloro-6'-(6-trifluoromethyl-1H-benzoimidazole-2-yl)-[2,3']bipyridine,
3-chloro-6'-(6-chloro-1H-benzoimidazole-2-yl)-[2,3']bipyridine,
3-chloro-6'-(4-chloro-6-trifluoromethyl-1H-benzoimidazole-2-yl)-[2,3']bipyridine,
6'-(4,6-bistrifluoromethyl-1H-benzoimidazole-2-yl)-3-chloro-[2,3']bipyridine,
4-bromo-2-(5-(3-chloropyridin-2-yl)pyridin-2-yl)-6-(trifluoromethyl)-1H-benzoimidazole,
6-bromo-2-(5-(3-chloropyridin-2-yl)pyridin-2-yl)-1H-benzoimidazole,
6'-(6-tert-butyl-1H-benzoimidazole-2-yl)-3-chloro-[2,3']bipyridine,
3-chloro-6'-(5,6-dichloro-1H-benzoimidazole-2-yl)-[2,3']bipyridine,
3-chloro-6'-(4,6-dibromo-1H-benzoimidazole-2-yl)-[2,3']bipyridine,
6'-(6-bromo-1H-imidazo[4,5-b]pyridine-2-yl)-3-chloro-[2,3']bipyridine,
3-chloro-6'-(6-morpholin-4-yl-1H-benzoimidazole-2-yl)-[2,3']bipyridine,
3-chloro-6'-(6-thiomorpholin-4-yl-1H-benzoimidazole-2-yl)-[2,3']bipyridine,
3-chloro-6'-(4-morpholin-4-yl-6-trifluoromethyl-1H-benzoimidazole-2-yl)-[2,3']bipyridine,
3-chloro-6'-(4-thiomorpholin-4-yl-6-trifluoromethyl-1H-benzoimidazole-2-yl)-[2,3']bipyridine,
3-chloro-6'-(4-pyrrolidin-1-yl-6-trifluoromethyl-1H-benzoimidazole-2-yl)-[2,3']bipyridine,
3,5-dichloro-6'-(6-trifluoromethyl-1H-benzoimidazole-2-yl)-[2,3']bipyridine,
6'-(6-tert-butyl-1H-benzoimidazole-2-yl)-3,5-dichloro-[2,3']bipyridine,
3,5-dichloro-6'-(6-chloro-1H-benzoimidazole-2-yl)-[2,3']bipyridine,
3,5-dichloro-6'-(4-chloro-6-trifluoromethyl-1H-benzoimidazole-2-yl)-[2,3']bipyridine,
6'-(4,6-bistrifluoromethyl-1H-benzoimidazole-2-yl)-3,5-dichloro-[2,3']bipyridine,
6'-(4,6-bistrifluoromethyl-1H-benzoimidazole-2-yl)-3-chloro-5-trifluoromethyl-[2,3']bipyridine,
6'-(6-methoxy-1H-benzoimidazole-2-yl)-3-chloro-5-trifluoromethyl-[2,3']bipyridine,
3-trifluoromethyl-6'-(6-trifluoromethyl-1H-benzoimidazole-2-yl)-[2,3']bipyridine,
6'-(6-tert-butyl-1H-benzoimidazole-2-yl)-3-trifluoromethyl-[2,3']bipyridine,
6'-(6-chloro-1H-benzoimidazole-2-yl)-3-trifluoromethyl-[2,3']bipyridine,
6'-(4-chloro-6-trifluoromethyl-1H-benzoimidazole-2-yl)-3-trifluoromethyl-[2,3']bipyridine,
6'-(5-trifluoromethyl-7-chloro-1H-benzoimidazole-2-yl)-3-trifluoromethyl-[2,3']bipyridine,
6'-(4,6-bistrifluoromethyl-1H-benzoimidazole-2-yl)-3-trifluoromethyl-[2,3']bipyridine,
6'-(5,6-dichloro-1H-benzoimidazole-2-yl)-3-trifluoromethyl-[2,3']bipyridine,
4-bromo-6-(trifluoromethyl)-2-(5-(3-(trifluoromethyl)pyridin-2-yl)pyridin-2-yl)-1H-benzoimidazole,
6-bromo-2-(5-(3-(trifluoromethyl)pyridin-2-yl)pyridin-2-yl)-1H-benzoimidazole,
6-fluoro-2-(5-(3-(trifluoromethyl)pyridin-2-yl)pyridin-2-yl)-1H-benzoimidazole,
6'-(6-bromo-1H-imidazo[4,5-b]pyridine-2-yl)-3-trifluoromethyl[2,3']bipyridine,
6'-(4,6-dibromo-1H-benzoimidazole-2-yl)-3-trifluoromethyl-[2,3']bipyridine,
6'-(6-morpholin-4-yl-1H-benzoimidazo-2-yl)-3-trifluoromethyl-[2,3']bipyridine,
6'-(4-morpholin-4-yl-6-trifluoromethyl-1H-benzoimidazole-2-yl)-3-trifluoromethyl-[2,3']bipyridine,
6'-(6-chloro-1H-benzoimidazole-2-yl)-[2,3']bipyridine,
6'-(6-trifluoromethyl-1H-imidazo[4,5-b]pyridine-2-yl)-[2,3']bipyridine,
5,6-dichloro-2-(5-(pyridin-2-yl)pyridin-2-yl)-1H-benzoimidazole,
6-tert-butyl-2-(6-naphthalen-1-ylpyridin-3-yl)-1H-benzoimidazole,
2-(6-naphthalen-1-ylpyridin-3-yl)-4,6-bistrifluoromethyl-1H-benzoimidazole,
2-(6-naphthalen-1-ylpyridin-3-yl)-5,7-bistrifluoromethyl-1H-benzoimidazole,
6-(trifluoromethyl)-2-(6-(naphthalen-1-yl)pyridin-3-yl)-1H-benzoimidazole,
6-chloro-2-(6-(naphthalen-1-yl)pyridin-3-yl)-1H-benzoimidazole,
2-(4-pyrrol-1-ylphenyl]-6-trifluoromethyl-1H-benzoimidazole,
2-(4-pyrrol-1-ylphenyl)-3H-imidazo[4,5-b]pyridine,
6-chloro-2-(4-pyrrol-1-ylphenyl]-1H-benzoimidazole,
6-tert-butyl-2-(4-pyrrol-1-ylphenyl]-1H-benzoimidazole,
6-fluoro-2-(4-pyrrol-1-ylphenyl]-1H-benzoimidazole,
2-biphenyl-4-yl-6-trifluoromethyl-1H-benzoimidazole,
2-biphenyl-4-yl-3H-imidazo[4,5-b]pyridine,
2-biphenyl-4-yl-6-chloro-1H-benzoimidazole,
2-biphenyl-4-yl-6-tert-butyl-1H-benzoimidazole,
2-biphenyl-4-yl-6-fluoro-1H-benzoimidazole,
2-biphenyl-4-yl-6-methoxy-1H-benzoimidazole, 2-(4-phenoxyphenyl-6-trifluoromethyl)-1H-benzoimidazole,
2-(4-phenoxyphenyl)-3H-imidazo[4,5-b]pyridine,
6-chloro-2-(4-phenoxyphenyl)-1H-benzoimidazole,
6-tert-butyl-2-(4-phenoxyphenyl)-1H-benzoimidazole,
6-fluoro-2-(4-phenoxyphenyl)-1H-benzoimidazole,
6-methoxy-2-(4-phenoxyphenyl)-1H-benzoimidazole,
2-[3-(4-chloropyrazol-1-ylmethyl)phenyl]-6-trifluoromethyl-1H-benzoimidazole,
6-chloro-2-[3-(4-chloropyrazol-1-ylmethyl)phenyl]-1H-benzoimidazole,
6-tert-butyl-2-[3-(4-chloropyrazol-1-ylmethyl)phenyl]-1H-benzoimidazole,
2-[3-(4-chloropyrazol-1-ylmethyl)phenyl]-6-fluoro-1H-benzoimidazole,
phenyl-[4-(6-trifluoromethyl-1H-benzoimidazole-2-yl)phenyl]methanone,
[4-(6-tert-butyl-1H-benzoimidazole-2-yl)phenyl]phenylmethanone,
2-[4-(3-chloropyridin-2-yl)phenyl]-6-trifluoromethyl-1H-benzoimidazole chloride,
6-tert-butyl-2-[4-(3-chloropyridin-2-yl)phenyl]-1H-benzoimidazole chloride,
6-tert-butyl-2-[4-(3-chloropyridin-2-yl)naphthalen-1-yl]-1H-benzoimidazole chloride,
6'-(4,6-bistrifluoromethyl-1H-benzoimidazole-2-yl)-3-chloro[2,3']bipyridine chloride,
3-trifluoromethyl-6'-(6-trifluoromethyl-1H-benzoimidazole-2-yl)-[2,3']bipyridine chloride,
6-tert-butyl-2-[4-(3-chloropyridin-2-yl)phenyl]-1H-benzoimidazole sodium salt,
3-trifluoromethyl-6'-(6-trifluoromethyl-1H-benzoimidazole-2-yl)-[2,3']bipyridine sulfate,
3-trifluoromethyl-6'-(6-trifluoromethyl-1H-benzoimidazole-2-yl)-[2,3']bipyridine phosphate,
3-trifluoromethyl-6'-(6-trifluoromethyl-1H-benzoimidazole-2-yl)-[2,3']bipyridine methansulfonate, and
3-trifluoromethyl-6'-(6-trifluoromethyl-1H-benzoimidazole-2-yl)-[2,3']bipyridine benzenesulfonate.

In accordance with another aspect of the present invention, a method for preparing the compounds of Chemical Formula 1 is provided. The method may be conducted to chemically synthesize the compounds in accordance with the following reaction scheme, but is not limited thereto. The reaction scheme guides the preparation of representative compounds of the present invention, but modifications may be made to reagents and starting materials well known in the art so as to employ other compounds.

Having chiral centers, some of the compounds represented by Chemical Formula 1 may be in form of enantiomers. Therefore, it should be noted that all optical isomers, R or S type stereoisomers, racemates and enantiomers of the compounds of Chemical Formula 1 are included within the scope of the present invention. In addition, the present invention includes the use of racemates, one or more enantiomers, one or more diastereomers, or combinations thereof, and methods for separating or preparing the isomers.

In accordance with a further aspect of the present invention, provided is a pharmaceutical composition comprising the compound of Chemical Formula 1 as an active ingredient in an effective amount in combination with a pharmaceutically acceptable carrier.

The following reaction scheme 1 accounts for the synthesis of the compounds represented by Chemical Formula 1:

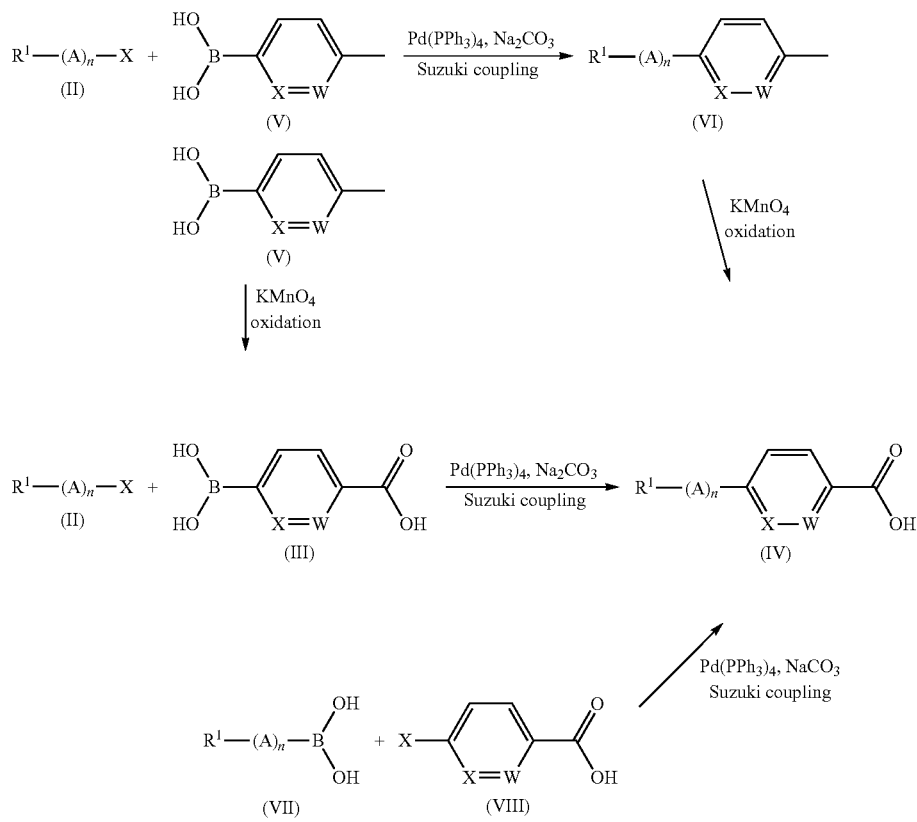

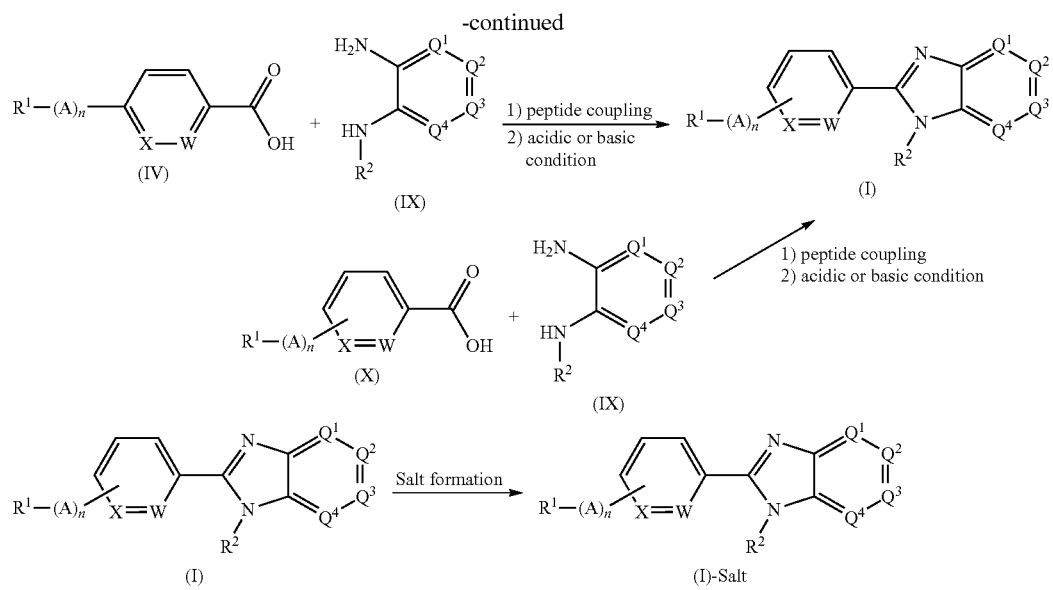

-continued

As shown in Reaction Scheme 1, benzoic acid derivatives (IX) useful in synthesizing the object compound benzoimidazole compound 1 can be prepared by reacting commercially available halogen compounds (II) with boronic acid (III) in the presence of a palladium catalyst and a base in a typical reaction condition with the aid of microwaves (Tapolcsanyi et. al., Tetrahedron, 2002, 58, 10137).

If not commercially available, boronic acid can be obtained through the oxidation of methylboronic acid (V) (Sharma et. al., Bioorg. Med. Chem. Lett. 1998, 8, 3459-3464). Alternatively, methylboronic acid (V) is reacted with a halogen compound (II), followed by oxidation to afford the benzoic acid derivatives (IX).

On the other hand, halobenzoic acid (VIII) may be reacted with commercially available boronic acid (VII), or a commercially available benzoic acid (X) may be used.

Such synthetic or commercially available benzoic acid derivatives are condensed with diamine derivatives (IX) in the presence of O-(7-azabenzotriazol-1-yl)-N,N,N',N'-tetramethyleuronium hexafluorophosphate to synthesize the intermediates, that is, amide compounds, which are then subjected to cyclization into the object compound benzoimidazole 1. In this case, the preparation of the benzoimidazole 1 may be achieved in the presence of acetic acid, a hydrochloric acid solution (Roglic et. al., Pharmazie, 2001, 56, 803), POCl$_3$ (Ries, et. al., J. Med. Chem., 1993, 36, 4040), polyphosphoric acid (Ries, et. al., J. Med. Chem., 1993, 36, 4040), or pyridine (Abha et. al., Indian Journal of Chemistry, 2002, 41, 1978) in a heated condition or with the aid of microwave (Lu, et. al., Syn. Comm. 2002, 32, 3703).

As shown above, the compounds of Chemical Formula 1 may be in form of salts, particularly pharmaceutically acceptable salts. The pharmaceutically available salts suitable for use in the present invention are those typically used in the art, such as acid addition salts, and include those disclosed in the literature (J. Pharm. Sci., 1977, 66, 1).

Examples of pharmaceutically acceptable acid addition salts suitable for use in the present invention include salts of inorganic acids, such as hydrochloric acid, hydrobromic acid, phosphoric acid, orthophosphoric acid, sulfuric acid, and so on, and salts of organic acids, such as methanesulfonic acid, benzenesulfonic acid, toluenesulfonic acid, acetic acid, propionic acid, lactic acid, citric acid, fumaric acid, malic acid, succinic acid, salicylic acid, maleic acid, glycerophosphoric acid, acetylsalicylic acid, and so on.

In addition, pharmaceutically acceptable metal salts may be prepared using bases. Alkali metal salts or alkaline earth metal salts, for example, may be obtained by dissolving compounds in an excess of an alkali metal hydroxide or alkaline earth metal hydroxide solution, filtering off non-dissolved compound salts, and vaporizing and drying the filtrate. In this regard, sodium, potassium or calcium salts are pharmaceutically suitable metal salts. In addition, silver salts corresponding to the metal salts can be obtained by reacting alkaline metal or alkali earth metal with suitable silver salts (e.g., nitrate).

Pharmaceutically unacceptable salts and/or solvates of compounds of Chemical Formula 1 may be useful as intermediates for the preparation of pharmaceutically acceptable salts and/or solvates of compounds of Chemical Formula 1, or for the preparation of the compounds themselves of Chemical Formula 1, which also constitutes another aspect of the present invention.

Compounds of Chemical Formula 1 may be prepared in crystalline or non-crystalline forms. If crystalline, the compounds may be arbitrarily hydrated or solvated. Compounds with arbitrary numbers of water molecules as well as stoichiometric hydrates fall into the scope of the present invention.

Suitable are solvates which are pharmaceutically acceptable, like hydrates.

Solvates suitable for use in the present invention comprise both stoichiometric and non-stoichiometric solvates.

It is believed that, because they possess antagonistic activity against the vanilloid receptor, compounds of Chemical Formula 1 and pharmaceutically acceptable salts thereof have potential to be used for the prevention and treatment of indications and the treatment of the pain relevant thereto.

The indications may be exemplified by pain, acute pain, chronic pain, neuropathic pain, postoperative pain, migraine, arthralgia, neuropathy, nerve injury, diabetic neuropathy, neurological illness, neurodermatitis, stroke, bladder hypersensitivity, irritable bowel syndrome, respiratory disorders such as asthma, chronic obstructive pulmonary disease, etc., burning, psoriasis, itching, vomiting, irritation of the skin, eyes, and mucous membranes, gastric-duodenal ulcers, inflammatory intestinal diseases, and inflammatory diseases.

Thus, the present invention also provides the compounds of Chemical Formula 1, or pharmaceutically acceptable salts or solvates thereof, which are useful as active ingredients for the prevention and treatment of indications.

Particularly, the present invention provides the compounds of Chemical Formula 1, or pharmaceutically acceptable salts or solvates thereof, which are useful for the prevention and treatment of pain.

Further, the present invention provides a method for preventing or treating symptoms for which antagonism to the vanilloid receptor is helpful in the therapy thereof, comprising the administration of compounds of Chemical Formula 1, or pharmaceutical acceptable salts or solvates thereof in a therapeutically effective amount to mammalians having the symptoms.

The present invention also provides uses of compounds of Chemical Formula 1, or pharmaceutically acceptable salts or solvates in the prevention and treatment of indications for the therapy of which antagonism to the vanilloid receptor is helpful.

For use in therapy, compounds are generally formulated according to standard pharmaceutical practice. Thus, the present invention provides a pharmaceutical composition comprising a compound of Chemical formula 1 or a pharmaceutically acceptable salt or solvate thereof, in combination with an additive such as a pharmaceutically acceptable carrier, adjuvant, or diluent. For example, the compounds of Chemical Formula 1 may be dissolved in oils, propyleneglycol, or other solvents, which are usually used for the preparation of injections. Illustrative, but non-limitative examples of the carrier include physiological saline, polyethylene glycol, ethanol, vegetable oil, and isopropylmyristate. For topical use, the compounds of the present invention may be formulated into ointments or creams.

Below, a description will be given of formulation methods and carriers, but not intended to limit the present invention.

Pharmaceutical dosage forms of the compounds of the present invention include pharmaceutically acceptable salts or solvates of the compounds of the present invention alone or in combination with other pharmaceutically active compounds suitably bound or assembled thereto.

The compounds of the present invention may be dissolved, suspended or emulsified in an aqueous solvent such as physiological saline, 5% dextrose, etc., or a non-aqueous solvent, such as synthetic fatty acid glyceride, higher fatty acid esters, propylene glycol, etc. The formulation of the present invention may comprise conventional additives such as dissolving agents, isotonic agents, suspensions, emulsifying agents, and preservatives.

Depending on a patient's state and weight, severity of disease, dosage form, and administration route and period, the administration dose of the compounds of the present invention may be suitably selected by those skilled in the art. For effective therapy, the compounds of the present invention are administered in a dose from 0.0001 to 100 mg/weight kg a day and preferably in a dose from 0.001 to 100 mg/weight kg a day. Administration may be conducted once or many times in a partitioned manner in a day.

According to the administration method, the pharmaceutical composition may comprise the compound of the present invention in an amount from 0.001 to 99 weight %, and preferably in an amount from 0.01 to 60 weight %.

The pharmaceutical composition of the present invention may be administered via various routes to mammalians such as mice, rats, livestock, humans, etc. All administration types may be expected, including, for example, oral or rectal administration, intravenous, intramuscular, subcutaneous, intraendometrial or intracerebroventricular injection.

A better understanding of the present invention may be obtained through the following examples which are set forth to illustrate, but are not to be construed as the limit of the present invention.

Example 1

Preparation of 2-[4-(3-Chloropyridin-2-yl)-phenyl]-6-trifluoromethyl-1H-benzoimidazole

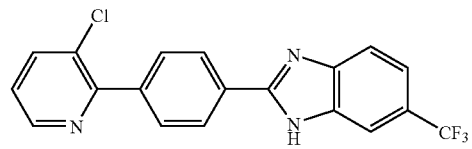 [SMILES: FC(F)(F)c1ccc2nc(-c3ccc(-c4ncccc4Cl)cc3)[nH]c2c1]

(1) Preparation of 4-(3-chloropyridin-2-yl)benzoic acid

To a solution of 5.3 g (36.1 mmol) 2,3-dichloropyridine in 200 mL 1,2-dimethoxyethane and 200 mL distilled water were added 22.3 g (0.21 mol) $Na_2CO_3$, 5.0 g (30.1 mmol) 4-carboxylphenylboronic acid and 0.5 g $Pd(PPh_3)_4$, followed by mixing for 18 hours under a heat flux condition by stirring. After being cooled to room temperature, the solution was 50% concentrated in a vacuum. The aqueous layer was washed with ethyl acetate and adjusted into pH 1 with conc. HCl. Thereafter, extraction with ethyl acetate was conducted three times and the organic layer was dried over magnesium sulfate and concentrated in a vacuum. The concentrate was separated using column chromatography (developing solvent: chloroform/methanol=10/1) to afford 5.3 g of 4-(3-chloropyridin-2-yl)benzoic acid as a white precipitate (yield: 75%).

$^1$H NMR ($CD_3OD$) δ: 8.57 (dd, 1H, J=4.8, 1.4 Hz), 8.13 (dd, 2H, J=6.9, 1.7 Hz), 8.03 (dd, 1H, J=8.1, 1.4 Hz), 7.75 (dd, 2H, J=6.9, 1.7 Hz), 7.44 (dd, 1H, J=8.1, 4.8 Hz)

(2) Preparation of 4-(3-chloropyridin-2-yl)benzoic acid

To a solution of 0.5 g (2.45 mmol) 3-chloro-2-p-tolyl-pyridine in 5 mL pyridine was added 2.5 mL distilled water, and then 1.36 g (8.59 mmol) potassium permanganate, followed by carefully stirring the solution to prevent potassium permanganate from contacting the container of the solution. Using a microwave reactor (Initiator Sixty, Biotage), the solution was allowed to react at 100° C. for 5 min. The reaction solution was filtered to remove solids using celite. After the vacuum concentration of the filtrate, 10 mL distilled water and 10 mL ethyl acetate were added to the concentrate. The addition of a 1.0N hydrochloric acid solution increased the pH of the aqueous solution to 4.0 before stirring for 40 min. The separated ethyl acetate was dried over anhydrous magnesium sulfate and concentrated in a vacuum. A solution of the concentrate in methanol was separated using column chromatography (chloroform/methanol=10:1) to produce 0.35 g of 4-(3-chloropyridin-2-yl)benzoic acid (yield 61%).

(3) Preparation of 2-[4-(3-chloropyridin-2-yl)phenyl]-6-trifluoromethyl-1H-benzoimidazole 0.44 g (2.5 mmol) 4-trifluoromethylbenzene-1,2-diamine, 1.0 mL (5.0 mmol) diisopropylethylamine and 1.1 g (6 mmol) O-(7-azabenzotriazol-yl)-N,N,N',N'-tetramethyleuronium hexafluorophosphate were added to a solution of 0.59 g (2.5 mmol) 4-(3-chloropyridin-2-yl)benzoic acid in 25 mL dimethylformamide, which was then stirred at room temperature for 16 hours and vacuum concentrated. The concentrate thus obtained was dissolved in ethyl acetate, washed with saturated $NaHCO_3$ and saturated NaCl, dried over magnesium sulfate, and concentrated in a vacuum. The residue was dissolved in acetic acid/toluene (15 mL/1.5 mL) and stirred at 75° C. for 3 hours, followed by vacuum concentration. Again, the concentrate was dissolved in ethyl acetate, washed with saturated $NaHCO_3$ and saturated NaCl, dried over magnesium sulfate, and vacuum concentrated. The residue was separated using column chromatography (developing solvent: chloroform/methanol=30/1) to produce 0.77 g of 2-[4-(3-chloropyridin-2-yl)phenyl]-6-trifluoromethyl-1H-benzoimidazole (yield 82%).

$^1$H NMR ($CDCl_3$) δ: 8.65 (m, 1H), 8.06 (d, 2H, J=8.4 Hz), 7.93 (s, 1H), 7.85 (d, 1H, J=8.2 Hz), 7.77 (d, 2H, J=8.4 Hz), 7.69 (d, 1H, J=8.2 Hz), 7.52 (d, 1H, J=8.2 Hz), 7.34-7.30 (m, 1H)

(4) Preparation of 2-[4-(3-chloropyridin-2-yl)phenyl]-6-trifluoromethyl-1H-benzoimidazole To a solution of 0.58 g (2.5 mmol) 4-(3-chloropyridin-2-yl)benzoic acid in 30 mL anhydrous pyridine was added 0.44 g (2.5 mmol) 4-trifluoromethylbenzene-1,2-diamine, followed by stirring for 6 hours in a heat flux condition. After cooling to room temperature, cold water (100 mL) containing HCl (10 mL) was added to the solution, which was then allowed to stand for 30 min to form precipitates. These were separated using column chromatography (developing solvent: chloroform/methanol=30/1) to produce 0.70 g of 2-[4-(3-chloropyridin-2-yl)phenyl]-6-trifluoromethyl-1H-benzoimidazole (yield 75%).

(5) Preparation of 2-[4-(3-chloropyridin-2-yl)phenyl]-6-trifluoromethyl-1H-benzoimidazole To a solution of 0.64 g (2.75 mmol) 4-(3-chloropyridin-2-yl)benzoic acid in 25 mL 4N HCl was added 0.44 g (2.5 mmol) 4-trifluoromethylbenzene-1,2-diamine, followed by stirring at 180° C. for 6 hours. The solution was cooled to room temperature before the addition of 10% $NaHCO_3$ (10 mL) and then extraction with ethyl acetate. The organic layer was dried over magnesium sulfate and vacuum concentrated. The residue thus obtained was separated using column chromatography (developing solvent: chloroform/methanol=30/1) to produce 0.61 g of 2-[4-(3-chloropyridin-2-yl)phenyl]-6-trifluoromethyl-1H-benzoimidazole (yield 65%).

(6) Preparation of 2-[4-(3-chloropyridin-2-yl)phenyl]-6-trifluoromethyl-1H-benzoimidazole To a solution of 0.64 g (2.75 mmol) 4-(3-chloropyridin-2-yl)benzoic acid in 20 mL $POCl_3$ was added 0.44 g (2.5 mmol) 4-trifluoromethylbenzene-1,2-diamine, followed by stirring for 3 hours in a heat flux condition. The solution was cooled to room temperature and dissolved in distilled water. After the adjustment of pH to 8-10 with ammonia, extraction was conducted using ethyl acetate. The organic layer was dried over magnesium sulfate and vacuum concentrated. The residue thus obtained was separated using column chromatography (developing solvent: chloroform/methanol=30/1) to produce 0.61 g of 2-[4-(3-chloropyridin-2-yl)phenyl]-6-trifluoromethyl-1H-benzoimidazole (yield 65%).

(7) Preparation of 2-[4-(3-chloropyridin-2-yl)phenyl]-6-trifluoromethyl-1H-benzoimidazole To a solution of 0.70 g (3.0 mmol) 4-(3-chloropyridin-2-yl)benzoic acid in 25 g polyphosphoric acid was added 0.44 g (2.5 mmol) 4-trifluoromethylbenzene-1,2-diamine, followed by stirring at 150° C. for 20 hours. Then, the solution was cooled to room temperature, dissolved in distilled water and adjusted to pH 9 to form precipitates. These precipitates were purified using column chromatography (developing solvent: chloroform/methanol=30/1) to afford 0.61 g of 2-[4-(3-chloropyridin-2-yl)phenyl]-6-trifluoromethyl-1H-benzoimidazole (yield 65%).

(8) Preparation of 2-[4-(3-chloropyridin-2-yl)phenyl]-6-trifluoromethyl-1H-benzoimidazole A solution of 0.70 g (3.0 mmol) 4-(3-chloropyridin-2-yl)benzoic acid and 0.44 g (2.5 mmol) 4-trifluoromethylbenzene-1,2-diamine in 10 mL polyphosphoric acid was stirred for 5 min and irradiated for 15 min with microwaves in a microwave reactor (Initiator Sixty, Biotage). After cooling to room temperature, 20 mL distilled water was added to the solution which was then adjusted to a neutral pH value with NaOH. The precipitates thus obtained was filtered and separated using column chromatography (developing solvent: chloroform/methanol=30/1) to produce 0.72 g of 2-[4-(3-chloropyridin-2-yl)phenyl]-6-trifluoromethyl-1H-benzoimidazole (yield 77%).

(9) Preparation of 2-[4-(3-chloropyridin-2-yl)phenyl]-6-trifluoromethyl-1H-benzoimidazole 0.44 g (2.5 mmol) 4-trifluoromethylbenzene-1,2-diamine, 1.0 mL (5.0 mmol) diisopropylethylamine and 1.1 g (6 mmol) O-(7-azabenzotriazol-1-yl)-N,N,N',N'-tetramethyleuronium hexafluorophosphate were added to a solution of 0.59 g (2.5 mmol) 4-(3-chloropyridin-2-yl)benzoic acid in 25 mL dimethylformamide, which was then stirred for 5 min, irradiated for 15 min with microwaves in a microwave reactor (Initiator Sixty, Biotage) and concentrated in a vacuum. The concentrate was dissolved in ethyl acetate, washed with saturated $NaHCO_3$ and saturated NaCl, and dried over magnesium sulfate, followed by vacuum concentration. The residue thus obtained was dissolved in acetic acid (15 mL) and stirred for 5 min before irradiation for 15 min with microwaves in a microwave reactor (Initiator Sixty, Biotage). Again, the reaction solution was cooled to room temperature, vacuum concentrated, dissolved in ethyl acetate, washed with saturated $NaHCO_3$ and saturated NaCl, and dried over magnesium sulfate, followed by vacuum concentration. The residue was separated using column chromatography (developing solvent: chloroform/methanol=30/1) to produce 0.81 g of 2-[4-(3-chloropyridin-2-yl)phenyl]-6-trifluoromethyl-1H-benzoimidazole (yield 90%).

Examples 2 to 16

The same procedure as in (3) of Example 1 was performed to produce Compounds 2 to 16.

| Cpds | Structures | Yields | Spectrum Data ($^1$H NMR) |
|---|---|---|---|
| 2 | 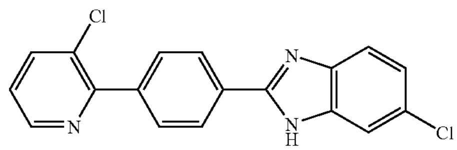 | 81 | (CDCl$_3$) δ: 8.66 (dd, 1H, J = 4.6, 1.4 Hz), 8.03 (d, 2H, J = 8.4 Hz), 7.86 (dd, 1H, J = 8.1, 1.4 Hz), 7.79 (d, 2H, J = 8.4 Hz), 7.58 (br, 1H), 7.53-7.51 (m, 1H), 7.34-7.29 (m, 1H), 7.25-7.22 (m, 1H) |
| 3 | 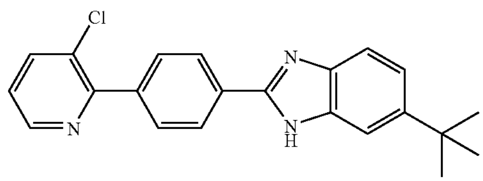 [SMILES: CC(C)(C)c1ccc2nc(-c3ccc(-c4ncccc4Cl)cc3)[nH]c2c1] | 88 | (CDCl$_3$) δ: 8.57 (d, 1H, J = 4.7 Hz), 8.03 (d, 2H, J = 8.2 Hz), 7.77 (d, 1H, J = 8.0 Hz), 7.62 (d, 2H, J = 8.2 Hz), 7.51 (s, 1H), 7.46 (d, 1H, J = 8.5 Hz), 7.25-7.21 (m, 2H), 1.27 (s, 9H) |
| 4 | 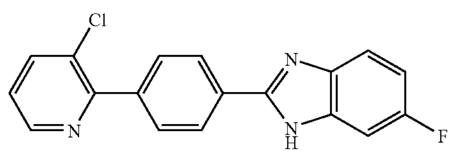 [SMILES: Fc1ccc2nc(-c3ccc(-c4ncccc4Cl)cc3)[nH]c2c1] | 65 | (CDCl$_3$) δ: 8.64 (dd, 1H, J = 4.7, 1.4 Hz), 8.06 (d, 2H, J = 8.4 Hz), 7.85 (d, 1H, J = 1.4 Hz), 7.82 (d, 2H, J = 8.4 Hz), 7.56 (m, 1H), 7.32-7.28 (m, 2H), 7.06-7.00 (m, 1H) |
| 5 | 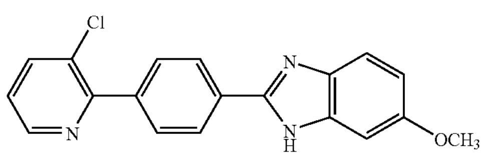 [SMILES: COc1ccc2nc(-c3ccc(-c4ncccc4Cl)cc3)[nH]c2c1] | 66 | (CDCl$_3$) δ: 8.57 (dd, 1H, J = 4.6, 1.4 Hz), 7.98 (d, 2H, J = 8.4 Hz), 7.78 (dd, 1H, J = 8.1, 1.4 Hz), 7.67 (d, 2H, J = 8.4 Hz), 7.41 (d, 1H, J = 8.8 Hz), 7.25-7.21 (m, 1H), 6.94 (d, 1H, J = 2.3 Hz), 6.79 (dd, 1H, J = 8.9, 2.4 Hz), 3.72 (s, 3H) |
| 6 | 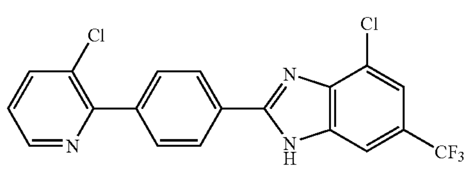 | 75 | (CDCl$_3$) δ: 8.68 (d, 1H), 8.09 (d, 2H), 7.89-7.83 (m, 4H), 7.55 (s, 1H), 7.35-7.26 (m, 1H) |
| 7 | 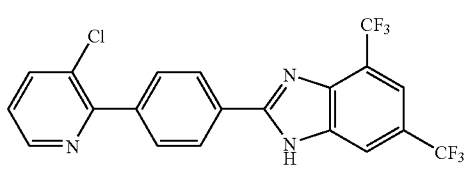 [SMILES: FC(F)(F)c1cc(Cl)c2nc(-c3ccc(-c4ncccc4Cl)cc3)[nH]c2c1] | 78 | (CDCl$_3$) δ: 8.65 (d, 1H), 8.17-8.14 (m, 3H), 7.88-7.79 (m, 4H), 7.32 (dd, 1H) |
| 8 | 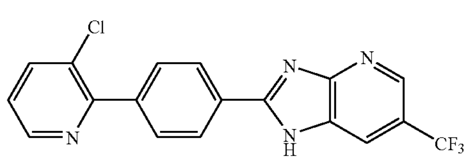 [SMILES: FC(F)(F)c1cnc2nc(-c3ccc(-c4ncccc4Cl)cc3)[nH]c2c1] | 81 | (CDCl$_3$) δ: 8.72 (d, 1H), 8.41 (s, 1H), 8.26 (d, 2H), 7.95 (d, 2H), 7.85 (d, 1H), 7.48-7.21 (m, 2H) |
| 9 | 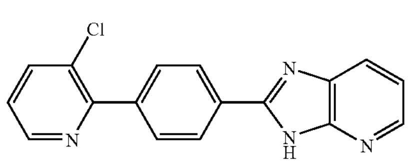 [SMILES: Clc1cccnc1-c1ccc(-c2nc3cccnc3[nH]2)cc1] | 52 | (CDCl$_3$) δ: 8.59-8.62 (m, 2H), 8.13-8.11 (m, 1H), 7.90-7.85 (m, 1H), 7.84-7.81 (m, 1H), 7.78 (d, 2H, J = 8.3 Hz), 7.52 (d, 2H, J = 8.3 Hz), 7.27-7.23 (m, 1H) |
| 10 | 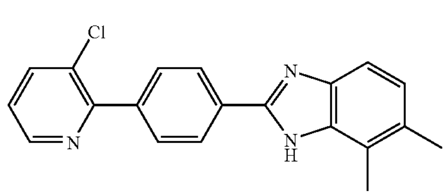 [SMILES: Cc1ccc2nc(-c3ccc(-c4ncccc4Cl)cc3)[nH]c2c1C] | 90 | (CD$_3$OD) δ: 8.61 (d, 1H), 8.25 (d, 2H), 8.04 (d, 1H), 7.91 (d, 2H), 7.48-7.40 (m, 2H), 7.21 (d, 1H), 2.59 (s, 3H), 2.44 (s, 3H) |

| Cpds | Structures | Yields | Spectrum Data ($^1$H NMR) |
|---|---|---|---|
| 11 | 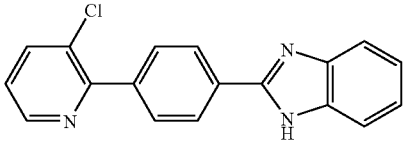 [SMILES: Clc1cccnc1-c1ccc(-c2nc3ccccc3[nH]2)cc1] | 93 | (CD$_3$OD) δ: 8.64 (d, 1H), 8.26 (d, 2H), 8.06 (d, 1H), 8.00 (d, 2H), 7.84-7.80 (m, 2H), 7.58-7.52 (m, 2H), 7.50-7.47 (m, 1H) |
| 12 | 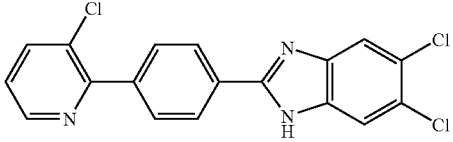 | 94 | (CD$_3$OD) δ: 8.62-8.58 (m, 1H), 8.22 (d, 2H), 8.03 (d, 1H), 7.88 (d, 2H), 7.77-7.73 (m, 2H), 7.47-7.44 (m, 1H) |
| 13 | 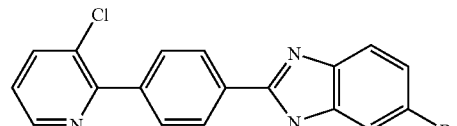 | 62 | (CD$_3$OD) δ: 8.57 (dd, 1H), 8.18 (d, 2H), 8.00 (dd, 1H), 7.84 (d, 2H), 7.76 (d, 1H), 7.54 (d, 1H), 7.39-7.45 (m, 2H) |
| 14 | 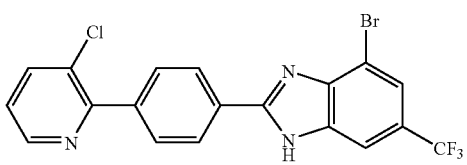 | 83 | (CD$_3$OD) δ: 8.61 (dd, 1H), 8.32 (d, 2H), 8.04 (dd, 1H), 7.91-7.88 (m, 3H), 7.73 (d, 1H), 7.47 (dd, 1H) |
| 15 | 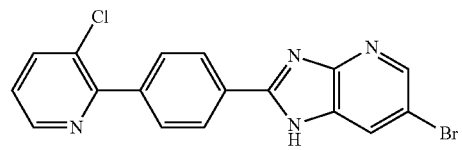 | 57 | (CD$_3$OD) δ: 8.60 (dd, 1H), 8.10 (d, 2H), 8.03 (dd, 1H), 7.96 (dd, 1H), 7.84-7.80 (m, 3H), 7.47 (dd, 1H) |
| 16 | 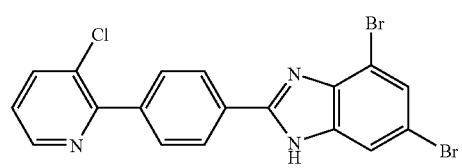 | 85 | (CDCl$_3$) δ: 8.64 (d, 1H), 8.12 (d, 2H), 7.86-7.74 (m, 4H), 7.57 (d, 1H), 7.32 (dd, 1H) |

Example 17

Preparation of 2-[4-(3-chloropyridin-2-yl)phenyl]-6-morpholin-4-yl-1H-benzoimidazole

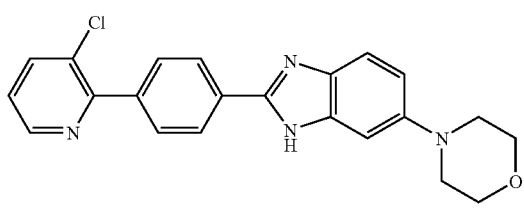 [SMILES: Clc1cccnc1-c1ccc(-c2nc3ccc(N4CCOCC4)cc3[nH]2)cc1]

To a solution of 162 mg (0.42 mmol) 6-bromo-2-(4-(3-chloropyridin-2-yl)phenyl)-1H-benzoimidazole in 6 mL dichloromethane were added 0.2 mL (1.15 mmol) N,N-dimethylisopropylethylamine and 0.1 mL (0.57 mmol) 2-(trimethylsilyl)ethoxymethyl chloride, followed by stirring at room temperature for 16 hours. After vacuum concentration, 26 μL (0.30 mmol) morpholine, 56.3 mg (0.013 mmol) tris(dibenzylidine acetone)dipalladium(0), 10 mg (0.038 mmol) 2-(di-t-butylphosphino)biphenyl, and 38.8 mg (0.41 mmol) sodium-t-botoxide were added to the concentrate, which was then dissolved in 2.5 mL toluene and allowed to react at 90° C. for 10 min in a microwave reactor. After being cooled to room temperature, the product was dissolved in 5 mL ethyl acetate and filtered with diatomite. The filtrate was dried over magnesium sulfate and vacuum concentrated. The concentrate was dissolved in 3 mL of a mixture of trifluoro fluoroacetic acid and methylene:chloride (1:1) and stirred for 12 hours. Neutralization with 10% NaOH, extraction with ethyl acetate, drying with magnesium sulfate and vacuum concentration were sequentially conducted in that order. The residue thus obtained was separated using column chromatography (developing solvent: hexane/ethyl acetate=1/1) to produce 115 mg of 2-[4-(3-chloropyridin-2-yl)phenyl]-6-morpholin-4-yl-1H-benzoimidazole (yield 70%).

$^1$H NMR (CD$_3$OD) δ: 8.64 (d, 1H), 8.18 (d, 2H), 8.10 (d, 1H), 7.87 (d, 2H), 7.66 (d, 1H), 7.61-7.45 (m, 2H), 7.21 (dd, 1H), 3.91-3.87 (m, 4H), 3.32-3.27 (m, 4H)

Examples 18 to 24

The same procedure as in Example 17 was performed to produce Compounds 18 to 24.

| Cpds | Structures | Yields | Spectrum Data (¹H NMR) |
|---|---|---|---|
| 18 | 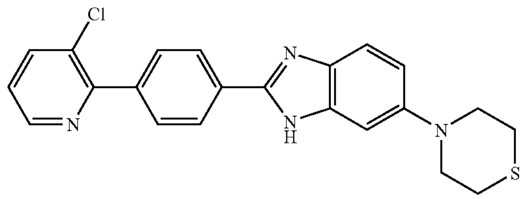 | 65 | (CD$_3$OD) δ: 8.65 (d, 1H), 8.23 (d, 2H), 8.08-8.03 (m, 3H), 7.88 (m, 1H), 7.75 (d, 1H), 7.38 (dd, 1H), 7.23 (d, 1H), 3.70-3.67 (m, 4H), 2.83-2.79 (m, 4H) |
| 19 | 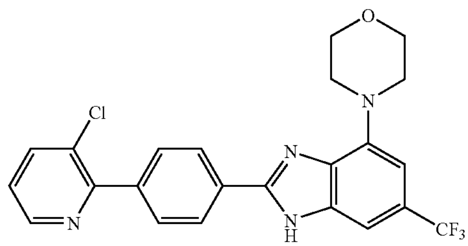 | 59 | (CD$_3$OD) δ: 8.63 (dd, 1H), 8.31 (d, 2H), 8.16 (d, 1H), 7.92 (m, 3H), 7.80 (s, 1H), 7.50-7.48 (m, 1H), 4.01-3.98 (m, 4H), 3.40-3.37 (m, 4H) |
| 20 | 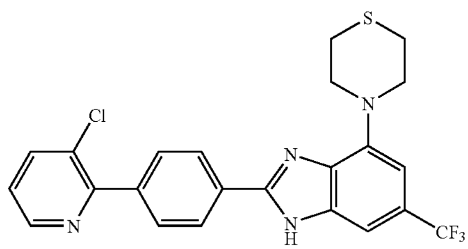 | 63 | (CD$_3$OD) δ: 8.63 (d, 1H), 8.31 (d, 2H), 8.16 (d, 1H), 7.88-7.80 (m, 3H), 7.77 (s, 1H), 7.52-7.47 (m, 1H), 3.69-3.67 (m, 4H), 2.97-2.94 (m, 4H) |
| 21 | 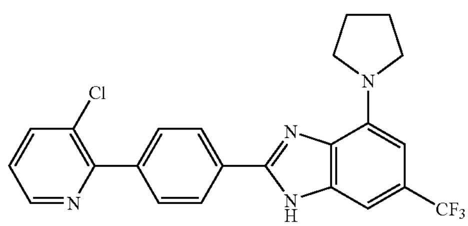 [SMILES: FC(F)(F)c1cc(N2CCCC2)c2nc(-c3ccc(-c4ncccc4Cl)cc3)[nH]c2c1] | 74 | (CD$_3$OD) δ: 8.63 (d, 1H), 8.24 (d, 2H), 8.05 (d, 1H), 7.95-7.92 (m, 3H), 7.49 (m, 1H), 7.34 (s, 1H), 3.81 (m, 4H), 2.17 (m, 4H) |
| 22 | 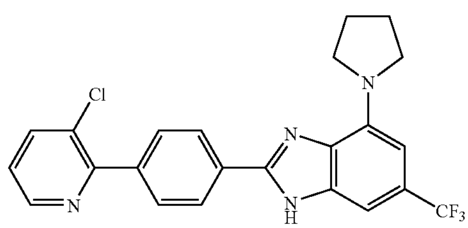 [SMILES: FC(F)(F)c1cc(N2CCCC2)c2nc(-c3ccc(-c4ncccc4Cl)cc3)[nH]c2c1] | 74 | (CD$_3$OD) δ: 8.63 (d, 1H), 8.23 (d, 2H), 8.06 (d, 2H), 7.96-7.93 (m, 2H), 7.49 (m, 1H), 7.34 (s, 1H), 3.05-2.95 (m, 4H), 1.03 (t, 6H) |
| 23 | 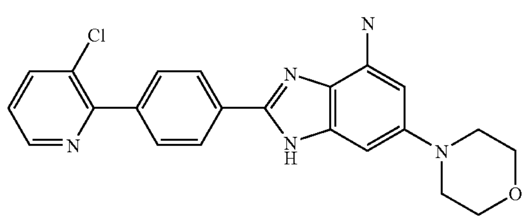 [SMILES: Nc1cc(N2CCOCC2)cc2[nH]c(-c3ccc(-c4ncccc4Cl)cc3)nc12] | 51 | (CD$_3$OD) δ: 8.60 (d, 1H), 8.26 (d, 2H), 8.04 (d, 1H), 7.86 (d, 2H), 7.64 (d, 1H), 7.45-7.39 (m, 2H), 3.82-3.78 (m, 4H), 3.34-3.30 (m, 4H) |
| 24 | 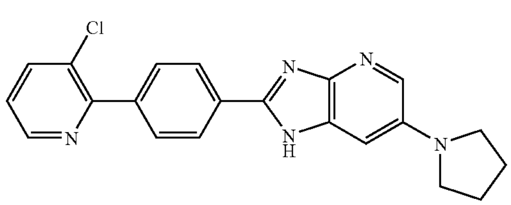 [SMILES: Clc1cccnc1-c1ccc(-c2nc3ncc(N4CCCC4)cc3[nH]2)cc1] | 51 | (CD$_3$OD) δ: 8.61 (d, 1H), 8.25 (d, 2H), 8.03 (d, 1H), 7.85 (d, 2H), 7.64 (d, 1H), 7.44-7.38 (m, 2H), 4.39-4.35 (m, 4H), 2.16-2.05 (m, 4H) |

Example 25

Preparation of 6-tert-butyl-2-[4-(3,5-dichloropyridin-2-yl)phenyl]-1H-benzoimidazole

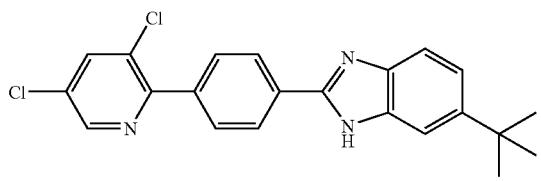 [SMILES: CC(C)(C)c1ccc2nc(-c3ccc(-c4ncc(Cl)cc4Cl)cc3)[nH]c2c1]

(1) Preparation of 4-(3,5-dichloropyridin-2-yl)benzoic acid

The same procedure as in (1) of Example 1 was performed to produce 4-(3,5-dichloropyridin-2-yl)benzoic acid (yield 79%).

$^1$H NMR (CD$_3$OD) δ: 8.74 (s, 1H), 8.27-8.24 (m, 3H), 7.92 (d, 2H)

(2) Preparation of 6-tert-butyl-2-[4-(3,5-dichloropyridin-2-yl)phenyl]-1H-benzoimidazole The same procedure as in (3) of Example 1 was performed to produce 6-tert-butyl-2-[4-(3,5-dichloropyridin-2-yl)phenyl]-1H-benzoimidazole (yield 90%).

$^1$H NMR (CD$_3$OD) δ: 8.62 (s, 1H), 8.20 (d, 2H), 8.15 (s, 1H), 7.88 (d, 2H), 7.64 (s, 1H), 7.56 (s, 1H), 7.41 (d, 1H), 1.42 (s, 9H)

Example 26

Preparation of 2-[4-(3,5-dichloropyridin-2-yl)phenyl]-4,6-bistrifluoromethyl-1H-benzoimidazole

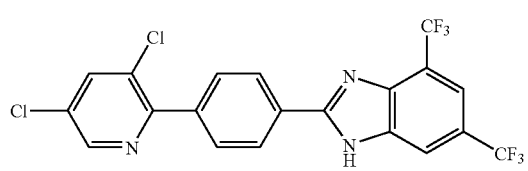

The same procedure as in (2) of Example 25 was performed to produce 2-[4-(3,5-dichloropyridin-2-yl)phenyl]-4,6-bistrifluoromethyl-1H-benzoimidazole (yield 72%).

$^1$H NMR (CD$_3$OD) δ: 8.64 (d, 1H), 8.34 (d, 1H), 8.17-8.10 (m, 2H), 7.94 (d, 2H), 7.87-7.80 (m, 2H)

Example 27

Preparation of 6-tert-butyl-2-[4-(3-chloro-5-trifluoromethylpyridin-2-yl)phenyl]-1H-benzoimidazole

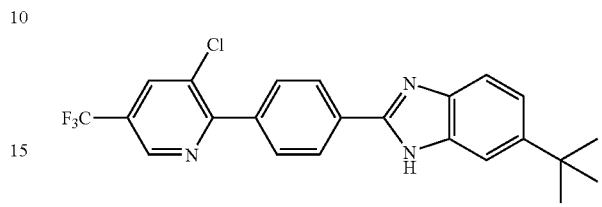

(1) Preparation of 4-(3-chloro-5-trifluoromethylpyridin-2-yl)benzoic acid

The same procedure as in (1) of Example 1 was performed to produce 4-(3-chloro-5-trifluoromethylpyridin-2-yl)benzoic acid (yield 75%).

$^1$H NMR (CD$_3$OD) δ: 9.05 (d, 1H), 8.51 (d, 1H), 8.28 (dd, 2H), 7.97 (dd, 2H)

(2) Preparation of 6-tert-butyl-2-[4-(3-chloro-5-trifluoromethylpyridin-2-yl)phenyl]-1H-benzoimidazole The same procedure as in (3) of Example 1 was performed to produce 6-tert-butyl-2-[4-(3-chloro-5-trifluoromethylpyridin-2-yl)phenyl]-1H-benzoimidazole (yield 87%).

$^1$H NMR (CD$_3$OD) δ: 8.93 (s, 1H), 8.38 (s, 1H), 8.23 (d, 2H), 7.95 (d, 2H), 7.69-7.50 (m, 2H), 7.44-7.39 (m, 1H), 1.42 (s, 9H)

Example 28

Preparation of 2-[4-(3-chloro-5-trifluoromethylpyridin-2-yl)phenyl]-4,6-bistrifluoromethyl-1H-benzoimidazole and 2-[4-(3-chloro-5-trifluoromethylpyridin-2-yl)phenyl]-5,7-bistrifluoromethyl-1H-benzoimidazole

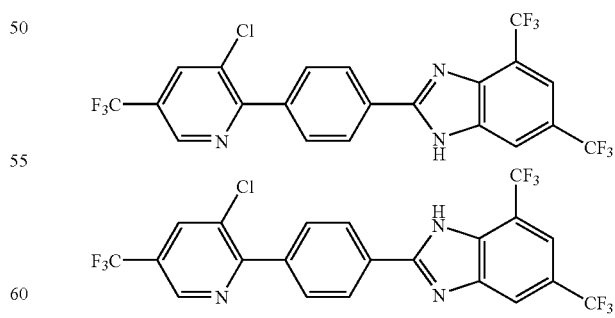

The same procedure as in (2) of Example 27 was performed to produce 2-[4-(3-chloro-5-trifluoromethylpyridin-2-yl)phenyl]-4,6-bistrifluoromethyl-1H-benzoimidazole and 2-[4-(3-chloro-5-trifluoromethylpyridin-2-yl)phenyl]-5,7-bistrifluoromethyl-1H-benzoimidazole (yield 68%).

¹H NMR (CD₃OD) δ: 8.95 (d, 0.7H), 8.92 (d, 0.3H), 8.40-8.35 (m, 2.0H), 8.18 (s, 0.7H), 8.16 (s, 0.3H), 8.01-7.99 (m, 1.0H), 7.94-7.90 (m, 1H), 7.87 (d, 0.3H), 7.85 (d, 0.7H), 7.44 (s, 0.3H), 7.39 (d, 0.7H)

Example 29

Preparation of N-[4'-(4,6-bistrifluoromethyl-1H-benzoimidazole-2-yl)-3-fluorobiphenyl-4-yl]methanesulfonamide

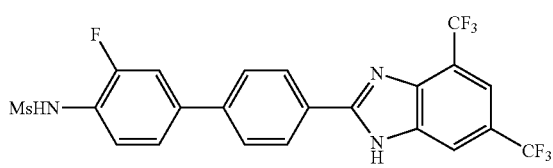

(1) Preparation of 4-(3-fluoro-4-methanesulfonylaminophenyl)benzoic acid

The same procedure as in (1) of Example 1 was performed to produce 4-(3-fluoro-4-methanesulfonylaminophenyl)benzoic acid (yield 58%).

¹H NMR (CD₃OD) δ: 8.22 (dd, 2H), 7.87 (dd, 2H), 7.77-7.64 (m, 3H), 3.18 (s, 3H)

(2) Preparation of N-[4'-(4,6-bistrifluoromethyl-1H-benzoimidazole-2-yl)-3-fluorobiphenyl-4-yl]methanesulfonamide The same procedure as in (3) of Example 1 was performed to produce N-[4'-(4,6-bistrifluoromethyl-1H-benzoimidazole-2-yl)-3-fluorobiphenyl-4-yl]methanesulfonamide (yield 62%).

¹H NMR (CD₃OD) δ: 8.13 (d, 2H), 7.83 (d, 2H), 7.72 (s, 1H), 7.68-7.62 (m, 2H), 7.59-7.55 (m, 2H), 3.07 (s, 3H)

Example 30

Preparation of 6-tert-butyl-2-[4-(3-trifluoromethylpyridin-2-yl)phenyl]-1H-benzoimidazole

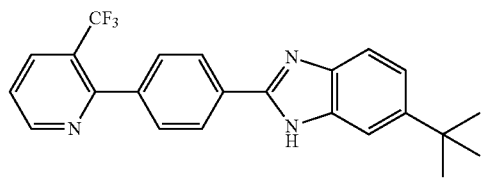 [SMILES: CC(C)(C)c1ccc2nc(-c3ccc(-c4ncccc4C(F)(F)F)cc3)[nH]c2c1]

(1) Preparation of 4-(3-trifluoromethylpyridin-2-yl)benzoic acid

The same procedure as in (1) of Example 1 was performed to produce 4-(3-trifluoromethylpyridin-2-yl)benzoic acid (yield 84%).

¹H NMR (CD₃OD) δ: 8.84 (d, 1H), 8.30 (d, 1H), 8.11 (d, 2H), 7.68-7.64 (m, 1H), 7.56 (d, 2H)

(2) Preparation of 6-tert-butyl-2-[4-(3-trifluoromethylpyridin-2-yl)phenyl]-1H-benzoimidazole The same procedure as in (3) of Example 1 was performed to produce 6-tert-butyl-2-[4-(3-trifluoromethylpyridin-2-yl)phenyl]-1H-benzoimidazole (yield 93%).

¹H NMR (CDCl₃) δ: 8.87 (d, 1H), 8.13 (s, 1H), 8.11 (d, 2H), 7.66 (s, 1H), 7.62 (d, 2H), 7.61 (s, 1H), 7.50-7.47 (m, 1H), 7.36 (d, 1H), 1.39 (s, 9H)

Examples 31 to 40

The same procedure as in (3) of Example 1 was performed to produce compounds 31 to 40.

| Cpds. | Structures | Yield | Spectrum Data (¹H NMR) |
|---|---|---|---|
| 31 | 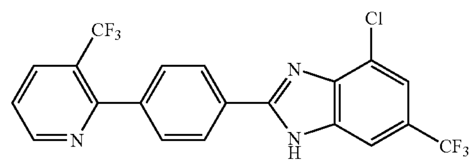 | 77 | (CDCl₃) δ: 8.92 (d, 1H) 8.23 (d, 2H), 8.16 (d, 1H), 8.00 (s, 1H), 7.67 (d, 2H), 7.62 (s, 1H), 7.58-7.52 (m, 1H) |
| 32 | 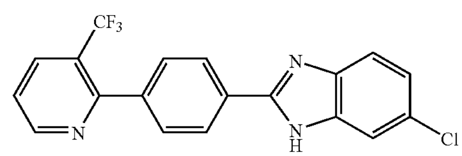 | 88 | (CDCl₃) δ: 8.86 (d, 1H), 8.20-8.11 (m, 3H), 7.70-7.58 (m, 4H), 7.52-7.48 (m, 1H), 7.29-7.27 (m, 1H) |
| 33 | 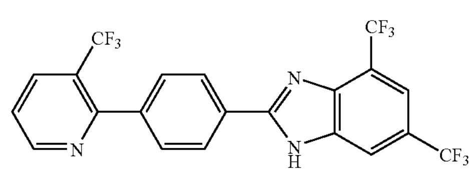 | 75 | (CD₃OD) δ: 8.90 (d, 1H), 8.38 (d, 2H), 8.19 (d, 1H), 7.84 (s, 1H), 7.74 (d, 2H), 7.70-7.65 (m, 2H) |

| Cpds. | Structures | Yield | Spectrum Data ($^1$H NMR) |
|---|---|---|---|
| 34 | 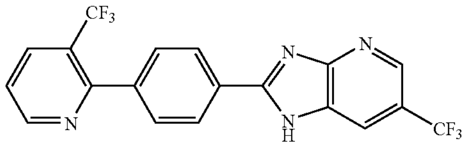 [SMILES: FC(F)(F)c1cnc2nc(-c3ccc(-c4ncccc4C(F)(F)F)cc3)[nH]c2c1] | 63 | (CDCl$_3$) δ: 8.95 (d, 1H) 8.72 (s, 1H), 8.41 (s, 1H), 8.26 (d, 2H), 8.18 (d, 1H), 7.74 (d, 2H), 7.58-7.53 (m, 1H) |
| 35 | 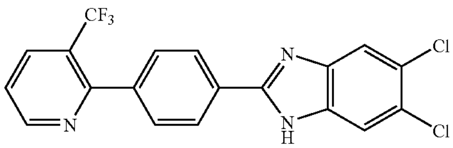 | 92 | (CDCl$_3$) δ: 8.91 (d, 1H), 8.14 (d, 1H), 8.06 (d, 2H), 7.79-7.73 (m, 2H), 7.65 (d, 2H), 7.51 (dd, 1H) |
| 36 | 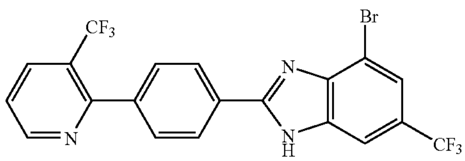 | 76 | (CDCl$_3$) δ: 8.95 (d, 1H), 8.19-8.12 (m, 3H), 7.96 (s, 1H), 7.73 (s, 1H), 7.65 (d, 2H), 7.57-7.53 (m, 1H) |
| 37 | 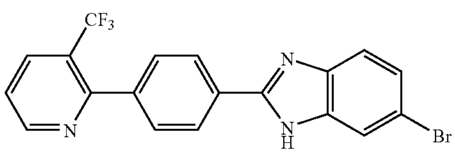 [SMILES: FC(F)(F)c1cccnc1-c1ccc(-c2nc3ccc(Br)cc3[nH]2)cc1] | 72 | (CDCl$_3$) δ: 8.90 (d, 1H) 8.30 (d, 2H), 8.12 (d, 1H), 7.91 (s, 1H), 7.64-7.58 (m, 3H), 7.49 (dd, 1H), 7.43 (dd, 1H) |
| 38 | 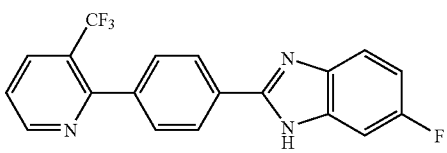 | 93 | (CD$_3$OD) δ: 8.86 (dd, 1H), 8.30 (dd, 1H), 8.19 (dd, 2H), 7.68-7.60 (m, 3H), 7.55 (dd, 1H), 7.32 (dd, 1H), 7.07 (dd, 1H) |
| 39 | 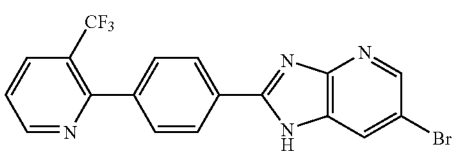 [SMILES: FC(F)(F)c1cccnc1-c1ccc(-c2nc3ncc(Br)cc3[nH]2)cc1] | 61 | (CDCl$_3$) δ: 8.93 (d, 1H) 8.45 (s, 1H), 8.29 (d, 2H), 8.26 (s, 1H), 8.15 (dd, 1H), 7.72 (d, 2H), 7.52 (dd, 1H) |
| 40 | 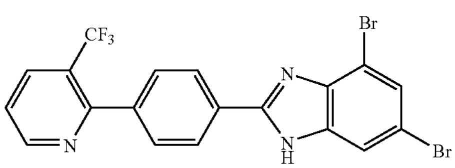 | 65 | (CD$_3$OD) δ: 8.85 (dd, 1H), 8.35-8.25 (m, 3H), 7.73 (br, 1H), 7.69-7.60 (m, 3H), 7.53 (d, 1H) |

Example 41

Preparation of 6-morpholin-4-yl-2-[4-(3-trifluoromethylpyridin-2-yl)phenyl]-1H-benzoimidazole

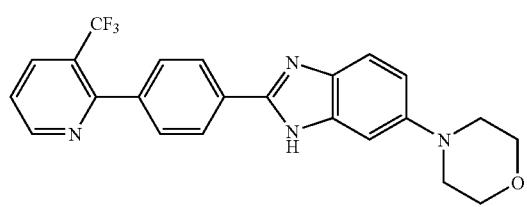

The same procedure as in Example 17 was performed to produce 6-morpholin-4-yl-2-[4-(3-trifluoromethylpyridin-2-yl)phenyl]-1H-benzoimidazole (yield 73%).

$^1$H NMR (CD$_3$OD) δ: 8.85 (d, 1H), 8.32 (dd, 1H), 8.17 (d, 2H), 7.69-7.62 (m, 3H), 7.58 (d, 1H), 7.14 (d, 1H), 7.09 (dd, 1H), 3.83 (dt, 4H), 3.18 (dt, 4H)

Examples 42 to 46

The same procedure as in Example 41 was performed to produce Compounds 42 to 46.

| Cpds. | Structures | Yield | Spectrum Data (¹H NMR) |
|---|---|---|---|
| 42 | 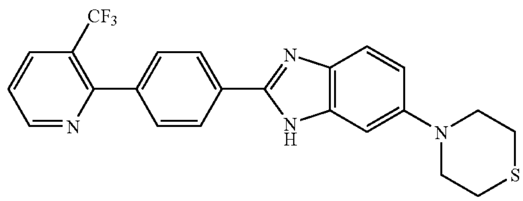 [SMILES: FC(F)(F)c1cccnc1-c1ccc(-c2nc3ccc(N4CCOCC4)cc3[nH]2)cc1] | 72 | (CD$_3$OD) δ: 8.84 (d, 1H), 8.29 (d, 1H), 8.17 (dd, 2H), 7.70-7.62 (m, 3H), 7.53 (d, 1H), 7.16 (d, 1H), 7.05 (dd, 1H), 3.48 (dt, 4H), 2.81 (dt, 4H) |
| 43 | 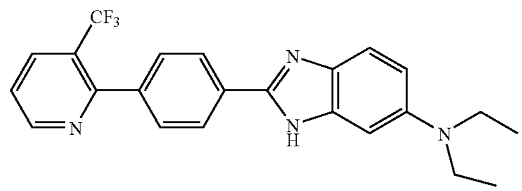 [SMILES: CCN(CC)c1ccc2nc(-c3ccc(-c4ncccc4C(F)(F)F)cc3)[nH]c2c1] | 55 | (CD$_3$OD) δ: 8.84 (d, 1H), 8.32 (dd, 1H), 8.17 (d, 2H), 7.70-7.61 (m, 3H), 7.56 (d, 1H), 7.13 (d, 1H), 7.09 (dd, 1H), 3.11-3.02 (m, 4H), 1.05 (t, 6H) |
| 44 | 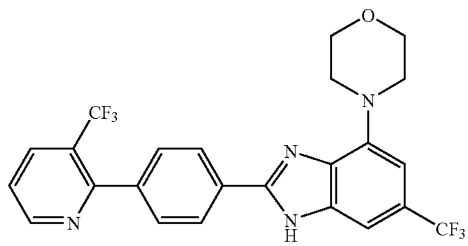 [SMILES: FC(F)(F)c1cc(N2CCOCC2)c2nc(-c3ccc(-c4ncccc4C(F)(F)F)cc3)[nH]c2c1] | 75 | (CDCl$_3$) δ: 8.95 (d, 1H), 8.16 (dd, 1H), 7.98 (d, 2H), 7.59-7.51 (m, 3H), 7.33 (s, 1H), 6.83 (s, 1H), 3.97 (dt, 4H), 3.65 (dt, 4H) |
| 45 | 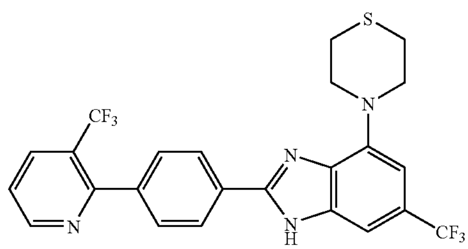 [SMILES: FC(F)(F)c1cc(N2CCSCC2)c2nc(-c3ccc(-c4ncccc4C(F)(F)F)cc3)[nH]c2c1] | 74 | (CDCl$_3$) δ: 8.92 (d, 1H), 8.15 (d, 1H), 8.09 (d, 2H), 7.61-7.51 (m, 3H), 7.45 (s, 1H), 6.97 (s, 1H), 3.90 (br, 4H), 2.90 (br, 4H) |
| 46 | 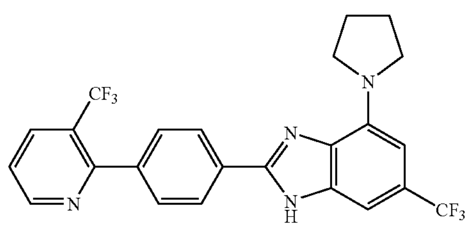 [SMILES: FC(F)(F)c1cc(N2CCCC2)c2nc(-c3ccc(-c4ncccc4C(F)(F)F)cc3)[nH]c2c1] | 69 | (CDCl$_3$) δ: 8.89 (d, 1H), 8.12 (dd, 2H), 8.07 (br, 2H), 7.71 (d, 1H), 7.61 (dd, 2H), 7.49 (dd, 1H), 3.88 (br, 4H), 2.07 (br, 4H) |

Example 47

Preparation of 6-tert-butyl-2-(4-pyridin-2-ylphenyl)-1H-benzoimidazole

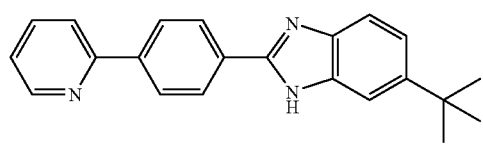

(1) Preparation of 4-(pyridin-2-yl)benzoic acid

The same procedure as in (1) of Example 1 was performed to produce 4-(pyridin-2-yl)benzoic acid (yield 80%).

¹H NMR (CD$_3$OD) δ: 8.66 (d, 1H), 8.14 (d, 2H), 8.07 (d, 2H), 7.94 (d, 2H), 7.43-7.40 (m, 1H)

(2) Preparation of 6-tert-butyl-2-(4-pyridin-2-ylphenyl)-1H-benzoimidazole

The same procedure as in (3) of Example 1 was performed to produce 6-tert-butyl-2-(4-pyridin-2-ylphenyl)-1H-benzoimidazole (yield 84%).

¹H NMR (CD$_3$OD) δ: 8.69 (d, 1H), 8.22 (s, 4H), 7.98 (dd, 2H), 7.69 (d, 1H), 7.64 (d, 1H), 7.55 (dd, 1H), 7.43 (dd, 1H), 1.41 (s, 9H)

Examples 48 to 54

The same procedure as in (2) of Example 47 was performed to produce Compounds 48 to 54.

| Cpds. | Structures | Yield | Spectrum Data ($^1$H NMR) |
|---|---|---|---|
| 48 | 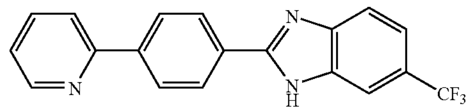 [SMILES: FC(F)(F)c1ccc2nc(-c3ccc(-c4ccccn4)cc3)[nH]c2c1] | 96 | (CD$_3$OD) δ: 8.66 (d, 1H), 8.24 (dd, 2H), 8.19 (dd, 2H), 7.98-7.93 (m, 3H), 7.78 (d, 1H), 7.57 (dd, 1H), 7.42 (dd, 1H) |
| 49 | 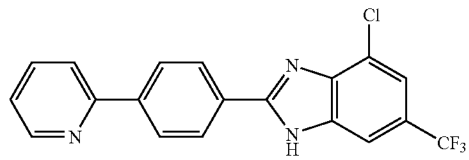 [SMILES: FC(F)(F)c1cc(Cl)c2nc(-c3ccc(-c4ccccn4)cc3)[nH]c2c1] | 88 | (CD$_3$OD) δ: 8.67 (dd, 1H), 8.29 (dd, 2H), 8.19 (dd, 2H), 8.13 (s, 1H), 7.94 (dd, 2H), 7.56 (d, 1H), 7.41 (dd, 1H) |
| 50 | 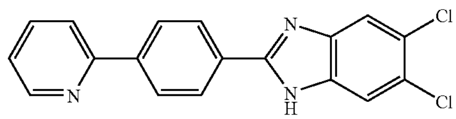 [SMILES: Clc1cc2nc(-c3ccc(-c4ccccn4)cc3)[nH]c2cc1Cl] | 88 | (CD$_3$OD) δ: 8.67 (d, 1H), 8.24-8.16 (m, 4H), 7.97-7.92 (m, 2H), 7.78 (s, 2H), 7.42 (dd, 1H) |
| 51 | 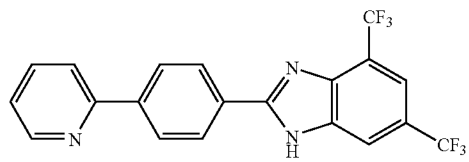 | 61 | (CD$_3$OD) δ: 8.65 (dd, 1H), 8.30 (dd, 2H), 8.15 (dd, 2H), 8.05 (d, 1H), 7.92 (dd, 2H), 7.78 (s, 1H), 7.39 (dd, 1H) |
| 52 | 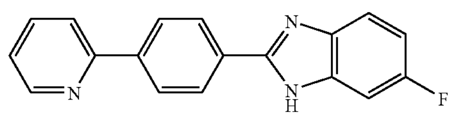 [SMILES: Fc1ccc2nc(-c3ccc(-c4ccccn4)cc3)[nH]c2c1] | 83 | (CD$_3$OD) δ: 8.67 (d, 1H), 8.23-8.15 (m, 4H), 7.97-7.94 (m, 2H), 7.61 (dd, 1H), 7.42 (dd, 1H), 7.33 (dd, 1H), 7.09 (dd, 1H) |
| 53 | 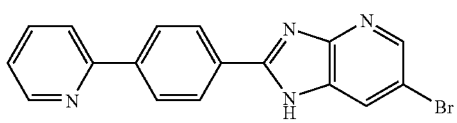 [SMILES: Brc1cnc2nc(-c3ccc(-c4ccccn4)cc3)[nH]c2c1] | 66 | (CD$_3$OD) δ: 8.66 (d, 1H), 8.27 (d, 1H), 8.18-8.12 (m, 3H), 8.07 (d, 2H), 7.95 (dd, 2H), 7.41 (dd, 1H) |
| 54 | 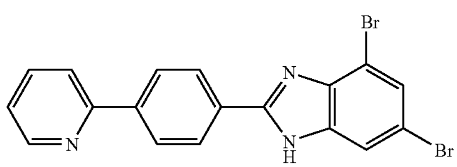 [SMILES: Brc1cc(Br)c2nc(-c3ccc(-c4ccccn4)cc3)[nH]c2c1] | 56 | (CD$_3$OD) δ: 8.55 (dd, 1H), 8.26 (d, 2H), 8.15 (dd, 2H), 7.96-7.90 (m, 2H), 7.68 (s, 1H), 7.58 (d, 1H), 7.41 (dd, 1H) |

Example 55

Preparation of 2-[4-(6-chloro-5-methylpyridazin-3-yl)phenyl]-4,6-bistrifluoromethyl-1H-benzoimidazole ≠ 2-[4-(6-chloro-5-methylpyridazin-3-yl)phenyl]-5,7-bistrifluoromethyl-1H-benzoimidazole

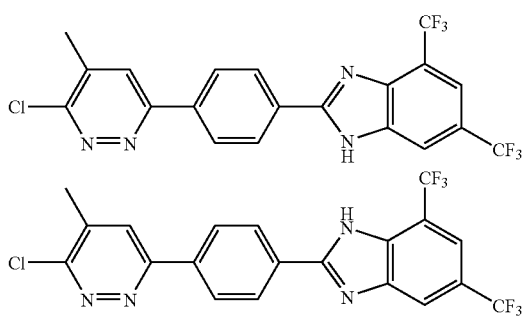

(1) Preparation of 4-(6-chloro-5-methylpyridazin-3-yl)benzoic acid

The same procedure as in (1) of Example 1 was performed to produce 4-(6-chloro-5-methylpyridazin-3-yl)benzoic acid (yield 52%).

$^1$H NMR (CD$_3$OD) δ: 8.20 (s, 1H), 8.20-8.16 (m, 4H), 2.53 (s, 3H)

(2) Preparation of 2-[4-(6-chloro-5-methylpyridazin-3-yl)phenyl]-4,6-bistrifluoromethyl-1H-benzoimidazole and 2-[4-(6-chloro-5-methylpyridazin-3-yl)phenyl]-5,7-bistrifluoromethyl-1H-benzoimidazole The same procedure as in (3) of Example 1 was performed to produce 2-[4-(6-chloro-5-methylpyridazin-3-yl)phenyl]-4,6-bistrifluoromethyl-1H-benzoimidazole and 2-[4-(6-chloro-5-methylpyridazin-3-yl)phenyl]-5,7-bistrifluoromethyl-1H-benzoimidazole (yield 71%).

$^1$H NMR (CD$_3$OD) δ: 8.89 (d, 0.5H), 8.64 (d, 0.5H), 8.45-8.37 (m, 2.5H), 8.33-8.15 (m, 2.5H), 7.70-7.60 (m, 1.0H), 2.75 (s, 1.5H), 2.54 (s, 1.5H)

Example 56

Preparation of 4-bromo-6-(trifluoromethyl)-2-(4-(4-(trifluoromethyl)pyrimidin-2-yl)phenyl)-1H-benzoimidazole

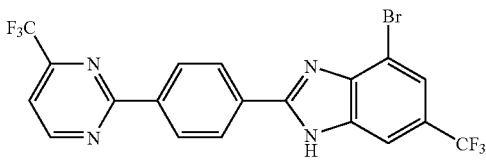 [SMILES: FC(F)(F)c1cc(Br)c2nc(-c3ccc(-c4nccc(C(F)(F)F)n4)cc3)[nH]c2c1]

(1) Preparation of 4-(4-trifluoromethylpyrimidin-2-yl)benzoic acid

The same procedure as in (1) of Example 1 was performed to produce 4-(4-trifluoromethylpyrimidin-2-yl)benzoic acid (yield 77%).

$^1$H NMR (CD$_3$OD) δ: 9.20 (d, 1H), 8.62 (dd, 2H), 8.19 (dd, 2H), 7.81 (d, 1H)

(2) Preparation of 4-bromo-6-(trifluoromethyl)-2-(4-(4-(trifluoromethyl)pyrimidin-2-yl)phenyl)-1H-benzoimidazole The same procedure as in (3) of Example 1 was performed to produce 4-bromo-6-(trifluoromethyl)-2-(4-(4-(trifluoromethyl)pyrimidin-2-yl)phenyl)-1H-benzoimidazole (yield 72%).

$^1$H NMR (CDCl$_3$) δ: 9.14 (d, 1H), 8.74 (d, 2H), 8.27 (d, 2H), 8.00 (s, 1H), 7.76 (s, 1H), 7.62 (d, 1H)

Example 57

Preparation of 4,6-dibromo-2-[4-(4-trifluoromethylpyrimidin-2-yl)phenyl]-1H-benzoimidazole

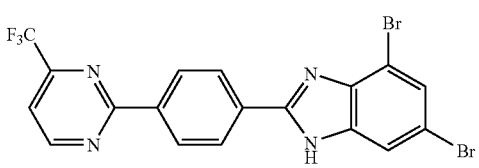 [SMILES: FC(F)(F)c1ccnc(-c2ccc(-c3nc4c(Br)cc(Br)cc4[nH]3)cc2)n1]

The same procedure as in (2) of Example 56 was performed to produce 4,6-dibromo-2-[4-(4-trifluoromethylpyrimidin-2-yl)phenyl]-1H-benzoimidazole (yield 64%).

$^1$H NMR (CD$_3$OD) δ: 9.18 (d, 1H), 8.70 (dd, 1H), 8.56 (d, 2H), 8.36 (dd, 1H), 8.26 (s, 1H), 8.15 (d, 2H)

Example 58

Preparation of 6-tert-butyl-2-(4-(pyrimidin-2-yl)phenyl)-1H-benzoimidazole

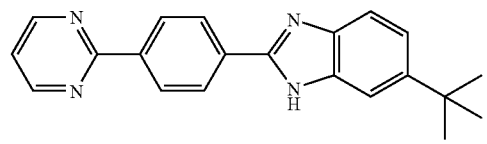

(1) Preparation of 4-(pyrimidin-2-yl)benzoic acid

The same procedure as in (1) of Example 1 was performed to produce 4-(pyrimidin-2-yl)benzoic acid (yield 74%).

$^1$H NMR (CD$_3$OD) δ: 8.88 (d, 2H), 8.47 (d, 2H), 8.12 (d, 2H), 7.39 (t, 1H)

(2) Preparation of 6-tert-butyl-2-(4-(pyrimidin-2-yl)phenyl)-1H-benzoimidazole

The same procedure as in (3) of Example 1 was performed to produce 6-tert-butyl-2-(4-(pyrimidin-2-yl)phenyl)-1H-benzoimidazole (yield 92%).

$^1$H NMR (CD$_3$OD) δ: 8.88 (d, 2H), 8.58 (dd, 2H), 8.21 (dd, 2H), 7.64 (d, 1H), 7.56 (d, 1H), 7.42-7.37 (m, 2H), 1.41 (s, 9H)

Example 59

Preparation of 2-(4-(6-(trifluoromethyl)-1H-benzoimidazole-2-yl)phenyl)pyridin-3-carbonitrile

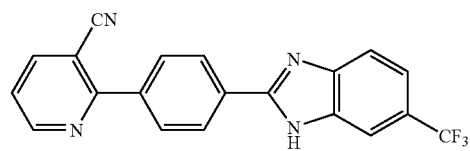

(1) Preparation of 4-(3-cyanopyridin-2-yl)benzoic acid

The same procedure as in (1) of Example 1 was performed to produce 4-(3-cyanopyridin-2-yl)benzoic acid (yield 59%).

$^1$H NMR (CD$_3$OD) δ: 9.04 (dd, 1H), 8.46 (dd, 1H), 8.32 (d, 2H), 8.12 (d, 2H), 7.74 (dd, 1H)

(2) Preparation of 2-(4-(6-(trifluoromethyl)-1H-benzoimidazole-2-yl)phenyl)pyridin-3-carbonitrile The same procedure as in (3) of Example 1 was performed to produce 2-(4-(6-(trifluoromethyl)-1H-benzoimidazole-2-yl)phenyl)pyridin-3-carbonitrile (yield 76%).

$^1$H NMR (CD$_3$OD) δ: 8.89 (dd, 1H), 8.32-8.26 (m, 3H), 8.08 (dd, 2H), 7.90 (s, 1H), 7.75 (d, 1H), 7.60-7.53 (m, 2H)

Examples 60 and 61

The same procedure as in (2) of Example 59 was performed to produce Compounds 60 and 61.

| Cpds. | Structures | Yield | Spectrum Data (¹H NMR) |
|---|---|---|---|
| 60 | 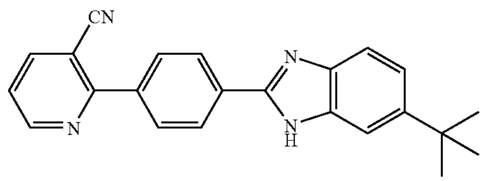 [SMILES: CC(C)(C)c1ccc2nc(-c3ccc(-c4ncccc4C#N)cc3)[nH]c2c1] | 82 | (CD$_3$OD) δ: 8.89 (dd, 1H), 8.30 (dd, 1H), 8.25 (d, 2H), 8.07 (d, 2H), 7.64 (d, 1H), 7.59-7.55 (m, 2H), 7.42 (dd, 1H), 1.41 (s, 9H) |
| 61 | 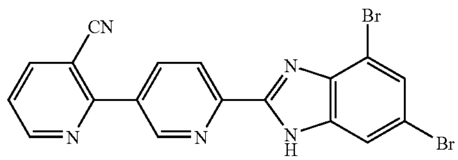 | 55 | (CD$_3$OD) δ: 8.88 (d, 1H), 8.31 (dd, 1H), 7.98 (d, 2H), 7.75 (d, 2H), 7.57 (dd, 1H), 7.53 (d, 1H), 7.50 (d, 1H) |

Example 62

Preparation of 2-[4-(3-chloropyrazin-2-yl)phenyl]-6-trifluoromethyl-1H-benzoimidazole

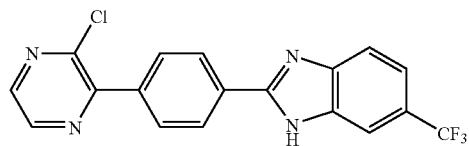 [SMILES: FC(F)(F)c1ccc2nc(-c3ccc(-c4nccnc4Cl)cc3)[nH]c2c1]

(1) Preparation of 4-(3-chloropyrazin-2-yl)benzoic acid

The same procedure as in (1) of Example 1 was performed to produce 4-(3-chloropyrazin-2-yl)benzoic acid (yield 79%).

¹H NMR (CD$_3$OD) δ: 8.72 (d, 1H), 8.50 (d, 1H), 8.20 (d, 2H), 7.93 (d, 2H)

(2) Preparation of 2-[4-(3-chloropyrazin-2-yl)phenyl]-6-trifluoromethyl-1H-benzoimidazole The same procedure as in (3) of Example 1 was performed to produce 2-[4-(3-chloropyrazin-2-yl)phenyl]-6-trifluoromethyl-1H-benzoimidazole (yield 96%).

¹H NMR (CDCl$_3$) δ: 8.62 (d, 1H), 8.39 (d, 1H), 8.20 (d, 2H), 7.99 (s, 1H), 7.97 (d, 2H), 7.71 (s, 1H), 7.52 (dd, 1H)

Examples 63 and 66

The same procedure as in (2) of Example 62 was performed to produce Compounds 63 to 66.

| Cpds. | Structures | Yield | Spectrum Data (¹H NMR) |
|---|---|---|---|
| 63 | 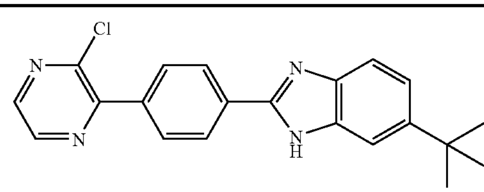 | 91 | (CDCl$_3$) δ: 8.58 (d, 1H), 8.35 (d, 1H), 8.21 (d, 2H), 7.91 (d, 2H), 7.66 (s, 1H), 7.58 (d, 1H), 7.36 (dd, 1H), 1.36 (s, 9H) |
| 64 | 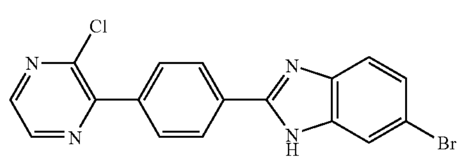 [SMILES: Clc1nccnc1-c1ccc(-c2nc3ccc(Br)cc3[nH]2)cc1] | 69 | (CDCl$_3$) δ: 8.62 (d, 1H), 8.40 (dd, 1H), 8.15 (dd, 2H), 7.99 (dd, 2H), 7.80 (s, 1H), 7.50 (s, 1H), 7.40 (dd, 1H) |
| 65 | 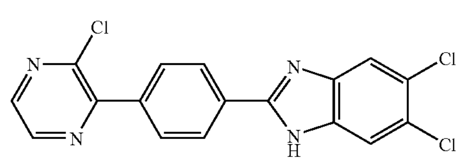 | 88 | (CDCl$_3$) δ: 8.62 (d, 1H), 8.40 (dd, 1H), 8.12 (dd, 2H), 7.98 (dd, 2H), 7.92 (dd, 1H), 7.67 (s, 1H) |

| Cpds. | Structures | Yield | Spectrum Data ($^1$H NMR) |
|---|---|---|---|
| 66 | 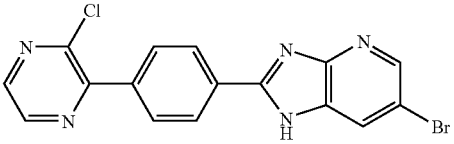 | 58 | (CDCl$_3$) δ: 8.60 (d, 1H), 8.37 (d, 1H), 8.09 (dd, 1H), 7.84 (dd, 2H), 7.51 (dd, 1H), 7.44 (dd, 2H) |

Example 67

Preparation of 6-tert-butyl-2-[4-(3-chloropyridin-2-yl)-2-fluorophenyl]-1H-benzoimidazole

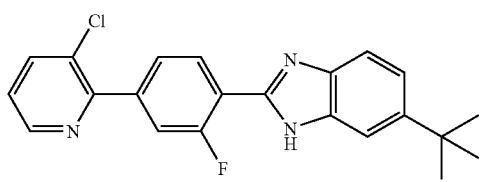

(1) Preparation of 4-(3-chloropyridin-2-yl)-2-fluorobenzoic acid

The same procedure as in (1) of Example 1 was performed to produce 4-(3-chloropyridin-2-yl)-2-fluorobenzoic acid (yield 77%).

$^1$H NMR (CD$_3$OD) δ: 8.51 (d, 1H), 7.99-7.93 (m, 2H), 7.52-7.48 (m, 2H), 7.42-7.36 (m, 1H), 1.42 (s, 9H)

(2) Preparation of 6-tert-butyl-2-[4-(3-chloropyridin-2-yl)-2-fluorophenyl]-1H-benzoimidazole The same procedure as in (3) of Example 1 was performed to produce 6-tert-butyl-2-[4-(3-chloropyridin-2-yl)-2-fluorophenyl]-1H-benzoimidazole (yield 91%).

$^1$H NMR (CD$_3$OD) δ: 8.62 (d, 1H), 8.05 (dd, 1H), 8.03 (d, 1H), 7.74-7.70 (m, 2H), 7.66 (s, 1H), 7.47-7.43 (m, 2H)

Examples 68 and 69

The same procedure as in (2) of Example 27 was performed to produce Compounds 68 and 69.

| Cpds. | Structures | Yield | Spectrum Data ($^1$H NMR) |
|---|---|---|---|
| 68 | 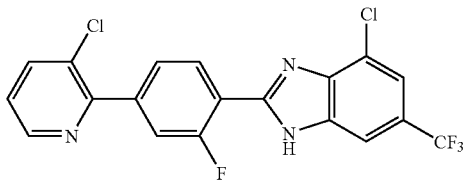 | 69 | (CD$_3$OD) δ: 8.62 (d, 1H), 8.50-8.45 (m, 1H), 8.05 (d, 1H), 7.92 (s, 1H), 7.79-7.70 (m, 2H), 7.61 (s, 1H), 7.50-7.45 (m, 1H) |
| 69 | 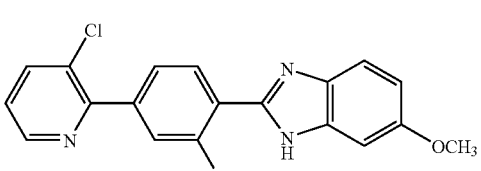 | 93 | (CD$_3$OD) δ: 8.62 (d, 1H), 8.28 (dd, 1H), 8.05 (d, 1H), 7.73 (d, 1H), 7.66 (s, 1H), 7.56-7.52 (m, 1H), 7.49-7.45 (m, 1H), 7.10 (s, 1H), 6.96 (dd, 1H), 3.88 (s, 3H) |

Example 70

Preparation of 6-tert-butyl-2-[4-(3,5-dichloropyridin-2-yl)-2-fluorophenyl]-1H-benzoimidazole

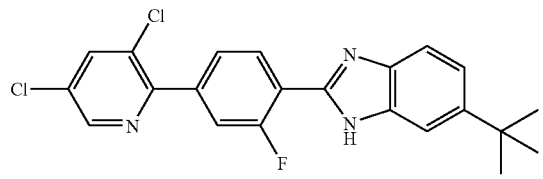

(1) Preparation of 4-(3,5-dichloropyridin-2-yl)-2-fluorobenzoic acid

The same procedure as in (1) of Example 1 was performed to produce 4-(3,5-dichloropyridin-2-yl)-2-fluorobenzoic acid (yield 69%).
$^1$H NMR (CD$_3$OD) δ: 8.55 (s, 1H), 8.07 (s, 1H), 7.93 (dd, 1H), 7.59-7.52 (m, 2H)

(2) Preparation of 6-tert-butyl-2-[4-(3,5-dichloropyridin-2-yl)-2-fluorophenyl]-1H-benzoimidazole The same procedure as in (3) of Example 1 was performed to produce 6-tert-butyl-2-[4-(3,5-dichloropyridin-2-yl)-2-fluorophenyl]-1H-benzoimidazole (yield 88%).
$^1$H NMR (CD$_3$OD) δ: 8.64 (s, 1H), 8.27 (d, 1H), 8.16 (s, 1H), 77.72-7.68 (m, 3H), 7.60 (d, 1H), 7.45 (d, 1H), 1.42 (s, 9H)

Examples 71 and 72

The same procedure as in (2) of Example 70 was performed to produce Compounds 71 and 72.

Example 73

Preparation of 4-chloro-2-[4-(3-chloro-5-trifluoromethylpyridin-2-yl)-2-fluorophenyl]-6-trifluoromethyl-1H-benzoimidazole

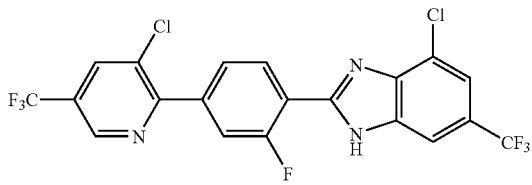

(1) Preparation of 4-(3-chloro-5-trifluoromethylpyridin-2-yl)-2-fluorobenzoic acid The same procedure as in (1) of Example 1 was performed to produce 4-(3-chloro-5-trifluoromethylpyridin-2-yl)-2-fluorobenzoic acid (yield 72%).
$^1$H NMR (CD$_3$OD) δ: 8.85 (d, 1H), 8.31 (d, 1H), 7.98 (dd, 1H), 7.60-7.51 (m, 2H)

(2) Preparation of 4-chloro-2-[4-(3-chloro-5-trifluoromethylpyridin-2-yl)-2-fluorophenyl]-6-trifluoromethyl-1H-benzoimidazole The same procedure as in (3) of Example 1 was performed to produce 4-chloro-2-[4-(3-chloro-5-trifluoromethylpyridin-2-yl)-2-fluorophenyl]-6-trifluoromethyl-1H-benzoimidazole (yield 81%).
$^1$H NMR (CD$_3$OD) δ: 8.96 (s, 1H), 8.42 (s, 2H), 7.92 (s, 1H), 7.88-7.82 (m, 2H), 7.62 (s, 1H)

| Cpds. | Structures | Yield | Spectrum Data ($^1$H NMR) |
|---|---|---|---|
| 71 | 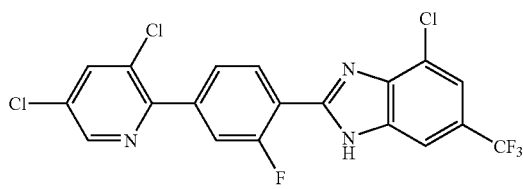 | 57 | (CD$_3$OD) δ: 8.65 (s, 1H), 8.45-8.39 (m, 1H), 8.18 (s, 1H), 7.91 (s, 1H), 7.85-7.78 (m, 2H), 7.61 (s, 1H) |
| 72 | 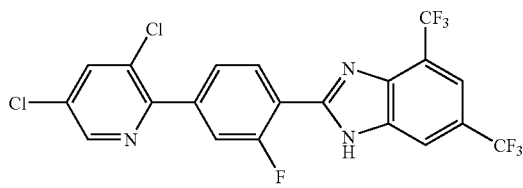 | 75 | (CD$_3$OD) δ: 8.66 (s, 1H), 8.65-8.49 (m, 1H), 8.20-8.15 (m, 2H), 7.82-7.74 (m, 3H) |

Examples 74 and 75

The same procedure as in (2) of Example 73 was performed to produce Compounds 74 and 75.

| pds. | Structures | yield | Spectrum Data ($^1$H NMR) |
|---|---|---|---|
| 74 | 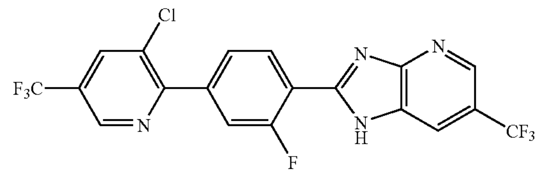 [SMILES: Fc1cc(-c2ncc(C(F)(F)F)cc2Cl)ccc1-c1nc2ncc(C(F)(F)F)cc2[nH]1] | 59 | (CD$_3$OD) δ: 8.97 (s, 1H), 8.76 (s, 1H), 8.43 (d, 2H), 8.36 (s, 1H), 7.89-7.83 (m, 2H) |
| 75 | 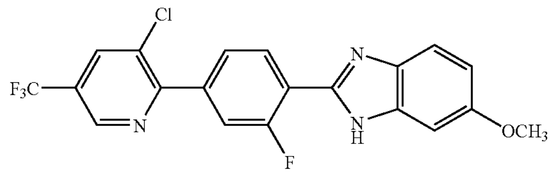 [SMILES: COc1ccc2nc(-c3ccc(-c4ncc(C(F)(F)F)cc4Cl)cc3F)[nH]c2c1] | 90 | (CD$_3$OD) δ: 8.95 (s, 1H), 8.41 (s, 1H), 8.31-8.27 (m, 1H), 7.83-7.78 (m, 2H), 7.57 (d, 1H), 7.16 (d, 1H), 6.95 (d, 1H), 3.88 (s, 3H) |

Example 76

Preparation of N-[3,3'-difluoro-4'-(6-methoxy-1H-benzoimidazole-2-yl)biphenyl-4-yl]methanesulfonamide

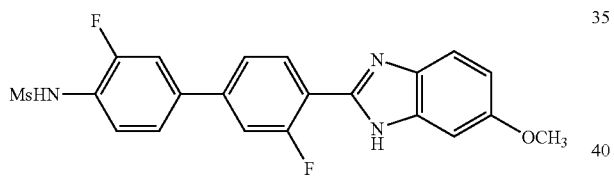

(1) Preparation of 4-(3-fluoro-4-methanesulfonylaminophenyl)-2-fluorobenzoic acid The same procedure as in (1) of Example 1 was performed to produce 4-(3-fluoro-4-methanesulfonylaminophenyl)-2-fluorobenzoic acid (yield 52%).

$^1$H NMR (CD$_3$OD) δ: 7.94-7.91 (m, 1H), 7.56-7.52 (m, 2H), 7.49-7.41 (m, 3H), 2.98 (s, 3H)

(2) Preparation of N-[3,3'-difluoro-4'-(6-methoxy-1H-benzoimidazole-2-yl)biphenyl-4-yl]methanesulfonamide The same procedure as in (3) of Example 1 was performed to produce N-[3,3'-difluoro-4'-(6-methoxy-1H-benzoimidazole-2-yl)biphenyl-4-yl]methanesulfonamide (yield 55%).

$^1$H NMR (CD$_3$OD) δ: 7.73 (d, 1H), 7.71 (d, 1H), 7.58 (s, 1H), 7.55-7.52 (m, 3H), 7.50-7.48 (m, 1H), 7.28-7.25 (m, 1H), 6.85 (d, 1H), 3.86 (s, 3H), 2.99 (s, 3H)

Example 77

Preparation of 2-[2-fluoro-4-(3-trifluoromethylpyridin-2-yl)phenyl]-6-trifluoromethyl-1H-benzoimidazole

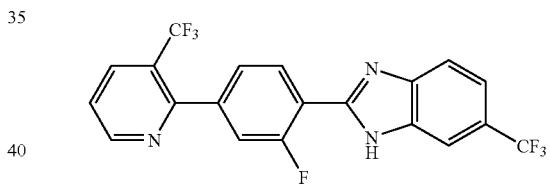

(1) Preparation of 2-fluoro-4-(3-trifluoromethylpyridin-2-yl)benzoic acid

The same procedure as in (1) of Example 1 was performed to produce 2-fluoro-4-(3-trifluoromethylpyridin-2-yl)benzoic acid (yield 71%).

$^1$H NMR (CD$_3$OD) δ: 8.85 (d, 1H), 8.30 (d, 1H), 8.00 (dd, 1H), 7.68 (dd, 1H), 7.38-7.31 (m, 2H)

(2) Preparation of 2-[2-fluoro-4-(3-trifluoromethylpyridin-2-yl)phenyl]-6-trifluoromethyl-1H-benzoimidazole The same procedure as in (3) of Example 1 was performed to produce 2-[2-fluoro-4-(3-trifluoromethylpyridin-2-yl)phenyl]-6-trifluoromethyl-1H-benzoimidazole (yield 83%).

$^1$H NMR (CD$_3$OD) δ: 8.89 (d, 1H), 8.36-8.32 (m, 2H), 8.00 (s, 1H), 7.83 (d, 1H), 7.72-7.68 (m, 1H), 7.60 (d, 1H), 7.55 (s, 1H), 7.52 (d, 1H)

Examples 78 and 80

The same procedure as in (2) of Example 77 was performed to produce Compounds 78 to 80.

| Cpds. | Structures | Yield | Spectrum Data ($^1$H NMR) |
|---|---|---|---|
| 78 | 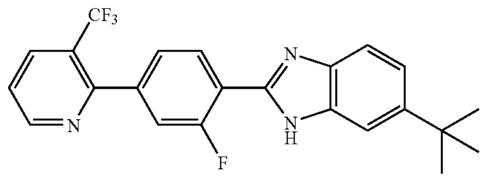 [SMILES: CC(C)(C)c1ccc2nc(-c3ccc(-c4ncccc4C(F)(F)F)cc3F)[nH]c2c1] | 94 | (CD$_3$OD) δ: 8.88 (d, 1H), 8.34-8.26 (m, 2H), 7.70-7.65 (m, 2H), 7.61 (d, 1H), 7.51-7.42 (m, 3H), 1.43 (s, 9H) |
| 79 | 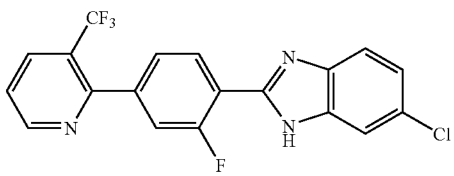 [SMILES: Fc1cc(-c2ncccc2C(F)(F)F)ccc1-c1nc2ccc(Cl)cc2[nH]1] | 89 | (CD$_3$OD) δ: 8.89 (d, 0.6H), 8.84 (d, 0.4H), 8.47-8.43 (m, 0.6H), 8.35-8.28 (m, 1.0H), 8.25-8.20 (m, 0.4H), 7.95-7.88 (m, 1.6H), 7.73-7.42 (m, 3.0H), 7.42 (d, 0.4H), 7.34-7.26 (m, 1.0H) |
| 80 | 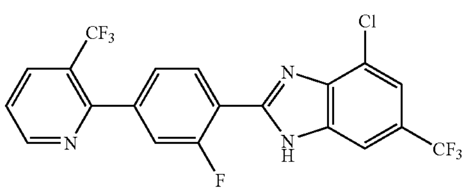 [SMILES: Fc1cc(-c2ncccc2C(F)(F)F)ccc1-c1nc2c(Cl)cc(C(F)(F)F)cc2[nH]1] | 67 | (CD$_3$OD) δ: 8.89 (d, 0.6H), 8.84 (d, 0.4H), 8.49-8.45 (m, 0.6H), 8.35-8.30 (m, 1.0H), 7.95-7.90 (m, 1.0H), 7.68-7.41 (m, 3.4H), 7.33-7.26 (m, 1.0H) |

Example 81

Preparation of 2-(2-fluoro-4-pyridin-2-yl)phenyl]-6-trifluoromethyl-1H-benzoimidazole

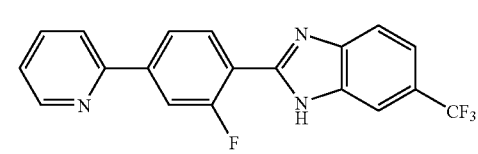

(1) Preparation of 2-fluoro-4-pyridin-2-ylbenzoic acid

The same procedure as in (1) of Example 1 was performed to produce 2-fluoro-4-pyridin-2-ylbenzoic acid (yield 69%).
$^1$H NMR (CD$_3$OD) δ: 7.79-7.74 (m, 2H), 7.46-7.34 (m, 3H), 7.11-7.02 (m, 2H)

(2) Preparation of 2-(2-fluoro-4-pyridin-2-yl)phenyl]-6-trifluoromethyl-1H-benzoimidazole The same procedure as in (3) of Example 1 was performed to produce 2-(2-fluoro-4-pyridin-2-yl)phenyl]-6-trifluoromethyl-1H-benzoimidazole (yield 82%).

$^1$H NMR (CDCl$_3$) δ: 8.77-8.71 (m, 1H), 8.06-7.90 (m, 3H), 7.89-7.83 (m, 2H), 7.62-7.51 (m, 4H)

Examples 82 and 84

The same procedure as in (2) of Example 81 was performed to produce Compounds 82 to 84.

| Cpds. | Structures | Yield | Spectrum Data ($^1$H NMR) |
|---|---|---|---|
| 82 | 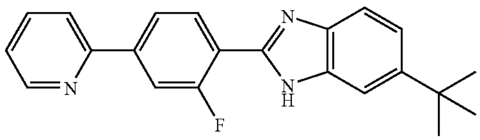 | 88 | (CDCl$_3$) δ: 8.90 (d, 1H), 8.65 (d, 1H), 7.92-7.80 (m, 6H), 7.52 (d, 2H), 1.25 (s, 9H) |
| 83 | 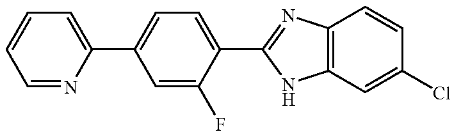 [SMILES: Fc1cc(-c2ccccn2)ccc1-c1nc2ccc(Cl)cc2[nH]1] | 79 | (CDCl$_3$) δ: 8.74 (d, 1H), 8.02-7.97 (m, 2H), 7.88-7.82 (m, 2H), 7.70-7.65 (m, 1H), 7.34-7.27 (m, 4H) |
| 84 | 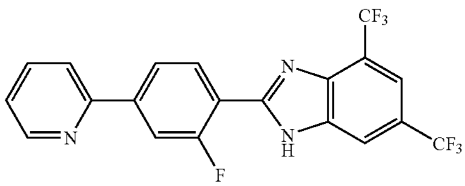 [SMILES: Fc1cc(-c2ccccn2)ccc1-c1nc2c(C(F)(F)F)cc(C(F)(F)F)cc2[nH]1] | 72 | (CDCl$_3$) δ: 8.22-8.18 (m, 1H), 8.08-8.04 (m, 1H), 7.82-7.79 (m, 1H), 7.63 (s, 1H), 7.55 (d, 1H), 7.39-7.26 (m, 4H) |

Example 85

Preparation of 2-[2-chloro-4-(3-chloropyridin-2-yl) phenyl]-6-trifluoromethyl-1H-benzoimidazole

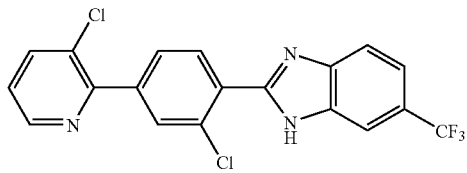

(1) Preparation of 2-chloro-4-(3-chloropyridin-2-yl)benzoic acid

The same procedure as in (1) of Example 1 was performed to produce 2-chloro-4-(3-chloropyridin-2-yl)benzoic acid (yield 80%).

$^1$H NMR (CD$_3$OD) δ: 8.60-8.58 (m, 1H), 8.02 (dd, 1H), 7.95 (d, 1H), 7.79 (d, 1H), 7.69 (dd, 1H), 7.48-7.44 (m, 1H)

(2) Preparation of 2-[2-chloro-4-(3-chloropyridin-2-yl)phenyl]-6-trifluoromethyl-1H-benzoimidazole The same procedure as in (3) of Example 1 was performed to produce 2-[2-chloro-4-(3-chloropyridin-2-yl)phenyl]-6-trifluoromethyl-1H-benzoimidazole (yield 91%).

$^1$H NMR (CD$_3$OD) δ: 8.63 (d, 1H), 8.05-7.98 (m, 3H) 7.95 (s, 1H), 7.85 (d, 1H), 7.82 (s, 1H), 7.60 (d, 1H), 7.48-7.44 (m, 1H)

Examples 86 and 87

The same procedure as in (2) of Example 85 was performed to produce Compounds 86 and 87.

| Cpds. | Structures | Yield | Spectrum Data ($^1$H NMR) |
|---|---|---|---|
| 86 | 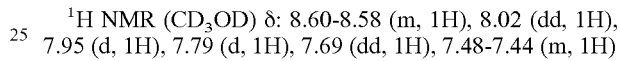 | 79 | (CDCl$_3$) δ: 8.78 (d, 1H), 8.25 (s, 1H), 8.22-8.17 (m, 1H), 7.98 (s, 1H), 7.97-7.92 (m, 2H), 7.77 (s, 1H), 7.60-7.55 (m, 1H) |
| 87 | 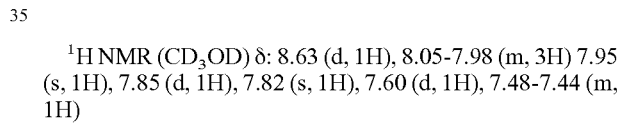 | 58 | (CDCl$_3$) δ: 8.77 (s, 1H), 8.68-8.65 (m, 1H), 8.49 (s, 1H), 7.99-7.89 (m, 4H), 7.45-7.38 (m, 1H) |

Example 88

Preparation of 2-[2-chloro-4-(3,5-dichloropyridin-2-yl)phenyl]-6-trifluoromethyl-1H-benzoimidazole

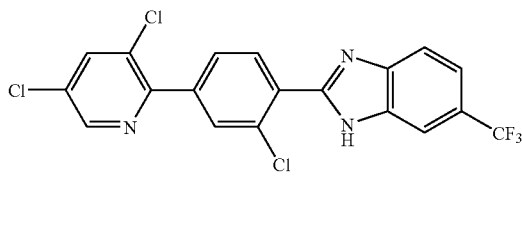

(1) Preparation of 2-chloro-4-(3,5-dichloropyridin-2-yl)benzoic acid

The same procedure as in (1) of Example 1 was performed to produce 2-chloro-4-(3,5-dichloropyridin-2-yl)benzoic acid (yield 72%).

$^1$H NMR (CD$_3$OD) δ: 8.62 (d, 1H), 8.15 (d, 1H), 7.93 (d, 1H), 7.82 (d, 1H), 7.72 (dd, 1H)

(2) Preparation of 2-[2-chloro-4-(3,5-dichloropyridin-2-yl)phenyl]-6-trifluoromethyl-1H-benzoimidazole The same procedure as in (3) of Example 1 was performed to produce 2-[2-chloro-4-(3,5-dichloropyridin-2-yl)phenyl]-6-trifluoromethyl-1H-benzoimidazole (yield 88%).

$^1$H NMR (CD$_3$OD) δ: 8.63 (d, 1H), 8.16 (d, 1H), 8.03-7.95 (m, 3H), 7.87-7.82 (m, 2H), 7.59 (d, 1H)

Examples 89 and 91

The same procedure as in (2) of Example 88 was performed to produce Compounds 89 to 91.

Example 92

Preparation of 2-[2-chloro-4-(3-chloro-5-trifluoromethylpyridin-2-yl)phenyl]-6-trifluoromethyl-1H-benzoimidazole

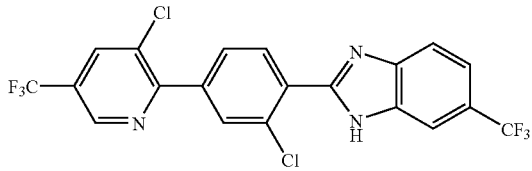

(1) Preparation of 2-chloro-4-(3-chloro-5-trifluoromethylpyridin-2-yl)benzoic acid The same procedure as in (1) of Example 1 was performed to produce 2-chloro-4-(3-chloro-5-trifluoromethylpyridin-2-yl)benzoic acid (yield 68%).

$^1$H NMR (CD$_3$OD) δ: 8.92 (d, 1H), 8.38 (d, 1H), 7.96 (d, 1H), 7.87 (d, 1H), 7.77 (dd, 1H)

(2) Preparation of 2-[2-chloro-4-(3-chloro-5-trifluoromethylpyridin-2-yl)phenyl]-6-trifluoromethyl-1H-benzoimidazole The same procedure as in (3) of Example 1 was performed to produce 2-[2-chloro-4-(3-chloro-5-trifluoromethylpyridin-2-yl)phenyl]-6-trifluoromethyl-1H-benzoimidazole (yield 88%).

| Cpds. | Structures | Yield | Spectrum Data ($^1$H NMR) |
|---|---|---|---|
| 89 | 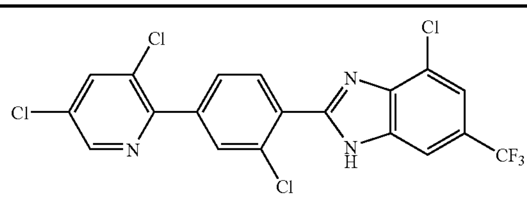 | 76 | (CDCl$_3$) δ: 8.61-8.58 (m, 2H), 8.03 (s, 1H), 7.93-7.87 (m, 3H), 7.64 (s, 1H) |
| 90 | 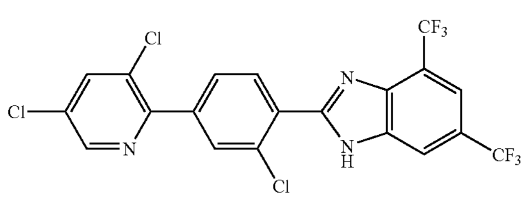 [SMILES: FC(F)(F)c1cc(C(F)(F)F)c2nc(-c3ccc(-c4ncc(Cl)cc4Cl)cc3Cl)[nH]c2c1] | 71 | (CDCl$_3$) δ: 8.66 (d, 1H), 8.61 (s, 1H), 8.32 (s, 1H), 7.98-7.86 (m, 4H) |
| 91 | 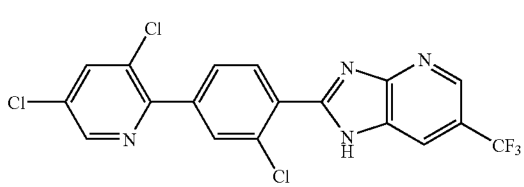 [SMILES: FC(F)(F)c1cnc2nc(-c3ccc(-c4ncc(Cl)cc4Cl)cc3Cl)[nH]c2c1] | 62 | (CDCl$_3$) δ: 8.78 (s, 1H), 8.63-8.55 (m, 2H), 8.50 (s, 1H), 7.97 (s, 1H), 7.93-7.83 (m, 2H) |

¹H NMR (CDCl₃) 8.85 (s, 1H), 8.37 (d, 1H), 8.08 (s, 1H), 8.01 (s, 1H), 7.94 (s, 1H), 7.88 (d, 1H), 7.78 (d, 1H), 7.56 (d, 1H)

Example 93

Preparation of 4-chloro-2-[2-chloro-4-(3-chloro-5-trifluoromethylpyridin-2-yl)phenyl]-6-trifluoromethyl-1H-benzoimidazole

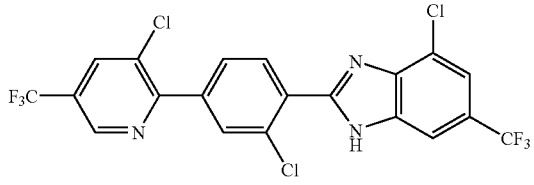 [SMILES: FC(F)(F)c1cnc(-c2ccc(-c3nc4c(Cl)cc(C(F)(F)F)cc4[nH]3)c(Cl)c2)c(Cl)c1]

The same procedure as in (2) of Example 92 was performed to produce 4-chloro-2-[2-chloro-4-(3-chloro-5-trifluoromethylpyridin-2-yl)phenyl]-6-trifluoromethyl-1H-benzoimidazole (yield 71%).

¹H NMR (CDCl₃) δ: 8.89 (s, 1H), 8.72 (d, 1H), 8.10 (s, 1H), 7.94-7.87 (m, 3H), 7.64 (s, 1H)

Example 94

Preparation of N-[4'-(6-tert-butyl-1H-benzoimidazole-2-yl)-3'-chloro-3-fluorobiphenyl-4-yl]methanesulfonamide

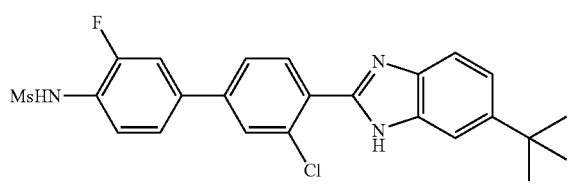

(1) Preparation of 4-(3-fluoro-4-methanesulfonylaminophenyl)-2-chlorobenzoic acid The same procedure as in (1) of Example 1 was performed to produce 4-(3-fluoro-4-methanesulfonylaminophenyl)-2-chlorobenzoic acid (yield 54%).

¹H NMR (CD₃OD) δ: 7.93 (d, 1H), 7.78 (d, 1H), 7.67-7.63 (m, 2H), 7.60-7.53 (m, 2H), 3.05 (s, 3H)

(2) Preparation of N-[4'-(6-tert-butyl-1H-benzoimidazole-2-yl)-3'-chloro-3-fluorobiphenyl-4-yl]methanesulfonamide The same procedure as in (3) of Example 1 was performed to produce N-[4'-(6-tert-butyl-1H-benzoimidazole-2-yl)-3'-chloro-3-fluorobiphenyl-4-yl]methanesulfonamide (yield 60%).

¹H NMR (CD₃OD) δ: 7.94 (d, 1H), 7.89 (s, 1H), 7.75 (d, 1H), 7.67-7.56 (m, 5H), 7.44 (d, 1H), 3.06 (s, 3H), 1.41 (s, 9H)

Examples 95 and 96

The same procedure as in (2) of Example 94 was performed to produce Compounds 95 and 96.

| Cpds. | Structures | Yields | Spectrum Data (¹H NMR) |
|---|---|---|---|
| 95 | ![structure] | 53 | (CDCl₃) δ: 7.75-7.64 (m, 3H), 7.47-7.43 (m, 2H), 7.34-7.27 (m, 2H), 6.63 (s, 1H), 3.10 (s, 3H) |
| 96 | ![structure] | 50 | (CDCl₃) δ: 7.98 (s, 1H), 7.74-7.68 (m, 2H), 7.48-7.43 (m, 2H), 7.32-7.27 (m, 2H), 6.65-6.63 (m, 1H), 3.11 (s, 3H) |

Example 97

Preparation of 2-[2-chloro-4-(3-trifluoromethylpyridin-2-yl)phenyl]-6-trifluoromethyl-1H-benzoimidazole

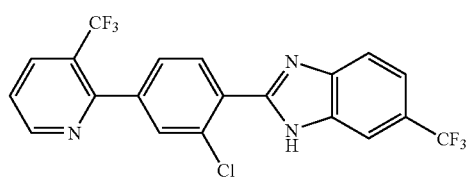 [SMILES: FC(F)(F)c1ccc2nc(-c3ccc(-c4ncccc4C(F)(F)F)cc3Cl)[nH]c2c1]

(1) Preparation of 2-chloro-4-(3-trifluoromethylpyridin-2-yl)benzoic acid

The same procedure as in (1) of Example 1 was performed to produce 2-chloro-4-(3-trifluoromethylpyridin-2-yl)benzoic acid (yield 73%).

$^1$H NMR (CD$_3$OD) δ: 8.78-8.76 (m, 1H), 8.20 (d, 1H), 7.91 (d, 1H), 7.80-7.76 (m, 2H), 7.41-7.39 (m, 1H)

(2) Preparation of 2-[2-chloro-4-(3-trifluoromethylpyridin-2-yl)phenyl]-6-trifluoromethyl-1H-benzoimidazole The same procedure as in (3) of Example 1 was performed to produce 2-[2-chloro-4-(3-trifluoromethylpyridin-2-yl)phenyl]-6-trifluoromethyl-1H-benzoimidazole (yield 92%).

$^1$H NMR (CDCl$_3$) δ: 8.89 (d, 1H), 8.59 (d, 1H), 8.15 (d, 1H), 8.10-7.75 (m, 1H), 7.73 (s, 1H), 7.65-7.50 (m, 4H)

Examples 98 and 99

The same procedure as in (2) of Example 97 was performed to produce Compounds 98 and 99.

ducted many times and the organic layer was dried over magnesium sulfate and vacuum concentrated. The concentrate was dissolved in 25 mL dimethylformamide and mixed with 0.5 g (3.0 mmol) 4-tert-butylbenzene-1,2-diamine, 1.2 mL (6.0 mmol) diisopropylethylamine and 1.3 g (7.2 mmol) O-(7-azabenzotriazol-1-yl)-N,N,N',N'-tetramethyleuronium hexafluorophosphate, followed by stirring at room temperature for 16 hours. The concentrate obtained by vacuum concentration was dissolved in ethyl acetate, washed with saturated NaHCO$_3$ and saturated NaCl, and dried over magnesium sulfate, followed by vacuum concentration. The residue thus obtained was dissolved in acetic acid/toluene (15 mL/1.5 mL), and the solution was stirred at 75° C. for 3 hours and vacuum concentrated. Again, this concentrate was dissolved in ethyl acetate, washed with saturated NaHCO$_3$ and saturated NaCl, and dried over magnesium sulfate, followed by vacuum concentration. The residue was separated using column chromatography (developing solvent: chloroform/methanol=30/1) to produce 0.77 g of 6-tert-butyl-2-[2-chloro-4-(3-methylpyridin-2-yl)phenyl]-1H-benzoimidazole (yield 68%).

| Cpds. | Structures | Yield | Spectrum Data ($^1$H NMR) |
|---|---|---|---|
| 98 | 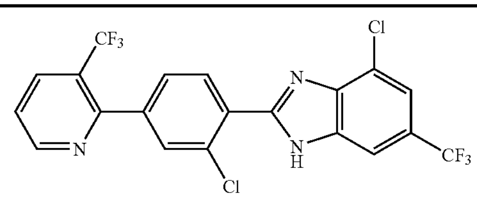 | 77 | (CDCl$_3$) δ: 8.92 (d, 1H), 8.69 (d, 1H), 8.17 (d, 1H), 8.08 (s, 1H), 7.76 (s, 1H), 7.66 (d, 2H), 7.60-7.56 (m, 1H) |
| 99 | 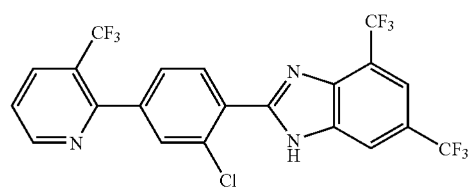 | 63 | (CDCl$_3$) δ: 8.89 (d, 1H), 8.64 (d, 1H), 8.32 (s, 1H), 8.17 (d, 1H), 7.86 (s, 1H), 7.77 (s, 1H), 7.68 (d, 1H), 7.60-7.55 (m, 1H) |

Example 100

Preparation of 6-tert-butyl-2-[2-chloro-4-(3-methylpyridin-2-yl)phenyl]-1H-benzoimidazole

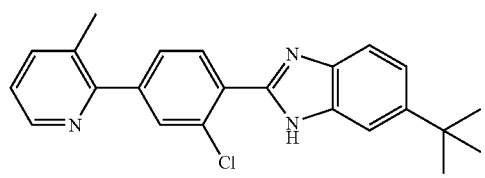 [SMILES: Cc1cccnc1-c1ccc(-c2nc3ccc(C(C)(C)C)cc3[nH]2)c(Cl)c1]

To a solution of 0.46 g (3.6 mmol) 2-chloro-3-methylpyridine in 20 mL 1,2-dimethoxyethane and 20 mL distilled water were added 2.2 g (21.1 mmol) Na$_2$CO$_3$, 0.6 g (3.0 mmol) 3-chloro-4-carboxylphenylboronic acid and 50 mg Pd(PPh$_3$)$_4$, followed by stirring the solution for 15 hours in a heat flux condition and concentrating in a vacuum. The aqueous layer was washed with ethyl acetate and adjusted to a pH of 1 with conc. HCl. Thereafter, extraction with ethyl acetate was con- $^1$H NMR (CDCl$_3$) δ: 8.69 (d, 1H), 8.56-8.52 (m, 1H) 8.06 (s, 1H), 7.73 (s, 1H), 7.53-7.48 (m, 1H), 7.42-7.39 (m, 1H), 7.31-7.27 (m, 1H), 7.18-7.14 (m, 1H), 6.89 (d, 1H), 2.67 (s, 3H), 1.38 (s, 9H)

Example 101

Preparation of 6-chloro-2-(2-chloro-4-pyridin-2-ylphenyl)-1H-benzoimidazole

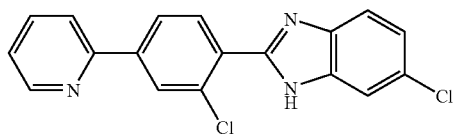

(1) Preparation of 2-chloro-4-pyridin-2-ylbenzoic acid

The same procedure as in (1) of Example 1 was performed to produce 2-chloro-4-pyridin-2-ylbenzoic acid (yield 65%).

¹H NMR (CD₃OD) δ: 8.63 (s, 1H), 8.05 (s, 1H), 7.99-7.89 (m, 2H), 7.41-7.39 (m, 2H), 6.65-6.63 (m, 1H)

(2) Preparation of 6-chloro-2-(2-chloro-4-pyridin-2-ylphenyl)-1H-benzoimidazole

The same procedure as in (3) of Example 1 was performed to produce 6-chloro-2-(2-chloro-4-pyridin-2-ylphenyl)-1H-benzoimidazole (yield 85%).

¹H NMR (CDCl₃) δ: 8.72 (d, 1H), 8.48 (d, 1H), 8.19 (s, 1H), 8.00 (d, 1H), 7.82-7.68 (m, 2H), 7.62 (s, 1H), 7.59 (d, 1H), 7.31-7.29 (m, 2H)

Examples 102 and 103

The same procedure as in (2) of Example 101 was performed to produce Compounds 102 and 103.

1 hour, followed by stirring for an additional 30 min. The solution was withdrawn from the ice bath and stirred at 40° C. for an additional 2 hours. The resulting reaction solution was filtered through celite to remove solid matters. To the filtrate was added 10 mL ethyl acetate 10 mL. After the pH of the aqueous layer was adjusted to 4.0 with a 5.0N HCl solution, the ethyl acetate layer was separated, dried over anhydrous magnesium sulfate and vacuum concentrated. The residue thus obtained was dissolved in a small amount of methanol and separated using column chromatography (chloroform/methanol=10:1) to produce 0.14 g of 4-carboxynaphthalene-1-bronic acid (yield 58%).

¹H NMR (CDCl₃) δ: 7.68-7.62 (m, 2H), 7.40-7.34 (m, 4H)

| Cpds. | Structures | Yield | Spectrum Data (¹H NMR) |
|---|---|---|---|
| 102 | 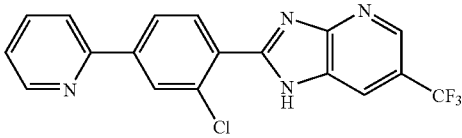 [SMILES: FC(F)(F)c1cnc2nc(-c3ccc(-c4ccccn4)cc3Cl)[nH]c2c1] | 52 | (CDCl₃) δ: 8.86 (d, 1H), 8.76 (s, 1H), 8.62 (d, 1H), 8.37 (d, 1H), 8.15-8.10 (m, 2H), 8.01 (d, 1H), 7.62-7.55 (m, 2H) |
| 103 | 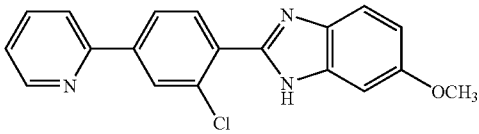 [SMILES: COc1ccc2nc(-c3ccc(-c4ccccn4)cc3Cl)[nH]c2c1] | 85 | (CDCl₃) δ: 8.32 (d, 1H), 7.67 (d, 2H), 7.61-7.25 (m, 1H), 7.49 (s, 1H), 7.42-7.34 (m, 4H), 7.02 (d, 1H), 3.87 (s, 3H) |

Example 104

Preparation of 2-[4-(3-chloropyridin-2-yl)naphthalen-1-yl]-6-trifluoromethyl-1H-benzoimidazole

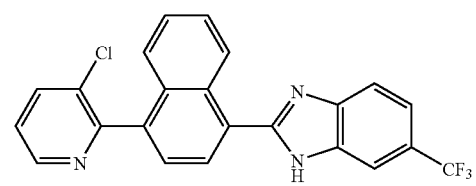

(1) Preparation of 4-carboxynaphthalene-1-bronic acid

To 5 mL of a 25% sodium hydroxide solution was slowly added 0.2 g (1.08 mmol) 4-methylnaphthalene-1-boronic acid. During this process, the container was kept in an ice bath. To this, a solution of 0.43 g (2.70 mmol) potassium permanganate in 5 mL distilled water was slowly added over (2) Preparation of 4-(3-chloropyridin-2-yl)naphthalen-1-carboxylic acid The same procedure as in (1) of Example 1 was performed to produce 4-(3-chloropyridin-2-yl)naphthalen-1-carboxylic acid (yield 60%).

¹H NMR (CD₃OD) δ: 8.97 (d, 1H), 8.63 (dd, 1H), 8.27 (d, 1H), 8.12 (d, 1H), 7.63-7.49 (m, 4H), 7.40 (d, 1H)

(3) Preparation of 2-[4-(3-chloropyridin-2-yl)naphthalen-1-yl]-6-trifluoromethyl-1H-benzoimidazole The same procedure as in (3) of Example 1 was performed to produce 2-[4-(3-chloropyridin-2-yl)naphthalen-1-yl]-6-trifluoromethyl-1H-benzoimidazole (yield 79%).

¹H NMR (CDCl₃) δ: 8.74 (d, 1H), 8.56 (d, 1H), 8.01-7.95 (m, 2H), 7.86 (d, 1H), 7.78 (d, 1H), 7.53 (d, 1H), 7.47 (d, 2H), 7.40-7.27 (m, 3H)

Examples 105 to 107

The same procedure as in (3) of Example 1 was performed to produce Compounds 105 to 107.

| Cpds. | Structures | Yield | Spectrum Data ($^1$H NMR) |
|---|---|---|---|
| 105 | 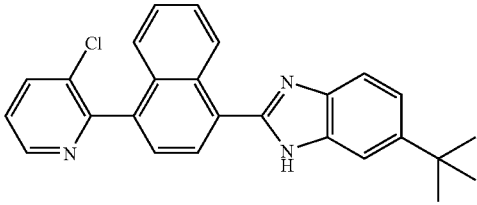 [SMILES: CC(C)(C)c1ccc2nc(-c3ccc(-c4ncccc4Cl)c4ccccc34)[nH]c2c1] | 96 | (CD$_3$OD) δ: 8.66 (d, 1H), 8.65 (d, 1H), 8.13 (d, 1H), 7.98 (d, 1H), 7.71 (s, 1H), 7.64-7.58 (m, 5H), 7.47-7.44 (m, 2H), 1.44 (s, 9H) |
| 106 | 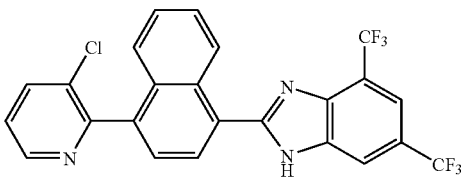 [SMILES: FC(F)(F)c1cc(C(F)(F)F)c2nc(-c3ccc(-c4ncccc4Cl)c4ccccc34)[nH]c2c1] | 75 | (CD$_3$OD) δ: 8.70 (d, 1H), 8.14-8.09 (m, 1H), 8.08 (d, 1H), 8.00 (s, 1H), 7.72-7.68 (m, 5H), 7.66-7.60 (m, 1H), 7.47-7.28 (m, 1H) |
| 107 | 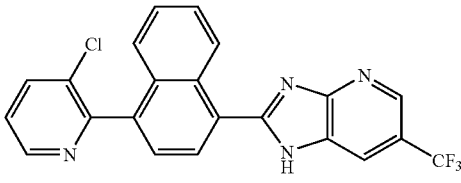 | 69 | (CDCl$_3$) δ: 8.65-8.55 (m, 4H), 8.13-8.15 (m, 1H), 7.74-7.68 (m, 3H), 7.35-7.30 (m, 2H), 7.19-7.15 (m, 1H) |

Example 108

Preparation of 6-tert-butyl-2-[4-(3,5-dichloropyridin-2-yl)naphthalen-1-yl]-1H-benzoimidazole

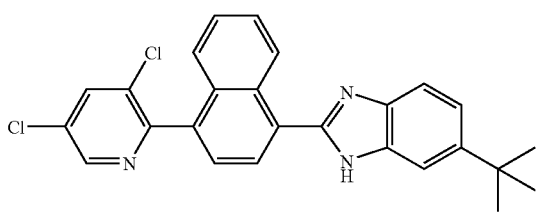 [SMILES: CC(C)(C)c1ccc2nc(-c3ccc(-c4ncc(Cl)cc4Cl)c4ccccc34)[nH]c2c1]

(1) Preparation of 4-(3,5-dichloropyridin-2-yl)naphthalen-1-carboxylic acid

The same procedure as in (1) of Example 1 was performed to produce 4-(3,5-dichloropyridin-2-yl)naphthalen-1-carboxylic acid (yield 56%).

$^1$H NMR (CD$_3$OD) δ: 8.92 (d, 1H), 8.63 (s, 1H), 8.19 (d, 2H), 7.60-7.55 (m, 1H), 7.49-7.42 (m, 2H), 7.36 (d, 1H)

(2) Preparation of 6-tert-butyl-2-[4-(3,5-dichloropyridin-2-yl)naphthalen-1-yl]-1H-benzoimidazole The same procedure as in (3) of Example 1 was performed to produce 6-tert-butyl-2-[4-(3,5-dichloropyridin-2-yl)naphthalen-1-yl]-1H-benzoimidazole (yield 79%).

$^1$H NMR (DMSO-d$_6$) δ: 7.99-7.95 (m, 1H), 7.70-7.64 (m, 1H), 7.45-7.41 (m, 1H), 7.18-7.15 (m, 1H), 6.87-6.46 (m, 7H), 0.57 (s, 9H)

Example 109

Preparation of 2-[4-(3,5-dichloropyridin-2-yl)naphthalen-1-yl]-4,6-bistrifluoromethyl-1H-benzoimidazole

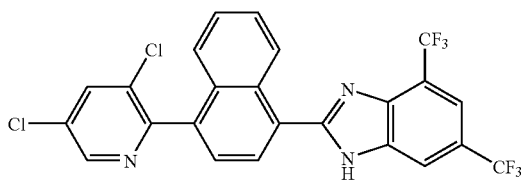 [SMILES: FC(F)(F)c1cc(C(F)(F)F)c2nc(-c3ccc(-c4ncc(Cl)cc4Cl)c4ccccc34)[nH]c2c1]

The same procedure as in (2) of Example 108 was performed to produce 2-[4-(3,5-dichloropyridin-2-yl)naphthalen-1-yl]-4,6-bistrifluoromethyl-1H-benzoimidazole (yield 60%).

¹H NMR (DMSO-d₆) δ: 8.00 (d, 1H), 7.68 (s, 1H), 7.50 (d, 1H), 7.44-7.40 (m, 1H), 7.29-7.25 (m, 1H), 6.85-6.63 (m, 5H)

Example 110

Preparation of 6-tert-butyl-2-[4-(3-chloro-5-trifluoromethylpyridin-2-yl)naphthalen-1-yl]-1H-benzoimidazole

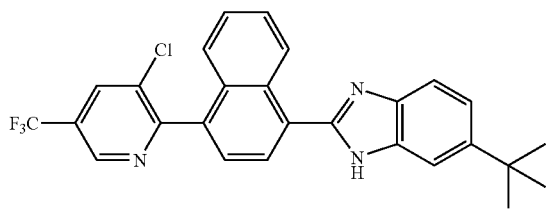 [SMILES: CC(C)(C)c1ccc2nc(-c3ccc(-c4ncc(C(F)(F)F)cc4Cl)c4ccccc34)[nH]c2c1]

The same procedure as in Example 100 was performed to produce 6-tert-butyl-2-[4-(3-chloro-5-trifluoromethylpyridin-2-yl)naphthalen-1-yl]-1H-benzoimidazole (yield 56%).

¹H NMR (DMSO-d₆) δ: 8.36-8.30 (m, 1H), 7.93-7.89 (m, 1H), 7.48-7.44 (m, 1H), 7.28-7.25 (m, 1H), 6.91-6.59 (m, 7H), 0.59 (s, 9H)

Example 111

Preparation of 2-[4-(3-chloro-5-trifluoromethylpyridin-2-yl)naphthalen-1-yl]-4,6-bistrifluoromethyl-1H-benzoimidazole

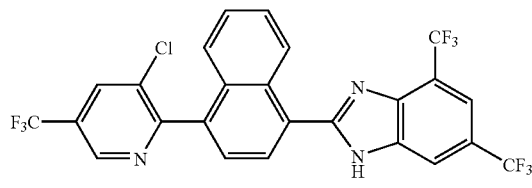 [SMILES: FC(F)(F)c1cnc(-c2ccc(-c3nc4c(C(F)(F)F)cc(C(F)(F)F)cc4[nH]3)c3ccccc23)c(Cl)c1]

The same procedure as in Example 110 was performed to produce 2-[4-(3-chloro-5-trifluoromethylpyridin-2-yl)naphthalen-1-yl]-4,6-bistrifluoromethyl-1H-benzoimidazole (yield 55%).

¹H NMR (DMSO-d₆) δ: 8.34 (d, 1H), 7.91 (s, 1H), 7.55 (d, 1H), 7.43-7.37 (m, 1H), 7.27 (d, 1H), 6.84-6.64 (m, 5H)

Example 112

Preparation of N-{4-[4-(4,6-bistrifluoromethyl-1H-benzoimidazole-2-yl)naphthalen-1-yl]-2-fluorophenyl}methanesulfonamide

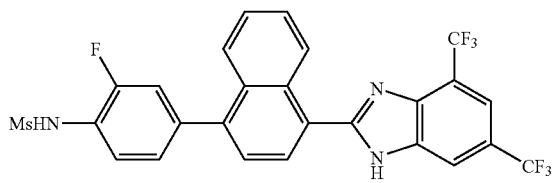

(1) Preparation of 4-(3-fluoro-4-methanesulfonylaminophenyl)naphthalen-1-carboxylic acid The same procedure as in (1) of Example 1 was performed to produce 4-(3-fluoro-4-methanesulfonylaminophenyl)naphthalen-1-carboxylic acid (yield 43%).

¹H NMR (CD₃OD) δ: 8.92 (d, 1H), 8.14 (d, 1H), 7.82 (s, 1H), 7.64-7.58 (m, 2H), 7.48-7.41 (m, 2H), 7.29-7.25 (m, 2H), 3.06 (s, 3H)

(2) Preparation of N-{4-[4-(4,6-bistrifluoromethyl-1H-benzoimidazole-2-yl)naphthalen-1-yl]-2-fluorophenyl}methanesulfonamide The same procedure as in (3) of Example 1 was performed to produce N-{4-[4-(4,6-bistrifluoromethyl-1H-benzoimidazole-2-yl)naphthalen-1-yl]-2-fluorophenyl}methanesulfonamide (yield 55%).

¹H NMR (CD₃OD) δ: 8.43 (d, 1H), 8.00-7.89 (m, 3H), 7.70-7.60 (m, 3H), 7.61-7.52 (m, 2H), 7.37-7.30 (m, 2H), 3.11 (s, 3H)

Example 113

Preparation of 6-trifluoromethyl-2-[4-(3-trifluoromethylpyridin-2-yl)naphthalen-1-yl]-1H-benzoimidazole

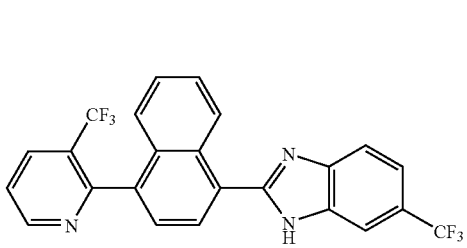

(1) Preparation of 4-(3-trifluoromethylpyridin-2-yl)naphthalen-1-carboxylic acid The same procedure as in (1) of Example 1 was performed to produce 4-(3-trifluoromethylpyridin-2-yl)naphthalen-1-carboxylic acid (yield 60%).

¹H NMR (CD₃OD) δ: 8.75 (d, 1H), 8.35 (d, 1H), 8.26 (d, 2H), 7.74-7.70 (m, 2H), 7.59-7.54 (m, 2H), 7.25 (d, 1H)

(2) Preparation of 6-trifluoromethyl-2-[4-(3-trifluoromethylpyridin-2-yl)naphthalen-1-yl]-1H-benzoimidazole The same procedure as in (3) of Example 1 was performed to produce 6-trifluoromethyl-2-[4-(3-trifluoromethylpyridin-2-yl)naphthalen-1-yl]-1H-benzoimidazole (yield 64%).

$^1$H NMR (CDCl$_3$) δ: 8.60-8.50 (m, 3H), 8.13-8.11 (m, 1H), 7.91-7.85 (m, 1H), 7.65-7.62 (m, 1H), 7.47-7.42 (m, 2H), 7.34-7.30 (m, 2H), 7.49-7.46 (m, 1H), 7.02-6.98 (m, 1H)

Example 114

Preparation of 6-tert-butyl-2-(4-pyridin-2-ylnaphthalen-1-yl)-1H-benzoimidazole

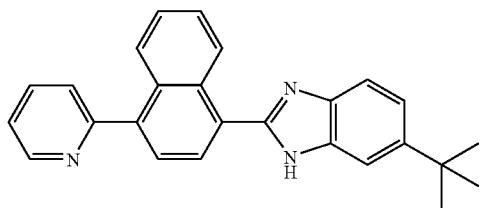

The same procedure as in Example 100 was performed to produce 6-tert-butyl-2-(4-pyridin-2-ylnaphthalen-1-yl)-1H-benzoimidazole (yield 57%).
$^1$H NMR (CDCl$_3$) δ: 8.74 (d, 1H), 7.98 (d, 1H), 7.88 (d, 1H), 7.78 (d, 2H), 7.60 (d, 2H), 7.52-7.40 (m, 6H), 1.48 (s, 9H)

Example 115

Preparation of 2-(4-pyridin-2-ylnaphthalen-1-yl)-4,6-bistrifluoromethyl-1H-benzoimidazole

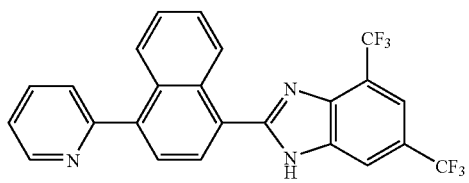 [SMILES: FC(F)(F)c1cc(C(F)(F)F)c2nc(-c3ccc(-c4ccccn4)c4ccccc34)[nH]c2c1]

The same procedure as in Example 114 was performed to produce 2-(4-pyridin-2-ylnaphthalen-1-yl)-4,6-bistrifluoromethyl-1H-benzoimidazole (yield 47%).
$^1$H NMR (CD$_3$OD) δ: 8.74 (d, 1H), 8.44 (d, 1H), 8.03 (d, 2H), 7.94 (d, 2H), 7.72-7.66 (m, 3H), 7.64-7.58 (m, 2H), 7.05 (d, 1H)

Example 116

Preparation of 6-tert-butyl-2-[3-chloro-4-(3-chloropyridin-2-yl)phenyl]-1H-benzoimidazole

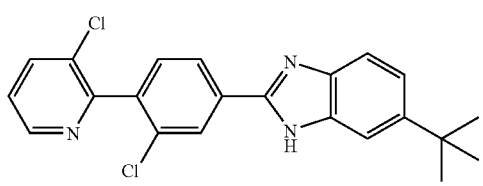

(1) Preparation of 3-chloro-4-(4,4,5,5-tetramethyl-[1,3,2]dioxabororan-2-yl)benzoic acid The same procedure as in (1) of Example 104 was performed to produce 3-chloro-4-(4,4,5,5-tetramethyl-[1,3,2]dioxabororan-2-yl)benzoic acid (yield 50%).
$^1$H NMR (CD$_3$OD) δ: 7.89 (s, 1H), 7.80 (d, 1H), 7.65 (d, 1H), 1.37 (s, 12H)

(2) Preparation of 3-chloro-4-(3-chloropyridin-2-yl)benzoic acid

The same procedure as in (1) of Example 1 was performed to produce 3-chloro-4-(3-chloropyridin-2-yl)benzoic acid (yield 69%).
$^1$H NMR (CD$_3$OD) δ: 8.51 (dd, 1H), 8.04 (d, 1H), 7.97 (dd, 1H), 7.95 (dd, 1H), 7.45 (dd, 1H), 7.32 (d, 1H)

(3) Preparation of 6-tert-butyl-2-[3-chloro-4-(3-chloropyridin-2-yl)phenyl]-1H-benzoimidazole The same procedure as in (3) of Example 1 was performed to produce 6-tert-butyl-2-[3-chloro-4-(3-chloropyridin-2-yl)phenyl]-1H-benzoimidazole (yield 86%).
$^1$H NMR (CDCl$_3$) δ: 8.72 (d, 1H), 8.48 (d, 1H), 8.19 (s, 1H), 8.00 (d, 1H), 7.82-7.68 (m, 1H), 7.62 (s, 1H), 7.59 (d, 1H), 7.31-7.29 (m, 2H), 1.42 (s, 9H)

Example 117

Preparation of 2-[3-chloro-4-(3,5-dichloropyridin-2-yl)phenyl]-6-trifluoromethyl-1H-benzoimidazole

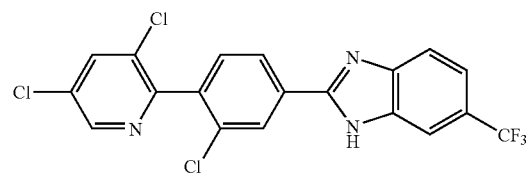 [SMILES: FC(F)(F)c1ccc2nc(-c3ccc(-c4ncc(Cl)cc4Cl)c(Cl)c3)[nH]c2c1]

(1) Preparation of 3-chloro-4-(3,5-dichloropyridin-2-yl)benzoic acid

The same procedure as in (1) of Example 1 was performed to produce 3-chloro-4-(3,5-dichloropyridin-2-yl)benzoic acid (yield 64%).
$^1$H NMR (CD$_3$OD) δ: 8.58 (s, 1H), 8.13 (s, 1H), 8.10 (d, 1H), 8.00 (d, 1H), 7.36 (d, 1H)

(2) Preparation of 2-[3-chloro-4-(3,5-dichloropyridin-2-yl)phenyl]-6-trifluoromethyl-1H-benzoimidazole The same procedure as in (3) of Example 1 was performed to produce 2-[3-chloro-4-(3,5-dichloropyridin-2-yl)phenyl]-6-trifluoromethyl-1H-benzoimidazole (yield 70%).
$^1$H NMR (CD$_3$OD) δ: 8.56 (s, 1H), 8.26 (s, 1H), 8.12 (dd, 2H), 7.88 (s, 1H), 7.72 (d, 1H), 7.54 (d, 1H), 7.49 (d, 1H)

Examples 118 and 119

The same procedure as in (2) of Example 117 was performed to produce Compounds 118 and 119.

| Cpds. | Structures | Yield | Spectrum Data (¹H NMR) |
|---|---|---|---|
| 118 | 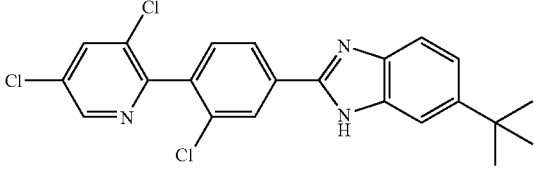 [SMILES: CC(C)(C)c1ccc2nc(-c3ccc(-c4ncc(Cl)cc4Cl)c(Cl)c3)[nH]c2c1] | 78 | (CD₃OD) δ: 8.64 (s, 1H), 8.28 (s, 1H), 8.20 (s, 1H), 8.13 (d, 1H), 7.65-7.56 (m, 3H), 7.44 (d, 1H), 1.41 (s, 9H) |
| 119 | 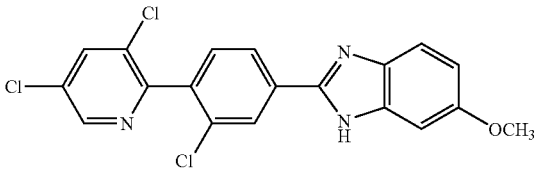 [SMILES: COc1ccc2nc(-c3ccc(-c4ncc(Cl)cc4Cl)c(Cl)c3)[nH]c2c1] | 85 | (CD₃OD) δ: 8.64 (d, 0.6H), 8.61 (d, 0.4H), 8.25 (s, 0.6H), 8.20-8.15 (m, 1.0H), 8.12-8.07 (m, 1.0H), 7.58-7.50 (m, 2.4H), 7.12 (s, 0.6H), 7.10 (s, 0.4H), 6.97-6.92 (m, 1.0H), 3.87 (s, 1.8H), 3.85 (s, 1.2H) |

Example 120

Preparation of 2-[3-chloro-4-(3-chloro-5-trifluoromethylpyridin-2-yl)phenyl]-6-trifluoromethyl-1H-benzoimidazole (1) Preparation of 3-chloro-4-(3-chloro-5-trifluoromethylpyridin-2-yl)benzoic acid The same procedure as in (1) of Example 1 was performed to produce 3-chloro-4-(3-chloro-5-trifluoromethylpyridin-2-yl)benzoic acid (yield 69%).

¹H NMR (CD₃OD) δ: 8.90 (s, 1H), 8.39 (s, 1H), 8.11 (s, 1H), 8.00 (d, 1H), 7.33 (d, 1H)

(2) Preparation of 2-[3-chloro-4-(3-chloro-5-trifluoromethylpyridin-2-yl)phenyl]-6-trifluoromethyl-1H-benzoimidazole The same procedure as in (3) of Example 1 was performed to produce 2-[3-chloro-4-(3-chloro-5-trifluoromethylpyridin-2-yl)phenyl]-6-trifluoromethyl-1H-benzoimidazole (yield 80%).

¹H NMR (CD₃OD) δ: 8.60 (s, 1H), 8.09 (s, 1H), 7.99-7.96 (m, 1H), 7.85 (s, 1H), 7.69 (d, 1H), 7.53-7.48 (m, 3H)

Examples 121 and 122

The same procedure as in (2) of Example 120 was performed to produce Compounds 121 and 122.

| Cpds. | Structures | Yield | Spectrum Data (¹H NMR) |
|---|---|---|---|
| 121 | 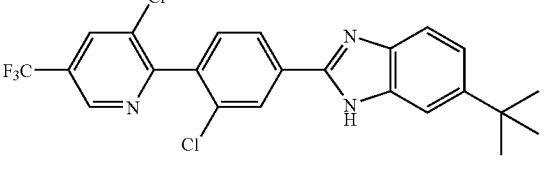 | 82 | (CDCl₃) δ: 8.62 (s, 1H), 8.02-7.96 (m, 1H), 7.79-7.73 (m, 2H), 7.60-7.56 (m, 1H), 7.47-7.43 (m, 1H), 7.31-7.28 (m, 1H), 7.18-7.14 (m, 1H), 1.42 (s, 9H) |

| Cpds. | Structures | Yield | Spectrum Data ($^1$H NMR) |
|---|---|---|---|
| 122 | 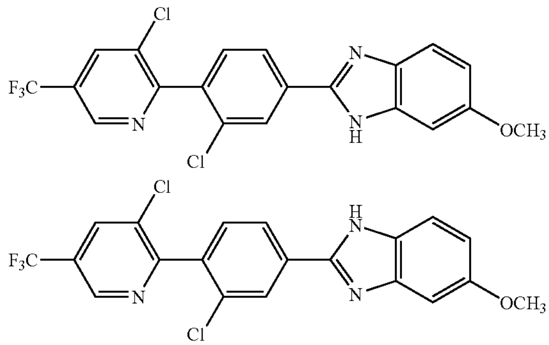 | 79 | (CD$_3$OD) δ: 8.96 (s, 0.6H), 8.94 (s, 0.4H), 8.45 (s, 0.6H), 8.43 (s, 0.4H), 8.28 (s, 0.6H), 0.4H), 8.15-8.10 (m, 1.4H), 7.98-7.92 (m, 1.0H), 7.63-7.58 (m, 1.0H), 7.56-7.51 (m, 1.0H), 7.13 (d, 0.6H), 7.10 (d, 0.4H), 3.88 (s, 1.8H), 3.85 (s, 1.2H) |

Example 123

Preparation of N-[2'-chloro-4'-(4-chloro-6-trifluoromethyl-1H-benzoimidazole-2-yl)-3-fluorobiphenyl-4-yl]methanesulfonamide

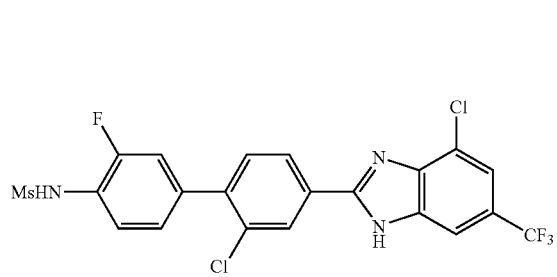

(1) Preparation of 3-chloro-4-(3-fluoro-4-methanesulfonylaminophenyl)benzoic acid The same procedure as in (1) of Example 1 was performed to produce 3-chloro-4-(3-fluoro-4-methanesulfonylaminophenyl)benzoic acid (yield 54%).

$^1$H NMR (CD$_3$OD) δ: 8.06 (s, 1H), 7.92 (d, 1H), 7.58 (dd, 1H), 7.40 (d, 1H), 7.34 (s, 1H), 7.28-7.25 (m, 1H), 3.06 (s, 3H)

(2) Preparation of N-[2'-chloro-4'-(4-chloro-6-trifluoromethyl-1H-benzoimidazole-2-yl)-3-fluorobiphenyl-4-yl]methanesulfonamide The same procedure as in (3) of Example 1 was performed to produce N-[2'-chloro-4'-(4-chloro-6-trifluoromethyl-1H-benzoimidazole-2-yl)-3-fluorobiphenyl-4-yl]methanesulfonamide (yield 60%).

$^1$H NMR (CD$_3$OD) δ: 8.40 (s, 1H), 8.21 (d, 1H), 7.88 (s, 1H), 7.42-7.34 (m, 3H), 7.42-7.34 (m, 2H), 3.08 (s, 3H)

Example 124

Preparation of N-[4'-(4,6-bistrifluoromethyl-1H-benzoimidazole-2-yl)-2'-chloro-3-fluorobiphenyl-4-yl]methanesulfonamide The same procedure as in (2) of Example 123 was performed to produce N-[4'-(4,6-bistrifluoromethyl-1H-benzoimidazole-2-yl)-2'-chloro-3-fluorobiphenyl-4-yl]methanesulfonamide (yield 56%).

$^1$H NMR (CD$_3$OD) δ: 8.43 (s, 1H), 8.25 (d, 1H), 8.18 (s, 1H), 7.83 (s, 1H), 7.67-7.61 (m, 2H), 7.43-7.34 (m, 2H), 3.10 (s, 3H)

Example 125

Preparation of 2-(3-chloro-4-pyridin-2-ylphenyl)-6-trifluoromethyl-1H-benzoimidazole

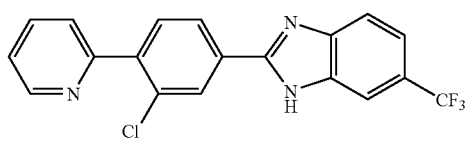 [SMILES: FC(F)(F)c1ccc2nc(-c3ccc(-c4ccccn4)c(Cl)c3)[nH]c2c1]

(1) Preparation of 3-chloro-4-pyridin-2-ylbenzoic acid

The same procedure as in (1) of Example 1 was performed to produce 3-chloro-4-pyridin-2-ylbenzoic acid (yield 68%).

$^1$H NMR (CD$_3$OD) δ: 8.66 (d, 1H), 8.14 (s, 1H), 8.05 (d, 1H), 7.99 (dd, 1H), 7.71 (d, 1H), 7.64 (d, 1H), 7.48 (dd, 1H)

(2) Preparation of 2-(3-chloro-4-pyridin-2-ylphenyl)-6-trifluoromethyl-1H-benzoimidazole The same procedure as in (3) of Example 1 was performed to produce 2-(3-chloro-4-pyridin-2-ylphenyl)-6-trifluoromethyl-1H-benzoimidazole (yield 88%).
$^1$H NMR (DMSO-d$_6$) δ: 7.93-7.89 (m, 1H), 7.63-7.56 (m, 1H), 7.50-7.44 (m, 1H), 7.19-7.11 (m, 2H), 7.02-6.95 (m, 3H), 6.76 (s, 1H), 6.67-6.62 (m, 1H)

Examples 126 to 130

The same procedure as in (2) of Example 125 was performed to produce Compounds 126 to 130.

Example 131

Preparation of 2-[3-chloro-4-(3-trifluoromethylpyridin-2-yl)phenyl]-6-trifluoromethyl-1H-benzoimidazole

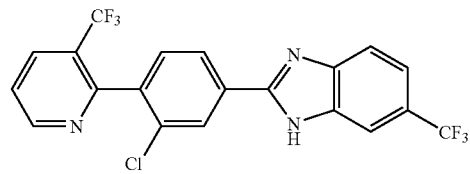 [SMILES: FC(F)(F)c1ccc2nc(-c3ccc(-c4ncccc4C(F)(F)F)c(Cl)c3)[nH]c2c1]

| Cpds. | Structures | Yield | Spectrum Data ($^1$H NMR) |
|---|---|---|---|
| 126 | 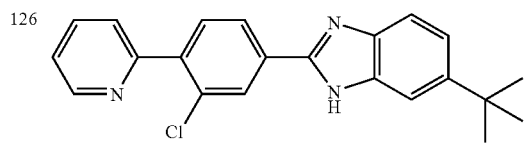 | 61 | (DMSO-d$_6$) δ: 7.92 (d, 1H), 7.52 (d, 1H), 7.42-7.38 (m, 1H), 7.15-7.11 (m, 1H), 6.97-6.92 (m, 2H), 6.87-6.83 (m, 1H), 6.79-6.73 (m, 2H), 6.67-6.63 (m, 1H), 0.57 (s, 9H) |
| 127 | 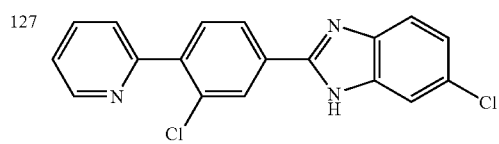 | 93 | (CD$_3$OD) δ: 8.69 (s, 1H), 8.30 (d, 1H), 8.15-8.13 (m, 1H), 7.99-7.98 (m, 1H), 7.76-7.72 (m, 2H), 7.66-7.62 (m, 2H), 7.52-7.50 (m, 1H), 7.32-7.31 (m, 1H) |
| 128 | 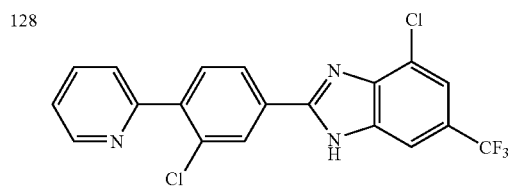 | 94 | (CD$_3$OD) δ: 8.69 (d, 1H), 8.44 (s, 1H), 8.26 (d, 1H), 8.00 (d, 1H), 7.95-7.90 (m, 1H), 7.75 (d, 2H), 7.62 (s, 1H), 7.55-7.50 (m, 1H) |
| 129 | 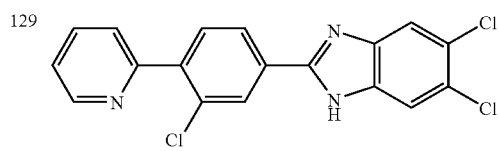 | 88 | (CD$_3$OD) δ: 8.67 (dd, 1H), 8.29 (d, 1H), 8.13 (dd, 1H), 7.97 (dd, 1H), 7.80-7.72 (m, 4H), 7.50 (dd, 1H) |
| 130 | 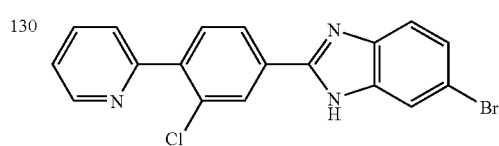 | 74 | (CD$_3$OD) δ: 8.68 (d, 1H), 8.29 (d, 1H), 8.12 (dd, 1H), 7.97 (dd, 1H), 7.80-7.70 (m, 3H), 7.55-7.48 (m, 2H), 7.43 (d, 1H) |

(1) Preparation of 3-chloro-4-(3-trifluoromethylpyridin-2-yl)benzoic acid

The same procedure as in (1) of Example 1 was performed to produce 3-chloro-4-(3-trifluoromethylpyridin-2-yl)benzoic acid (yield 76%).

$^1$H NMR (CD$_3$OD) δ: 7.98-7.91 (m, 3H), 7.60-7.57 (m, 2H), 7.46 (d, 1H)

(2) Preparation of 2-[3-chloro-4-(3-trifluoromethylpyridin-2-yl)phenyl]-6-trifluoromethyl-1H-benzoimidazole The same procedure as in (3) of Example 1 was performed to produce 2-[3-chloro-4-(3-trifluoromethylpyridin-2-yl)phenyl]-6-trifluoromethyl-1H-benzoimidazole (yield 89%).

$^1$H NMR (CDCl$_3$) δ: 8.02 (s, 1H), 7.97-7.93 (m, 1H), 7.85 (s, 1H), 7.64 (d, 1H), 7.44 (d, 2H), 7.42-7.37 (m, 3H)

Examples 132 to 134

The same procedure as in (2) of Example 131 was performed to produce Compounds 132 to 134.

The same procedure as in Example 100 was performed to produce 2-[3-chloro-4-(3-methylpyridin-2-yl)phenyl]-6-trifluoromethyl-1H-benzoimidazole (yield 48%).

$^1$H NMR (CDCl$_3$) δ: 8.01 (s, 1H), 7.96-7.91 (m, 1H), 7.84 (s, 1H), 7.62 (d, 1H), 7.44 (d, 1H), 7.37-7.34 (m, 4H), 2.70 (s, 3H)

Example 136

Preparation of 3-chloro-6'-(6-trifluoromethyl-1H-benzoimidazole-2-yl)-[2,3']bipyridine

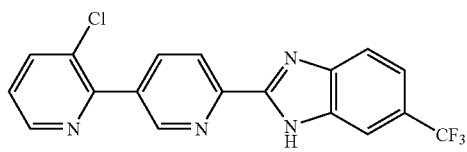

| Cpds. | Structures | Yield | Spectrum Data ($^1$H NMR) |
|---|---|---|---|
| 132 | ![structure] | 87 | (CDCl$_3$) δ: 8.04 (s, 1H), 8.02 (d, 1H), 7.92 (d, 1H), 7.78-7.82 (m, 1H), 7.61 (s, 1H), 7.55 (d, 1H), 7.47 (d, 1H), 7.38-7.31 (m, 2H), 1.42 (s, 9H) |
| 133 | ![structure] | 79 | (CDCl$_3$) δ: 7.97-7.91 (m, 3H), 7.53-7.43 (m, 3H), 7.36 (s, 2H), 7.18-7.15 (m, 1H) |
| 134 | ![structure] | 86 | (CDCl$_3$) δ: 7.96 (s, 1H), 7.95-7.89 (d, 1H), 7.46-7.43 (m, 2H), 7.38-7.34 (m, 3H), 7.02 (s, 1H), 6.85 (d, 1H), 3.80 (s, 3H) |

Example 135

Preparation of 2-[3-chloro-4-(3-methylpyridin-2-yl)phenyl]-6-trifluoromethyl-1H-benzoimidazole

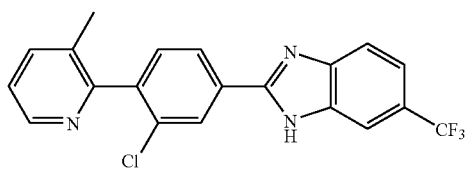 [SMILES: Cc1cccnc1-c1ccc(-c2nc3ccc(C(F)(F)F)cc3[nH]2)cc1Cl]

(1) Preparation of 3-chloro-2-(6-methylpyridin-3-yl)pyridine

To a solution of 0.5 g (3.6 mmol) 2,3-dichloropyridine in 20 mL 1,2-dimethoxyethane and 20 mL distilled water were added 2.2 g (21.1 mmol) Na$_2$CO$_3$, 0.41 g (3.0 mmol) 2-methylpyridine-5-boronic acid and 50 mg Pd(PPh$_3$)$_4$, followed by stirring for 18 hours in a heat flux condition. After being cooled to room temperature, the solution was 50% concentrated in a vacuum condition. The aqueous layer was washed with ethyl acetate. Thereafter, the organic layer was dried over magnesium sulfate and vacuum concentrated. The concentrate was separated using column chromatography (developing solvent: ethyl acetate/hexane=1/10) to produce 0.56 g of 3-chloro-2-(6-methylpyridin-3-yl)pyridine (yield 80%).

¹H NMR (CDCl₃) δ: 8.91 (d, 1H), 8.63 (dd, 1H), 7.99 (dd, 1H), 7.83 (dd, 1H), 7.49-7.47 (m, 1H), 7.30-7.27 (m, 1H), 2.65 (s, 3H)

(2) Preparation of 5-(3-chloropyridin-2-yl)pyridin-2-carboxylic acid

The same procedure as in (1) of Example 104 was performed to produce 5-(3-chloropyridin-2-yl)pyridin-2-carboxylic acid (yield 69%).

¹H NMR (CDCl₃) δ: 9.03 (d, 1H), 8.67 (dd, 1H), 8.36-8.32 (m, 2H), 7.88 (dd, 1H), 7.39-7.34 (m, 1H)

(3) Preparation of 3-chloro-6'-(6-trifluoromethyl-1H-benzoimidazole-2-yl)-[2,3']bipyridine The same procedure as in (3) of Example 1 was performed to produce 3-chloro-6'-(6-trifluoromethyl-1H-benzoimidazole-2-yl)-[2,3']bipyridine (yield 92%).

¹H NMR (CDCl₃) δ: 9.04 (d, 1H), 8.65 (dd, 1H), 8.58 (d, 1H), 8.35 (dd, 1H), 8.00 (s, 1H), 7.88 (dd, 1H), 7.78 (s, 1H), 7.56 (dd, 1H), 7.32 (dd, 1H)

Examples 137 to 145

The same procedure as in (3) of Example 136 was performed to produce Compounds 137 to 145.

| Cpds. | Structures | Yield | Spectrum Data (¹H NMR) |
|---|---|---|---|
| 137 | 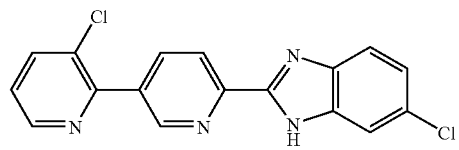 [SMILES: Clc1ccc2nc(-c3ccc(-c4ncccc4Cl)cn3)[nH]c2c1] | 89 | (CDCl₃) δ: 9.03 (d, 1H), 8.65 (dd, 1H), 8.56 (d, 1H), 8.33 (dd, 1H), 7.86 (dd, 1H), 7.72 (d, 1H), 7.60 (d, 1H), 7.32 (dd, 1H), 7.28 (dd, 1H) |
| 138 | 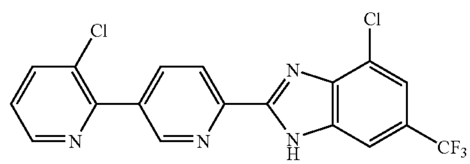 | 77 | (CDCl₃) δ: 9.10 (d, 1H), 8.68 (d, 1H), 8.52 (d, 1H), 8.38-8.31 (m, 1H), 8.05 (s, 1H), 7.88 (d, 1H), 7.59 (s, 1H), 7.36-7.29 (m, 1H) |
| 139 | 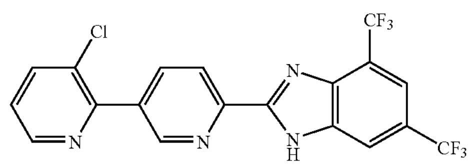 | 69 | (CDCl₃) δ: 9.08 (s, 1H), 8.65 (d, 1H), 8.51 (d, 1H), 8.33-8.28 (m, 2H), 7.85 (d, 1H), 7.80 (s, 1H), 7.34-7.31 (m, 1H) |
| 140 | 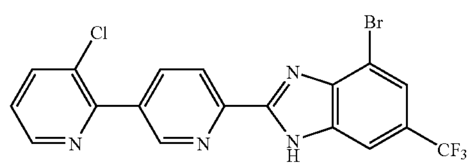 [SMILES: FC(F)(F)c1cc(Br)c2nc(-c3ccc(-c4ncccc4Cl)cn3)[nH]c2c1] | | (CDCl₃) δ: 9.06 (s, 1H), 8.65-8.57 (m, 2H), 8.35 (d, 1H), 8.04 (d, 1H), 7.91 (s, 1H), 7.73 (s, 1H), 7.47 (dd, 1H) |
| 141 | 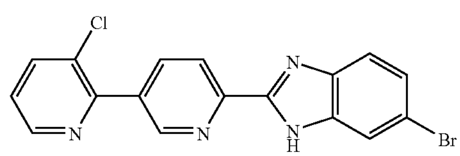 | | (CDCl₃) δ: 9.02 (d, 1H), 8.64 (dd, 1H), 8.52 (d, 1H), 8.30 (d, 1H), 7.83 (dd, 1H), 7.78 (s, 1H), 7.50 (d, 1H), 7.38 (d, 1H), 7.28 (dd, 1H) |
| 142 | 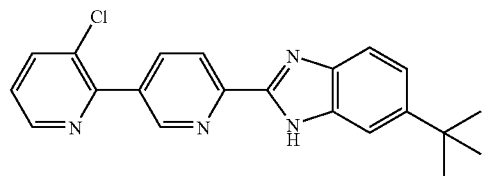 | | (CDCl₃) δ: 9.04 (d, 1H), 8.65 (dd, 2H), 8.30 (dd, 1H), 7.86 (dd, 1H), 7.70 (s, 1H), 7.60 (s, 1H), 7.44 (dd, 1H), 7.31 (dd, 1H), 1.41 (s, 9H) |
| 143 | 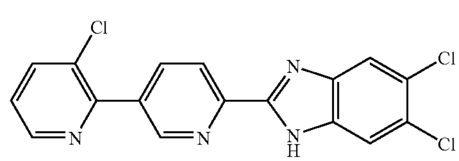 [SMILES: Clc1cc2nc(-c3ccc(-c4ncccc4Cl)cn3)[nH]c2cc1Cl] | | (CDCl₃) δ: 9.05 (d, 1H), 8.67 (dd, 1H), 8.57 (d, 1H), 8.34 (dd, 1H), 7.90-7.82 (m, 3H), 7.33 (dd, 1H) |

| Cpds. | Structures | Yield | Spectrum Data ($^1$H NMR) |
|---|---|---|---|
| 144 | 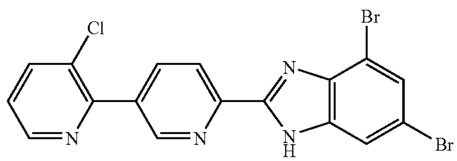 | | (CDCl$_3$) δ: 9.08 (d, 1H), 8.67 (dd, 1H), 8.52 (dd, 1H), 8.34 (dd, 1H), 7.88 (dd, 1H), 7.80 (s, 1H), 7.63 (dd, 1H), 7.34 (dd, 1H) |
| 145 | 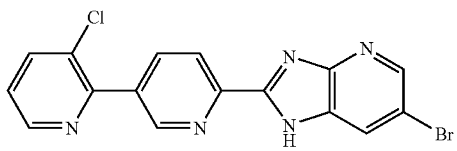 | | (CDCl$_3$) δ: 9.02 (d, 1H), 8.67 (dd, 1H), 8.37 (s, 2H), 8.23 (d, 1H), 7.97 (d, 1H), 7.89 (dd, 1H), 7.36 (dd, 1H) |

Example 146

Preparation of 3-chloro-6'-(6-morpholin-4-yl-1H-benzoimidazole-2-yl)-[2,3']bipyridine

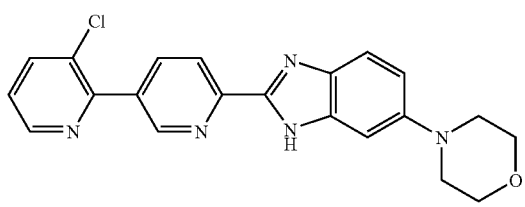 [SMILES: Clc1cccnc1-c1ccc(-c2nc3ccc(N4CCOCC4)cc3[nH]2)nc1]

The same procedure as in Example 17 was performed to produce 3-chloro-6'-(6-morpholin-4-yl-1H-benzoimidazole-2-yl)-[2,3']bipyridine (yield 72%).

$^1$H NMR (CD$_3$OD) δ: 9.21 (dd, 1H), 8.69 (d, 1H), 8.48 (dd, 1H), 8.35 (d, 1H), 8.09 (d, 1H), 7.73 (d, 1H), 7.55-7.50 (m, 1H), 7.45 (dd, 1H), 7.23 (d, 1H), 3.92-3.88 (m, 4H), 3.32-3.29 (m, 4H)

Examples 147 to 150

The same procedure as in Example 146 was performed to produce Compounds 147 to 150.

| Cpds. | Structures | Yield | Spectrum Data ($^1$H NMR) |
|---|---|---|---|
| 147 | 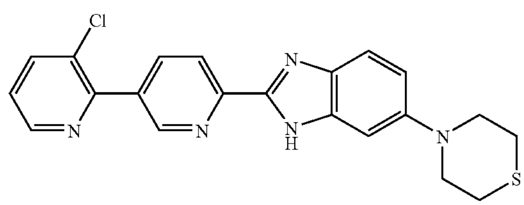 | 65 | (CD$_3$OD) δ: 9.19 (dd, 1H), 8.68 (d, 1H), 8.47 (dd, 1H), 8.36 (d, 1H), 8.08 (dd, 1H), 7.72 (d, 1H), 7.54-7.50 (m, 1H), 7.40 (dd, 1H), 7.24 (d, 1H), 3.74-3.70 (m, 4H), 2.84-2.80 (m, 4H) |
| 148 | 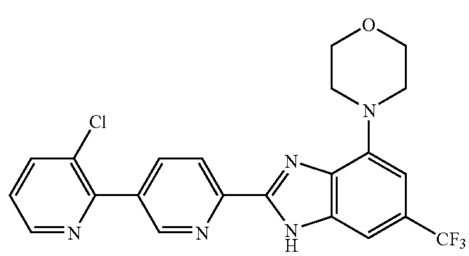 | 69 | (CD$_3$OD) δ: 9.09 (d, 1H), 8.65 (dd, 1H), 8.46 (d, 1H), 8.37 (dd, 1H), 8.05 (d, 1H), 7.59 (s, 1H), 7.50-7.46 (m, 1H), 7.04 (s, 1H), 4.01-3.97 (m, 4H), 3.53-3.49 (m, 4H) |
| 149 | 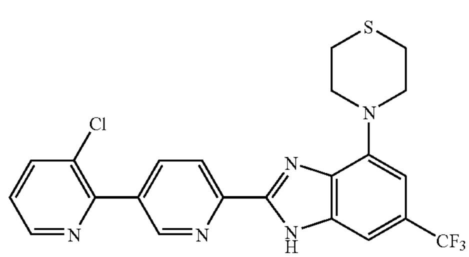 [SMILES: FC(F)(F)c1cc(N2CCOCC2)c2nc(-c3ccc(-c4ncccc4Cl)cn3)[nH]c2c1] | 58 | (CD$_3$OD) δ: 9.08 (d, 1H), 8.66 (dd, 1H), 8.52 (d, 1H), 8.37 (dd, 1H), 8.07 (d, 1H), 7.54-7.49 (m, 2H), 7.02 (s, 1H), 3.86-3.82 (m, 4H), 2.96-2.92 (m, 4H) |

| Cpds. | Structures | Yield | Spectrum Data (¹H NMR) |
|---|---|---|---|
| 150 | 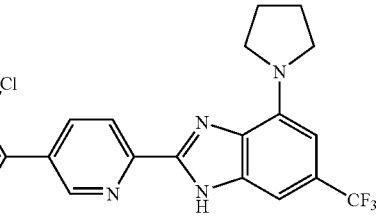 | 72 | (CD$_3$OD) δ: 9.04 (d, 1H), 8.64 (dd, 1H), 8.43 (d, 1H), 8.32 (dd, 1H), 8.04 (d, 1H), 7.49-7.45 (m, 2H), 7.32 (s, 1H), 3.89-3.84 (m, 4H), 2.20-2.15 (m, 4H) |

Example 151

Preparation of 3,5-dichloro-6'-(6-trifluoromethyl-1H-benzoimidazole-2-yl)-[2,3']bipyridine

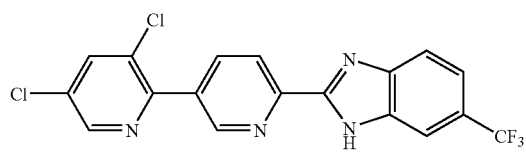 [SMILES: FC(F)(F)c1ccc2nc(-c3ccc(-c4ncc(Cl)cc4Cl)cn3)[nH]c2c1]

(1) Preparation of 3,5-dichloro-2-(6-methylpyridin-3-yl)pyridine

The same procedure as in (1) of Example 136 was performed to produce 3,5-dichloro-2-(6-methylpyridin-3-yl)pyridine (yield 72%).

¹H NMR (CD$_3$OD) δ: 8.76 (s, 1H), 8.67 (s, 1H), 8.20-8.11 (m, 2H), 7.47-7.43 (m, 1H), 2.61 (s, 3H)

(2) The same procedure as in Example 100 was performed to produce 3,5-dichloro-6'-(6-trifluoromethyl-1H-benzoimidazole-2-yl)-[2,3']bipyridine (yield 65%)

¹H NMR (CDCl$_3$) δ: 9.05 (s, 1H), 8.81 (d, 1H), 8.62 (s, 1H), 8.37 (d, 1H), 8.10 (s, 1H), 7.90 (s, 1H), 7.86 (d, 1H), 7.64 (d, 1H)

Examples 152 to 155

The same procedure as in (2) of Example 151 was performed to produce Compounds 152 to 155.

| Cpds. | Structures | Yield | Spectrum Data (¹H NMR) |
|---|---|---|---|
| 152 | 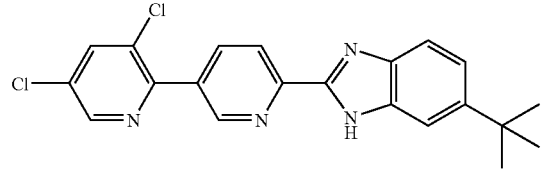 [SMILES: CC(C)(C)c1ccc2nc(-c3ccc(-c4ncc(Cl)cc4Cl)cn3)[nH]c2c1] | 91 | (CDCl$_3$) δ: 9.02-8.98 (m, 1H), 8.61 (s, 1H), 8.45-8.28 (m, 2H), 8.08 (s, 1H), 7.96-7.80 (m, 1H), 7.68-7.60 (m, 2H), 1.42 (s, 9H) |
| 153 | 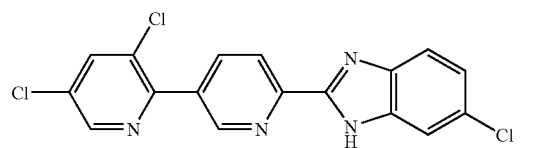 [SMILES: Clc1cnc(-c2ccc(-c3nc4ccc(Cl)cc4[nH]3)nc2)c(Cl)c1] | 92 | (CDCl$_3$) δ: 8.99 (s, 1H), 8.64 (d, 1H), 8.59 (s, 1H), 8.29 (d, 1H), 7.89 (s, 1H), 7.70 (s, 1H), 7.65 (d, 1H), 7.31-7.28 (m, 1H) |
| 154 | 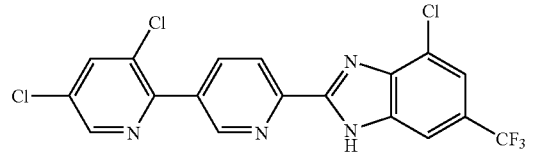 [SMILES: FC(F)(F)c1cc(Cl)c2nc(-c3ccc(-c4ncc(Cl)cc4Cl)cn3)[nH]c2c1] | 78 | (CDCl$_3$) δ: 9.08 (s, 1H), 8.64 (s, 1H), 8.59 (d, 1H), 8.33 (d, 1H), 7.91 (d, 2H), 7.60 (s, 1H) |
| 155 | 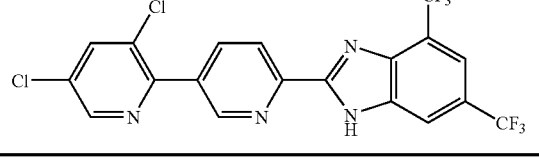 | 71 | ¹H NMR (DMSO-d$_6$) δ: 9.09 (s, 1H), 8.64 (s, 1H), 8.59 (d, 1H), 8.35 (d, 1H), 8.27 (s, 1H), 7.92 (s, 1H), 7.84 (s, 1H) |

Example 156

Preparation of 6'-(4,6-bistrifluoromethyl-1H-benzoimidazole-2-yl)-3-chloro-5-trifluoromethyl-[2,3']bipyridine

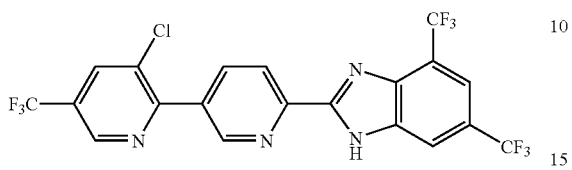

(1) Preparation of 3-chloro-5-trifluoromethyl-2-(6-methylpyridin-3-yl)pyridine The same procedure as in (1) of Example 136 was performed to produce 3-chloro-5-trifluoromethyl-2-(6-methylpyridin-3-yl)pyridine (yield 79%).

$^1$H NMR (CD$_3$OD) δ: 8.94 (s, 1H), 8.82 (s, 1H), 8.39 (s, 1H), 8.16 (d, 1H), 7.48 (d, 1H), 2.63 (s, 3H)

(2) Preparation of 5-(3-chloro-5-trifluoromethylpyridin-2-yl)pyridin-2-carboxylic acid The same procedure as in (1) of Example 104 was performed to produce 5-(3-chloro-5-trifluoromethylpyridin-2-yl)pyridin-2-carboxylic acid (yield 70%).

$^1$H NMR (CD$_3$OD) δ: 9.05-8.95 (m, 2H), 8.42-8.38 (m, 2H), 7.66-7.62 (m, 1H)

(3) Preparation of 6'-(4,6-bistrifluoromethyl-1H-benzoimidazole-2-yl)-3-chloro-5-trifluoromethyl-[2,3']bipyridine The same procedure as in (3) of Example 1 was performed to produce 6'-(4,6-bistrifluoromethyl-1H-benzoimidazole-2-yl)-3-chloro-5-trifluoromethyl-[2,3']bipyridine (yield 73%).

$^1$H NMR (CDCl$_3$) δ: 9.15 (s, 1H), 8.93 (s, 1H), 8.56 (d, 1H), 8.39-8.33 (m, 2H), 8.13 (s, 1H), 7.85 (s, 1H)

Example 157

Preparation of 6'-(6-methoxy-1H-benzoimidazole-2-yl)-3-chloro-5-trifluoromethyl-[2,3']bipyridine

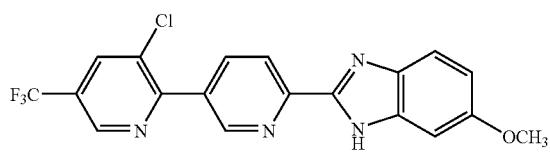 [SMILES: COc1ccc2nc(-c3ccc(-c4ncc(C(F)(F)F)cc4Cl)cn3)[nH]c2c1]

The same procedure as in (3) of Example 156 was performed to produce 6'-(6-methoxy-1H-benzoimidazole-2-yl)-3-chloro-5-trifluoromethyl-[2,3']bipyridine (yield 91%).

$^1$H NMR (CDCl$_3$) δ: 8.91 (s, 1H), 8.25-8.20 (m, 1H), 8.12 (s, 1H), 7.57 (d, 1H), 7.36 (s, 1H), 7.36-7.28 (m, 3H), 3.94 (s, 3H)

Example 158

Preparation of 3-trifluoromethyl-6'-(6-trifluoromethyl-1H-benzoimidazole-2-yl)-[2,3']bipyridine

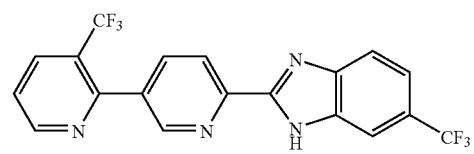

(1) Preparation of 3-trifluoromethyl-2-(6-methylpyridin-3-yl)pyridine

The same procedure as in (1) of Example 136 was performed to produce 3-trifluoromethyl-2-(6-methylpyridin-3-yl)pyridine (yield 82%).

$^1$H NMR (CDCl$_3$) δ: 8.88 (d, 1H), 8.67 (s, 1H), 8.12 (dd, 1H), 7.76 (dd, 1H), 7.54-7.49 (m, 1H), 7.29-7.28 (m, 1H), 2.66 (s, 3H)

(2) Preparation of 5-(3-trifluoromethylpyridin-2-yl)pyridin-2-ylcarboxylic acid The same procedure as in (1) of Example 104 was performed to produce 5-(3-trifluoromethylpyridin-2-yl)pyridin-2-ylcarboxylic acid (yield 75%).

$^1$H NMR (CD$_3$OD) δ: 8.92-8.89 (m, 1H), 8.79 (s, 1H), 8.34-8.27 (m, 2H), 8.15 (s, 1H), 7.73-7.68 (m, 1H)

(3) Preparation of 3-trifluoromethyl-6'-(6-trifluoromethyl-1H-benzoimidazole-2-yl)-[2,3']bipyridine The same procedure as in (3) of Example 1 was performed to produce 3-trifluoromethyl-6'-(6-trifluoromethyl-1H-benzoimidazole-2-yl)-[2,3']bipyridine (yield 94%).

$^1$H NMR (CDCl$_3$) δ: 8.94 (d, 1H), 8.84 (s, 1H), 8.61 (d, 1H), 8.19 (d, 1H), 8.11 (d, 1H), 8.10 (s, 1H), 8.08 (d, 1H), 7.61-7.54 (m, 2H)

Examples 159 to 168

The same procedure as in (3) of Example 158 was performed to produce Compounds 159 to 168.

| Cpds. | Structures | Yield | Spectrum Data ($^1$H NMR) |
|---|---|---|---|
| 159 | 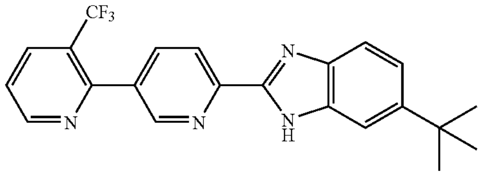 [SMILES: CC(C)(C)c1ccc2nc(-c3ccc(-c4ncccc4C(F)(F)F)cn3)[nH]c2c1] | 93 | (CDCl$_3$) δ: 8.91 (dd, 1H), 8.78 (d, 1H), 8.77-8.72 (br, 1H), 8.15 (dd, 1H), 8.05 (d, 1H), 7.75-7.65 (br, 2H), 7.53 (dd, 1H), 7.43 (d, 1H), 1.39 (s, 9H) |
| 160 | 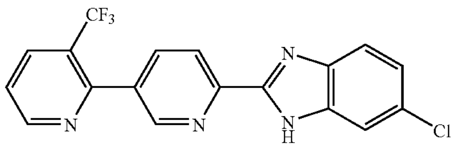 | 88 | (CDCl$_3$) δ: 8.92 (d, 1H), 8.80 (d, 1H), 8.53 (d, 1H), 8.16 (dd, 1H), 8.05 (dd, 1H), 7.65-7.56 (br, 2H), 7.54 (dd, 1H), 7.30 (dd, 1H) |
| 161 | 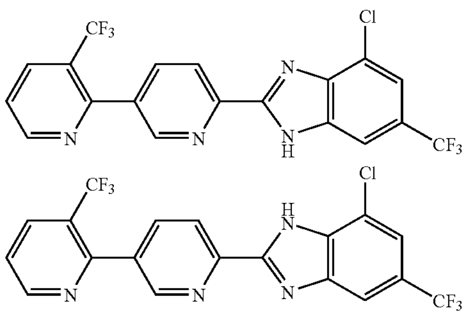 | 73 | (CDCl$_3$) δ: 8.89 (d, 1.2H), 8.79 (d, 0.8H), 8.62 (d, 0.4H), 8.50 (d, 0.6H), 8.13 (d, 1.0H), 8.07-8.01 (m, 1.6H), 7.70 (s, 0.4H), 7.54-7.49 (m, 2.0H) |
| 162 | 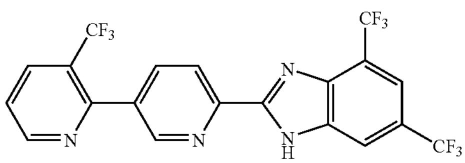 | 75 | (CDCl$_3$) δ: 8.95 (d, 1H), 8.86 (s, 1H), 8.60 (d, 1H), 8.25 (s, 1H), 8.19 (d, 1H), 8.13 (d, 1H), 7.86 (s, 1H), 7.60-7.56 (m, 1H) |
| 163 | 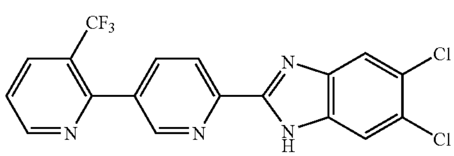 | 92 | (CD$_3$OD) δ: 8.92 (d, 1H), 8.83 (s, 1H), 8.41 (d, 1H), 8.33 (d, 1H), 8.11 (dd, 1H), 7.82 (s, 2H), 7.71 (dd, 1H) |
| 164 | 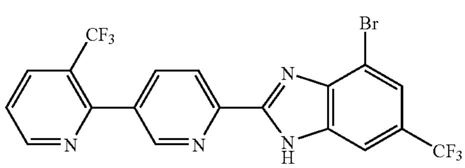 | 70 | (CD$_3$OD) δ: 8.93 (d, 1H), 8.87 (s, 1H), 8.59 (s, 1H), 8.35 (d, 1H), 8.14 (d, 1H), 7.94 (s, 1H), 7.76-7.69 (m, 2H) |
| 165 | 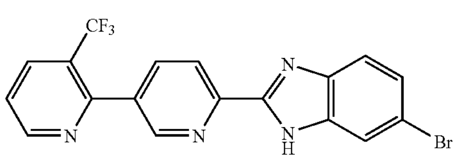 [SMILES: FC(F)(F)c1cccnc1-c1ccc(-c2nc3ccc(Br)cc3[nH]2)nc1] | 66 | (CD$_3$OD) δ: 8.90 (dd, 1H), 8.81 (d, 1H), 8.35 (dd, 1H), 8.29 (dd, 1H), 8.07 (dd, 1H), 7.80-7.70 (br, 1H), 7.67 (dd, 1H), 7.65-7.55 (br, 1H), 7.41 (dd, 1H) |
| 166 | 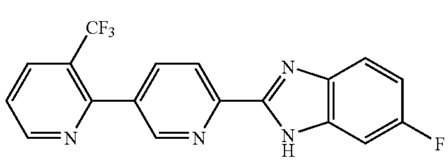 | 85 | (CD$_3$OD) δ: 8.91 (dd, 1H), 8.82 (d, 1H), 8.39-8.31 (m, 2H), 8.09 (dd, 1H), 7.71-7.65 (m, 2H), 7.35 (br, 1H), 7.09 (dd, 1H) |

| Cpds. | Structures | Yield | Spectrum Data ($^1$H NMR) |
|---|---|---|---|
| 167 | 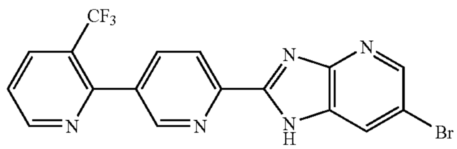 | 52 | (CDCl$_3$) δ: 9.79 (s, 1H), 8.91 (dd, 1H), 8.74 (d, 1H), 8.35 (dd, 1H), 8.15 (dd, 1H), 8.10 (dd, 1H), 8.03 (d, 1H), 7.54 (dd, 1H) |
| 168 | 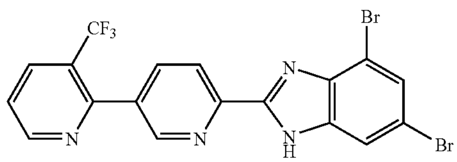 [SMILES: FC(F)(F)c1cccnc1-c1ccc(-c2nc3c(Br)cc(Br)cc3[nH]2)nc1] | 62 | (CD$_3$OD) δ: 8.90 (d, 1H), 8.82 (s, 1H), 8.52 (d, 1H), 8.32 (d, 1H), 8.09 (dd, 1H), 7.72 (d, 1H), 7.67 (dd, 1H), 7.59 (s, 1H) |

Example 169

Preparation of 6'-(6-morpholin-4-yl-1H-benzoimidazo-2-yl)-3-trifluoromethyl-[2,3']bipyridine

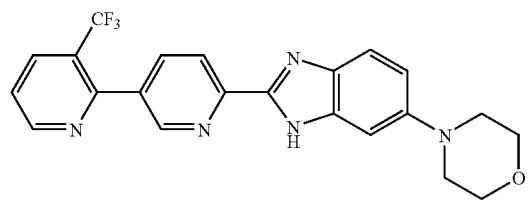

The same procedure as in Example 17 was performed to produce 6'-(6-morpholin-4-yl-1H-benzoimidazo-2-yl)-3-trifluoromethyl-[2,3']bipyridine (yield 67%).

$^1$H NMR (CD$_3$OD) δ: 8.90 (d, 1H), 8.80 (s, 1H), 8.33 (dd, 1H), 8.27 (dd, 1H), 8.07 (dd, 1H), 7.75-7.81 (br, 1H), 7.66 (dd, 1H), 7.65-7.55 (br, 1H), 7.41 (dd, 1H), 3.88-3.92 (m, 4H), 3.32-3.29 (m, 4H)

Example 170

Preparation of 6'-(4-morpholin-4-yl-6-trifluoromethyl-1H-benzoimidazole-2-yl)-3-trifluoromethyl-[2,3']bipyridine

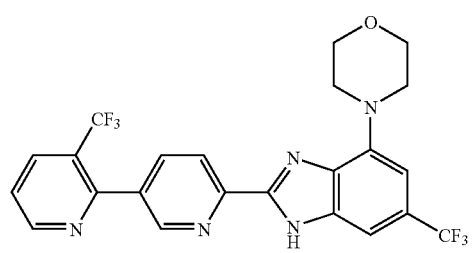 [SMILES: FC(F)(F)c1cc(N2CCOCC2)c2nc(-c3ccc(-c4ncccc4C(F)(F)F)cn3)[nH]c2c1]

The same procedure as in Example 169 was performed to produce 6'-(4-morpholin-4-yl-6-trifluoromethyl-1H-benzoimidazole-2-yl)-3-trifluoromethyl-[2,3']bipyridine (yield 67%).

$^1$H NMR (CDCl$_3$) δ: 10.94 (s, 1H), 8.92 (d, 1H), 8.79 (s, 1H), 8.53 (d, 1H), 8.15 (d, 1H), 8.06 (dd, 1H), 7.56-7.52 (m, 1H), 7.09 (s, 1H), 6.82 (s, 1H), 4.06-4.00 (m, 4H), 3.72-3.67 (m, 4H)

Example 171

Preparation of 6'-(6-chloro-1H-benzoimidazole-2-yl)-[2,3']bipyridine

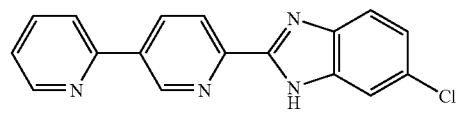

(1) Preparation of 2-(6-methylpyridin-3-yl)pyridine

The same procedure as in (1) of Example 136 was performed to produce 2-(6-methylpyridin-3-yl)pyridine (yield 67%).

$^1$H NMR (CDCl$_3$) δ: 9.08 (d, 1H), 8.72 (dd, 1H), 8.24 (dd, 1H), 7.79-7.75 (m, 2H), 7.62-7.45 (m, 1H), 7.30-7.27 (m, 1H), 2.64 (s, 3H)

(2) Preparation of 5-(pyridin-2-yl)pyridin-2-carboxylic acid

The same procedure as in (1) of Example 104 was performed to produce 5-(pyridin-2-yl)pyridin-2-carboxylic acid (yield 77%).

$^1$H NMR (CD$_3$OD) δ: 9.30 (s, 1H), 8.73 (d, 1H), 8.62 (d, 1H), 8.30 (d, 1H), 8.07-7.98 (m, 2H), 7.49 (d, 1H)

(3) Preparation of 6'-(6-chloro-1H-benzoimidazole-2-yl)-[2,3']bipyridine

The same procedure as in (3) of Example 1 was performed to produce 6'-(6-chloro-1H-benzoimidazole-2-yl)-[2,3']bipyridine (yield 90%).

$^1$H NMR (CDCl$_3$) δ: 7.80-7.78 (m, 1H), 7.70-7.67 (m, 1H), 7.62-7.58 (m, 1H), 7.46-7.45 (m, 1H), 7.32-7.13 (m, 6H)

Examples 172 and 173

The same procedure as in (3) of Example 171 was performed to produce Compounds 172 and 173.

| Cpds. | Structures | Yield | Spectrum Data (¹H NMR) |
|---|---|---|---|
| 172 | 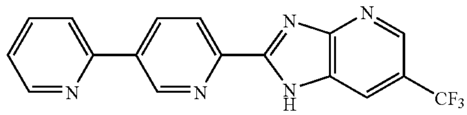 [SMILES: FC(F)(F)c1cnc2nc(-c3ccc(-c4ccccn4)cn3)[nH]c2c1] | 68 | (CDCl₃) δ: 8.91 (d, 1H), 7.74 (s, 1H), 7.67-7.63 (m, 2H) 7.61 (d, 1H), 7.56-7.43 (m, 4H) |
| 173 | 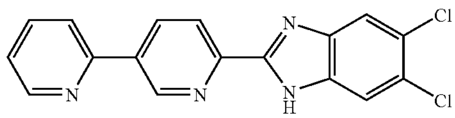 [SMILES: Clc1cc2nc(-c3ccc(-c4ccccn4)cn3)[nH]c2cc1Cl] | 81 | (CD₃OD) δ: 9.35 (d, 1H), 8.71 (d, 1H), 8.55 (dd, 1H), 8.38 (d, 1H), 8.05-7.96 (m, 2H), 7.86 (s, 1H), 7.77 (s, 1H), 7.46 (dd, 1H) |

Example 174

Preparation of 6-tert-butyl-2-(6-naphthalen-1-ylpyridin-3-yl)-1H-benzoimidazole

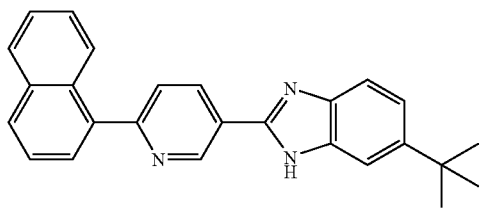 [SMILES: CC(C)(C)c1ccc2nc(-c3ccc(-c4cccc5ccccc45)nc3)[nH]c2c1]

The same procedure as in Example 100 was performed to produce 6-tert-butyl-2-(6-naphthalen-1-ylpyridin-3-yl)-1H-benzoimidazole (yield 53%).

¹H NMR (CD₃OD) δ: 9.40 (s, 1H), 8.62 (d, 1H), 8.00-7.95 (m, 5H), 7.58-7.46 (m, 6H), 1.28 (s, 9H)

Examples 175 to 177

The same procedure as in Example 174 was performed to produce Compounds 175 to 177.

| Cpds. | Structures | Yield | Spectrum Data (¹H NMR) |
|---|---|---|---|
| 175 | 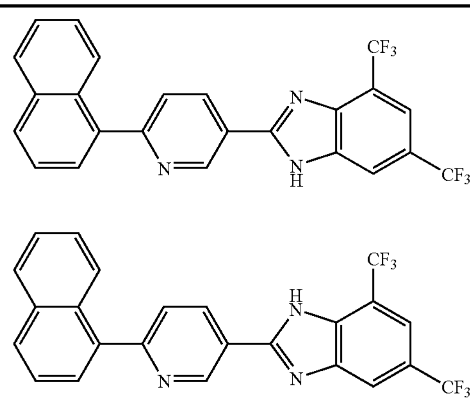 | 80 | (CD₃OD) δ: 9.53 (d, 0.8H), 9.19 (d, 0.2H), 8.81 (dd, 0.8H), 8.45 (dd, 0.2H), 8.23 (s, 0.8H), 8.20 (s, 0.2H), 8.04-8.00 (m, 3.0H), 7.94-7.90 (m, 1.0H), 7.85 (s, 0.8H), 7.82 (s, 0.2H), 7.70-7.63 (m, 2.0H), 7.58-7.50 (m, 2.0H) |
| 176 | 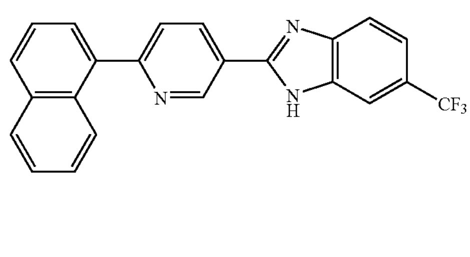 [SMILES: FC(F)(F)c1ccc2nc(-c3ccc(-c4cccc5ccccc45)nc3)[nH]c2c1] | 89 | (CD₃OD) δ: 9.45 (d, 1H), 8.66 (dd, 1H), 8.03-7.96 (m, 4H), 7.89 (dd, 1H), 7.69-7.53 (m, 6H) |
| 177 | 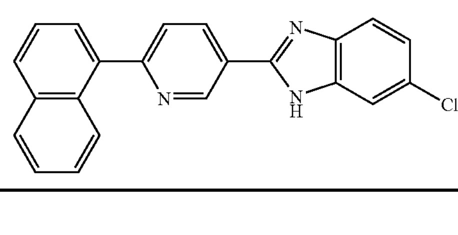 | 90 | (CD₃OD) δ: 9.41 (d, 1H), 8.64 (dd, 1H), 8.00-7.95 (m, 3H), 7.89 (d, 1H), 7.68-7.53 (m, 6H), 7.31 (d, 1H) |

Example 178

Preparation of 2-(4-pyrrol-1-ylphenyl]-6-trifluoromethyl-1H-benzoimidazole

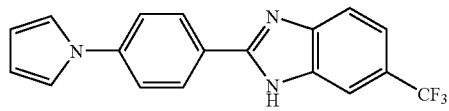 [SMILES: FC(F)(F)c1ccc2nc(-c3ccc(-n4cccc4)cc3)[nH]c2c1]

The same procedure as in (3) of Example 1 was performed to produce 2-(4-pyrrol-1-ylphenyl]-6-trifluoromethyl-1H-benzoimidazole (yield 77%).

$^1$H NMR (CDCl$_3$) δ: 8.12 (d, 2H, J=8.7 Hz), 7.92 (s, 1H), 7.69 (d, 1H, J=8.6 Hz), 7.54-7.49 (m, 3H), 7.15-7.14 (m, 2H), 6.40-6.38 (m, 2H)

Examples 179 to 200

The same procedure as in Example 178 was performed to produce Compounds 179 to 200.

| Cpds. | Structures | Yield | Spectrum Data ($^1$H NMR) |
|---|---|---|---|
| 179 | 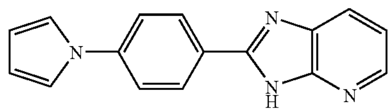 [SMILES: c1cnc2[nH]c(-c3ccc(-n4cccc4)cc3)nc2c1] | 48 | (CDCl$_3$) δ: 8.37-8.36 (m, 1H), 8.25 (d, 1H, J = 8.2 Hz), 8.15 (d, 2H, J = 8.1 Hz), 7.47 (d, 2H, J = 8.1 Hz), 7.30-7.28 (m, 1H), 7.16-7.14 (m, 2H), 6.39-6.36 (m, 2H) |
| 180 | 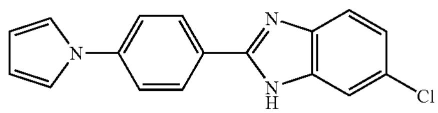 [SMILES: Clc1ccc2nc(-c3ccc(-n4cccc4)cc3)[nH]c2c1] | 81 | (CDCl$_3$) δ: 8.09 (d, 2H, J = 8.7 Hz), 7.63 (s, 1H), 7.57 (d, 1H, J = 8.6 Hz), 7.51 (d, 2H, J = 8.7 Hz), 7.27-7.24 (m, 1H), 7.16-7.15 (m, 2H), 6.40-6.38 (m, 2H) |
| 181 | 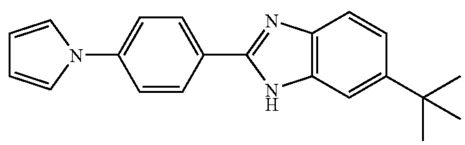 [SMILES: CC(C)(C)c1ccc2nc(-c3ccc(-n4cccc4)cc3)[nH]c2c1] | 69 | (CDCl$_3$) δ: 8.10 (d, 2H, J = 8.7 Hz), 7.64 (s, 1H), 7.56 (d, 1H, J = 8.6 Hz), 7.45 (d, 2H, J = 8.7 Hz), 7.35 (d, 1H, J = 8.5 Hz), 7.12-7.10 (m, 2H), 6.37-6.36 (m, 2H), 1.37 (s, 9H) |
| 182 | 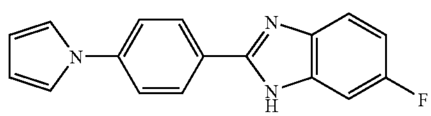 | 68 | (CDCl$_3$) δ: 8.08 (d, 2H, J = 8.6 Hz), 7.52 (d, 2H, J = 8.6 Hz), 7.42 (s, 1H), 7.34 (d, 1H, J = 8.5 Hz), 7.16-7.15 (m, 2H), 7.07-7.02 (m, 1H), 6.40-6.37 (m, 2H) |
| 183 | 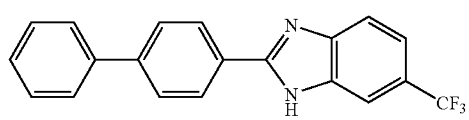 [SMILES: FC(F)(F)c1ccc2nc(-c3ccc(-c4ccccc4)cc3)[nH]c2c1] | 92 | (CDCl$_3$) δ: 8.15 (d, 2H, J = 8.4 Hz), 7.93 (s, 1H), 7.74-7.69 (m, 3H), 7.63 (d, 2H, J = 7.0 Hz), 7.53 (d, 1H, J = 8.4 Hz), 7.49-7.39 (m, 3H) |
| 184 | 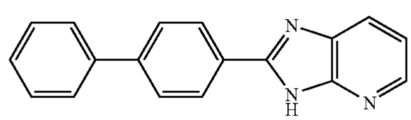 [SMILES: c1ccc(-c2ccc(-c3nc4cccnc4[nH]3)cc2)cc1] | 69 | (CDCl$_3$) δ: 8.38 (m, 1H), 8.31 (d, 2H, J = 8.2 Hz), 7.83 (d, 2H, J = 8.2 Hz), 7.73-7.64 (m, 4H), 7.51-7.43 (m, 2H), 7.34-7.30 (m, 1H) |
| 185 | 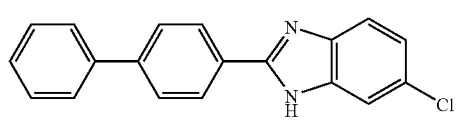 [SMILES: Clc1ccc2nc(-c3ccc(-c4ccccc4)cc3)[nH]c2c1] | 85 | (CDCl$_3$) δ: 8.11 (d, 2H, J = 8.5 Hz), 7.72 (d, 2H, J = 8.5 Hz), 7.64-7.57 (m, 4H), 7.50-7.36 (m, 3H), 7.27-7.24 (m, 1H) |
| 186 | 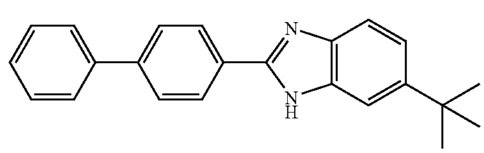 | 79 | (CDCl$_3$) δ: 8.12 (d, 2H, J = 8.4 Hz), 7.57 (d, 1H, J = 1.5 Hz), 7.52-7.47 (m, 5H), 7.42-7.33 (m, 3H), 7.28-7.25 (m, 1H), 1.29 (s, 9H) |

-continued
| Cpds. | Structures | Yield | Spectrum Data (¹H NMR) |
|---|---|---|---|
| 187 | 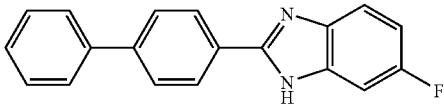 | 88 | (CDCl$_3$) δ: 8.10 (d, 2H, J = 8.3 Hz), 7.72 (d, 2H, J = 8.3 Hz), 7.60 (d, 2H, J = 7.5 Hz), 7.59-7.56 (m, 1H), 7.45 (d, 2H, J = 7.5 Hz), 7.41-7.33 (m, 2H), 7.07-7.00 (m, 1H) |
| 188 | 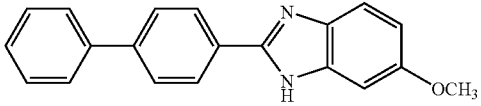 | 90 | (CDCl$_3$) δ: 8.10 (d, 2H, J = 8.4 Hz), 7.73-7.69 (m, 2H), 7.64-7.57 (m, 3H), 7.46-7.34 (m, 4H), 6.95-6.92 (m, 1H), 3.86 (s, 3H) |
| 189 | 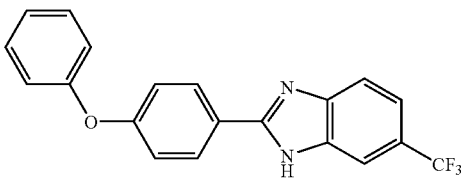 [SMILES: FC(F)(F)c1ccc2nc(-c3ccc(Oc4ccccc4)cc3)[nH]c2c1] | 76 | (CDCl$_3$) δ: 8.00 (d, 2H, J = 8.8 Hz), 7.86 (s, 1H), 7.64 (d, 1H, J = 8.4 Hz), 7.49 (d, 1H, J = 8.4 Hz), 7.47-7.36 (m, 2H), 7.21-7.16 (m, 1H), 7.07-7.04 (m, 4H) |
| 190 | 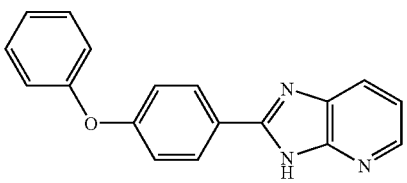 [SMILES: c1ccc(Oc2ccc(-c3nc4cccnc4[nH]3)cc2)cc1] | 60 | (CDCl$_3$) δ: 8.30 (br, 1H), 8.18-8.14 (m, 3H), 7.44-7.39 (m, 2H), 7.31-7.29 (m, 1H), 7.22 (d, J = 7.4 Hz, 1H), 7.18-7.10 (m, 4H) |
| 191 | 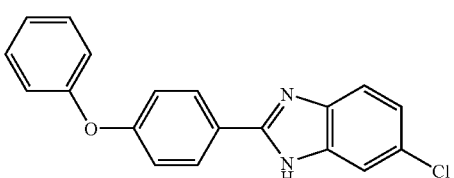 | 76 | (CDCl$_3$) δ: 8.00 (d, 2H, J = 8.8 Hz), 7.54 (d, 1H, J = 1.5 Hz), 7.49 (d, 1H, J = 8.6 Hz), 7.40-7.34 (m, 2H), 7.23-7.14 (m, 2H), 7.06-6.97 (m, 4H) |
| 192 | 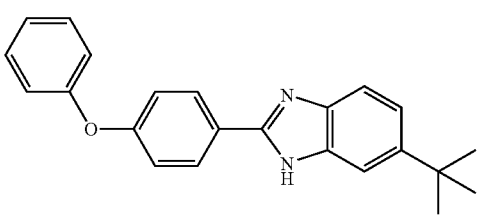 [SMILES: CC(C)(C)c1ccc2nc(-c3ccc(Oc4ccccc4)cc3)[nH]c2c1] | 77 | (CDCl$_3$) δ: 8.02 (d, 2H, J = 8.8 Hz), 7.62 (s, 1H), 7.54 (d, 1H, J = 8.6 Hz), 7.40-7.31 (m, 3H), 7.16 (t, 1H, J = 7.4 Hz), 7.08-7.02 (m, 4H), 1.37 (s, 9H) |
| 193 | 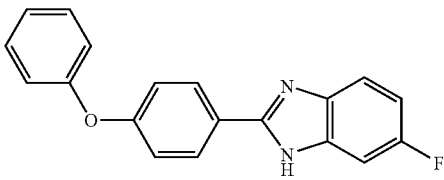 [SMILES: Fc1ccc2nc(-c3ccc(Oc4ccccc4)cc3)[nH]c2c1] | 83 | (CDCl$_3$) δ: 8.00 (d, 2H, J = 5.0 Hz), 7.50-7.45 (m, 1H), 7.41-7.36 (m, 2H), 7.30-7.26 (m, 1H), 7.20-7.16 (m, 1H), 7.08-7.01 (m, 5H) |
| 194 | 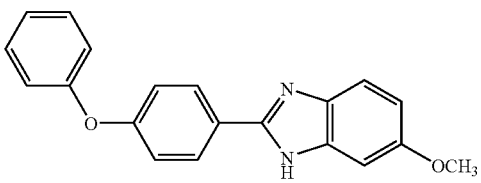 [SMILES: COc1ccc2nc(-c3ccc(Oc4ccccc4)cc3)[nH]c2c1] | 83 | (CDCl$_3$) δ: 7.98 (d, 2H, J = 8.8 Hz), 7.50 (d, 1H, J = 8.8 Hz), 7.42-7.35 (m, 2H), 7.18-7.13 (m, 1H), 7.08-7.01 (m, 5H), 6.89 (dd, 1H, J = 8.8, 2.4 Hz), 3.83 (s, 3H) |

| Cpds. | Structures | Yield | Spectrum Data ($^1$H NMR) |
|---|---|---|---|
| 195 | 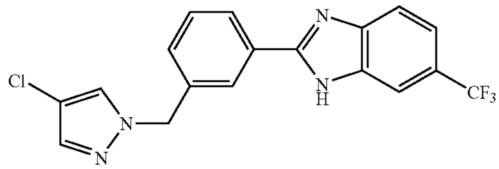 [SMILES: FC(F)(F)c1ccc2nc(-c3cccc(Cn4cc(Cl)cn4)c3)[nH]c2c1] | 72 | (CD$_3$OD) δ: 8.19-8.15 (m, 2H), 8.03-7.96 (m, 2H), 7.87-7.81 (m, 1H), 7.68-7.56 (m, 3H), 7.55-7.52 (m, 1H), 5.52 (d, 2H) |
| 196 | 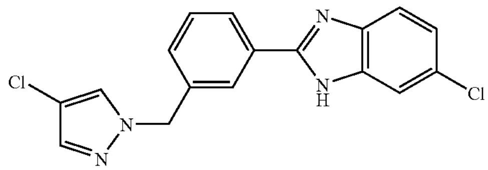 [SMILES: Clc1ccc2nc(-c3cccc(Cn4cc(Cl)cn4)c3)[nH]c2c1] | 75 | (CD$_3$OD) δ: 8.15-8.11 (m, 2H), 7.99 (s, 1H), 7.71-7.62 (m, 4H), 7.52 (d, 1H), 7.36 (d, 1H), 5.53 (s, 2H) |
| 197 | 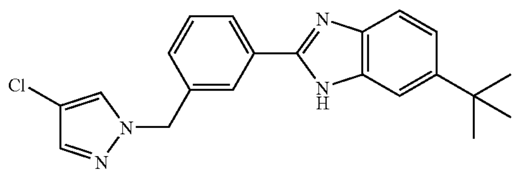 [SMILES: CC(C)(C)c1ccc2nc(-c3cccc(Cn4cc(Cl)cn4)c3)[nH]c2c1] | 80 | (CD$_3$OD) δ: 8.15-8.12 (m, 2H), 7.99 (s, 1H), 7.73 (s, 1H), 7.68-7.60 (m, 3H), 7.50-7.48 (m, 2H), 5.54 (s, 2H), 1.53 (s, 9H) |
| 198 | 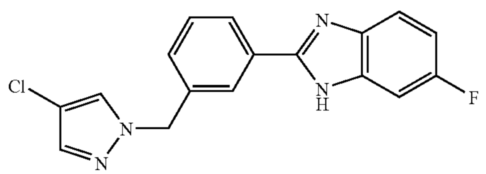 [SMILES: Fc1ccc2nc(-c3cccc(Cn4cc(Cl)cn4)c3)[nH]c2c1] | 71 | (CD$_3$OD) δ: 8.15-8.11 (m, 2H), 7.99 (s, 1H), 7.72-7.63 (m, 3H), 7.52 (d, 1H), 7.41 (d, 1H), 7.21-7.12 (m, 1H), 5.54 (s, 2H) |
| 199 | 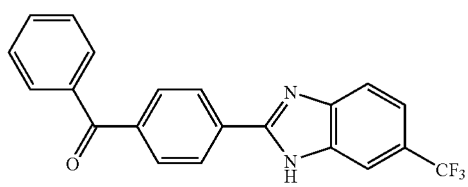 [SMILES: O=C(c1ccccc1)c1ccc(-c2nc3ccc(C(F)(F)F)cc3[nH]2)cc1] | 86 | (CD$_3$OD) δ: 8.39 (d, 2H), 8.10-8.06 (m, 3H), 7.94 (d, 2H), 7.90 (s, 1H), 7.79 (d, 1H), 7.72-7.68 (m, 3H) |
| 200 | 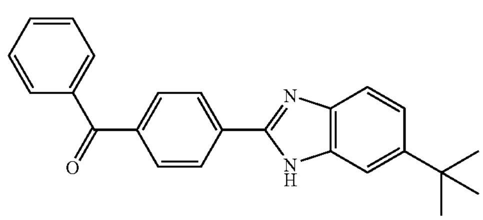 [SMILES: CC(C)(C)c1ccc2nc(-c3ccc(C(=O)c4ccccc4)cc3)[nH]c2c1] | 82 | (CD$_3$OD) δ: 8.35 (d, 2H), 8.05 (d, 2H), 7.94 (d, 2H), 7.82-7.77 (m, 2H), 7.71-7.66 (m, 3H), 7.54 (d, 1H), 1.54 (s, 9H) |

Example 201

Preparation of 2-[4-(3-chloropyridin-2-yl)phenyl]-6-trifluoromethyl-1H-benzoimidazole chloride 500 mg (1.34 mmol) of 2-[4-(3-chloropyridin-2-yl)phenyl]-6-trifluoromethyl-1H-benzoimidazole was dissolved in 10 mL of diethylether, followed by stirring for 30 min at a subzero temperature. After saturation with gaseous hydrochloric acid, the solution was stirred for an additional one hour at a subzero temperature. A white precipitate thus obtained was filtered and dried for 24 hours in a vacuum condition to give 513 mg of 2-[4-(3-chloropyridin-2-yl)phenyl]-6-trifluoromethyl-1H-benzoimidazole chloride.

$^1$H NMR (CD$_3$OD) δ: 8.75 (d, 1H), 8.38 (d, 2H), 8.29 (d, 1H), 8.23 (s, 1H), 8.13 (d, 2H), 8.10 (d, 1H), 7.97 (d, 1H), 7.70 (dd, 1H)

mp: 291~293° C.

Example 202

Preparation of 6-tert-butyl-2-[4-(3-chloropyridin-2-yl)phenyl]-1H-benzoimidazole chloride The same procedure as in Example 201 was performed to produce 500 mg of 6-tert-butyl-2-[4-(3-chloropyridin-2-yl)phenyl]-1H-benzoimidazole chloride.

$^1$H NMR (CD$_3$OD) δ: 8.73 (d, 1H), 8.30 (d, 2H), 8.26 (d, 1H), 8.10 (d, 2H), 7.83 (d, 2H), 7.81 (s, 1H), 7.67 (dd, 1H), 1.47 (s, 9H)

mp: 189~190° C.

Example 203

Preparation of 6-tert-butyl-2-[4-(3-chloropyridin-2-yl)naphthalen-1-yl]-1H-benzoimidazole chloride The same procedure as in Example 201 was performed to produce 510 mg of 6-tert-butyl-2-[4-(3-chloropyridin-2-yl)naphthalen-1-yl]-1H-benzoimidazole chloride.

$^1$H NMR (CD$_3$OD) δ: 8.68 (d, 1H), 8.20 (d, 1H), 8.16-8.11 (m, 2H), 7.83-7.72 (m, 5H), 7.66-7.62 (m, 2H), 7.54 (d, 1H), 1.41 (s, 9H)

mp: 208~214° C.

Example 204

Preparation of 6'-(4,6-bistrifluoromethyl-1H-benzoimidazole-2-yl)-3-chloro[2,3']bipyridine chloride The same procedure as in Example 201 was performed to produce 520 mg of 6'-(4,6-bistrifluoromethyl-1H-benzoimidazole-2-yl)-3-chloro[2,3']bipyridine chloride.

$^1$H NMR (CD$_3$OD) δ: 9.03 (s, 1H), 8.61-8.53 (m, 2H), 8.30 (d, 1H), 8.15 (s, 1H), 8.03 (d, 1H), 7.77 (s, 1H), 7.47-7.43 (m, 1H)

mp: 133-135° C.

Example 205

Preparation of 3-trifluoromethyl-6'-(6-trifluoromethyl-1H-benzoimidazole-2-yl)-[2,3']bipyridine chloride The same procedure as in Example 201 was performed to produce 495 mg of 3-trifluoromethyl-6'-(6-trifluoromethyl-1H-benzoimidazole-2-yl)-[2,3']bipyridine chloride.

$^1$H NMR (CD$_3$OD) δ: 9.00 (s, 1H), 8.91 (d, 1H), 8.46 (d, 1H), 8.35-8.28 (m, 2H), 8.17 (s, 1H), 8.04 (d, 1H), 7.90 (d, 1H), 7.73-7.69 (m, 1H)

mp: 234~240° C.

Example 206

Preparation of 6-tert-butyl-2-[4-(3-chloropyridin-2-yl)phenyl]-1H-benzoimidazole sodium salt A solution of 100 mg (0.28 mmol) of 6-tert-butyl-2-[4-(3-chloropyridin-2-yl)phenyl]-1H-benzoimidazole in 2.8 mL of 0.1N sodium hydroxide and 0.5 mL of methanol was stirred at room temperature for 30 min and vacuum concentrated to produce 107 mg of 6-tert-butyl-2-[4-(3-chloropyridin-2-yl)phenyl]-1H-benzoimidazole sodium salt as a pale yellow precipitate.

$^1$H NMR (CD$_3$OD) δ: 8.60 (d, 1H), 8.22 (d, 2H), 8.04 (d, 1H), 7.85 (d, 2H), 7.65 (s, 1H), 7.57 (d, 1H), 7.48-7.38 (m, 2H), 1.43 (s, 9H).

mp: 317~324° C.

Example 207

Preparation of 3-trifluoromethyl-6'-(6-trifluoromethyl-1H-benzoimidazole-2-yl)-[2,3']bipyridine sulfate 1.0 g (2.45 mmol) of a pyridine compound was dissolved in 30 mL of acetone and stirred for 30 min at a subzero temperature. To this, a dilution of 0.16 mL (2.94 mmol) of sulfate in 20 mL of acetone was dropwisely added over 10 min. Stirring for one hour at a subzero temperature produced a white precipitate which was then vacuum dried to produce 1.22 g of 3-trifluoromethyl-6'-(6-trifluoromethyl-1H-benzoimidazole-2-yl)-[2,3']bipyridine sulfate.

$^1$H NMR (CD$_3$OD) δ: 9.07 (s, 1H), 8.99 (d, 1H), 8.55 (d, 1H), 8.46 (d, 1H), 8.37 (dd, 1H), 8.26 (s, 1H), 8.12 (d, 1H), 7.97 (d, 1H), 7.80-7.74 (m, 1H)

Example 208

Preparation of 3-trifluoromethyl-6'-(6-trifluoromethyl-1H-benzoimidazole-2-yl)-[2,3']bipyridine phosphate 1.0 g (2.45 mmol) of a bipyridine compound was dissolved in 30 mL of acetone and stirred for 30 min at a freezing temperature. To this, a dilution of 0.16 mL (2.94 mmol) of phosphoric acid in 20 mL of acetone was added dropwise over 10 min. Stirring for one hour at a freezing temperature produced a white precipitate which was then vacuum dried to produce 1.23 g of 3-trifluoromethyl-6'-(6-trifluoromethyl-1H-benzoimidazole-2-yl)-[2,3']bipyridine phosphate.

$^1$H NMR (CD$_3$OD) δ: 8.92 (dd, 1H), 8.85 (s, 1H), 8.45 (d, 1H), 8.34 (d, 1H), 8.14 (dd, 1H), 8.00 (s, 1H), 7.83 (d, 1H), 7.72-7.70 (m, 1H), 7.59 (d, 1H)

Example 209

Preparation of 3-trifluoromethyl-6'-(6-trifluoromethyl-1H-benzoimidazole-2-yl)-[2,3']bipyridine methanesulfonate 1.0 g (2.45 mmol) of a bipyridine compound was dissolved in 30 mL of diethylether and stirred for 30 min under a glacial condition. To this, a dilution of 0.19 mL (2.94 mmol) of methanesulfonic acid in 20 mL of diethylether was added dropwise over 10 min. Stirring for one hour at a freezing temperature produced a white precipitate which was then vacuum dried to produce 1.25 g of 3-trifluoromethyl-6'-(6-trifluoromethyl-1H-benzoimidazole-2-yl)-[2,3']bipyridine methanesulfonate.

$^1$H NMR (CD$_3$OD) δ: 9.05 (s, 1H), 8.96 (d, 1H), 8.52 (d, 1H), 8.41-8.32 (m, 2H), 8.24 (s, 1H), 8.10 (d, 1H), 7.95 (d, 1H), 7.76 (dd, 1H), 2.72 (s, 3H)

Example 210

Preparation of 3-trifluoromethyl-6'-(6-trifluoromethyl-1H-benzoimidazole-2-yl)-[2,3']bipyridine benzenesulfonate 1.0 g (2.45 mmol) of a bipyridine compound was dissolved in 30 mL of diethylether and stirred for 30 min at a freezing temperature. To this, a dilution of 0.85 mg (5.39 mmol) of benzenesulfonic acid in 20 mL of diethylether was added dropwise over 10 min. Stirring for one hour at a freezing temperature produced a white precipitate which was then vacuum dried to produce 1.39 g of 3-trifluoromethyl-6'-(6-trifluoromethyl-1H-benzoimidazole-2-yl)-[2,3']bipyridine benzenesulfonate.

$^1$H NMR (CD$_3$OD) δ: 9.07 (s, 1H), 9.00 (d, 1H), 8.53 (d, 1H), 8.49 (d, 1H), 8.31 (d, 2H), 8.23 (s, 1H), 8.10 (d, 1H), 7.97 (d, 1H), 7.84-7.80 (m, 6H), 7.44-7.38 (m, 7.5H)

Experimental Example 1

Assay for Inhibitory Activity Against Vanilloid Receptor

1) Preparation of Test Compounds

Each of the compounds synthesized in the examples were dissolved in dimethyl sulfoxide (DMSO) at a concentration of 10 mM. For use in the assay for inhibitory activity against patch clamp activity, the solutions were diluted to a concentration of 1 μM with the same physiological saline as in the pipette solution of Table 1, below.

2) Assay for Inhibitory Activity Against VR1 Patch Clamp Activity

In this experiment, changes in VR1 activity were recorded in current using an electrophysiological technique.

For use in this experiment, a rat TRPV1 cDNA was transfected into a subcultured HEK293 strain with the aid of lipofectamin.

The rat TRPV1 gene-transfected HEK293 cells were detached from the cell culture dishes with trypsin and distributed on a patch clamp recording chamber.

A cover glass slip on the bottom of the patch clamp recording chamber was treated for 15 min or longer with a 50% poly-L-lysine solution so that the HEK cells would readily adhere thereto. Cellular membranes were ruptured at room temperature (~25° C.) from randomly selected HEK cells to perform an inside-out patch clamp technique. 10 μM of capsaicin was fed into the chamber (cytoplasmic side) to activate a capsaicin current through the VR1. When the capsaicin current reached a stable stage, each compound was added along with 10 μM of capsaicin to record the inhibitory activity of the compounds with regard to the current. The inhibition was expressed as percentages. Because the capsaicin current showed rapid run-down in the presence of calcium ions across the membrane, experimental solutions comprising the ion compositions of Table 1 were used to prevent the run-down and record the inhibitory activity of effective compounds.

TABLE 1

Experimental Solution Composition for Capsaicin Current Recordings

| (in mM) | Pipette Solution | Bath Solution |
|---|---|---|
| NaCl | 140 | 140 |
| HEPES | 10 | 10 |
| EGTA | 0 | 2 |
| pH 7.3 adjusted with | NMG | NMG |

Detected current was amplified using a Digidata 1200B A/D converter and an Axopatch 1D amplifier (Axon instruments Inc.), and the data were recorded and analyzed with the aid of a computer. The inhibitory activity of each compound was expressed as a percentage relative to the capsaicin current immediately before the administration of each compound.

TABLE 2

Assay for Inhibitory Activity of Test Compounds Against VR1 Activity

| Cpds | Inhibition % (1 μM) |
|---|---|
| 1 | 100 |
| 2 | 45 |
| 3 | 100 |
| 5 | 10 |
| 6 | 94 |
| 8 | 41 |
| 10 | 80 |
| 29 | 50 |
| 30 | 96 |
| 31 | 66 |
| 32 | 78 |
| 33 | 10 |
| 34 | 16 |
| 67 | 80 |
| 70 | 45 |
| 104 | 86 |
| 105 | 78 |
| 107 | 97 |
| 115 | 71 |
| 116 | 30 |
| 117 | 80 |
| 118 | 93 |
| 121 | 76 |
| 126 | 87 |
| 138 | 73 |
| 139 | 89 |
| 151 | 84 |
| 158 | 69 |
| 161 | 58 |
| 162 | 99 |
| 178 | 20 |
| 179 | 100 |
| 181 | 40 |
| 183 | 17 |
| 189 | 90 |
| 191 | 60 |
| 193 | 50 |
| 194 | 30 |

Experimental Example 2

Calcium Influx of Vanilloid Receptor

Experiments for calcium influx were performed to measure the activity of the compounds as antagonists.

1) Cell Culture

The cell strain hVR1-HEK293 is the human embryonic kidney (HEK) 293 Tet-on cell transfected with a human vanilloid-1 gene (pTRE2hyg-hVR1, 7.8 kb), which is capable of controlling the expression of VR1 according to the administration of deoxycycline, a tetracycline derivative analog. In a medium supplemented with deoxycycline two days before calcium influx experiments, the cell strain was cultured to induce the expression of VR1. After being grown to a confluency of about 80% in T75 flasks, hVR1-HEK293 was detached from the flask using trypsin. Cells harvested by centrifugation were suspended in a medium supplemented with 1 μg/mL of deoxycycline and diluted to a density of 2-4×10⁵ cells/mL, after which a 100 μL aliquot of the cell suspension was added to each well of 96 well black plates. Before the measurement of calcium influx, the cells were incubated for two days at 37° C. in a 5% $CO_2$ incubator.

2) Preparation of Compound Samples

For use in calcium influx experiments, each compound was dissolved in dimethyl sulfoxide (DMSO).

3) Measurement of Calcium Influx

To measure an intracellular calcium influx, cells were incubated at 37° C. for 90 min in a medium containing the calcium indicator Fluo-3/AM so as to allow the fluorescent dye to penetrate into the cells. Then, the cells were washed three times with D-PBS (Dulbecco's phosphate buffered saline) containing 10 mM HEPES to remove the fluorescent dye which remained outside. 193 μL aliquot of D-PBS was added to each well, followed by the addition of various concentrations of compounds thereto. In order to measure the antagonistic activity of the compounds, calcium influx was induced by treatment with 1 μM capsaicin. The inhibitory effect of each compound on 1 μM capsaicin-induced intracellular calcium influx according to compound concentration was measured using a fluorescent analyzer and the data thus obtained were analyzed on the basis of the Hill's equation.

4) Measurement Results

TABLE 3

Inhibitory Activity of Compounds Against Calcium Influx

| Cpds | Inhibitory Activity $IC_{50}$ (nM) |
|---|---|
| 1 | 130 |
| 2 | 8570 |
| 3 | 61 |
| 5 | 6038 |
| 6 | 11 |
| 8 | 31 |
| 10 | 114 |
| 12 | 70 |
| 13 | 289 |
| 14 | 168 |
| 25 | 100 |
| 29 | 4 |
| 30 | 23 |
| 31 | 8 |
| 32 | 13 |
| 33 | 10 |
| 34 | 26 |
| 35 | 39 |
| 36 | 94 |
| 37 | 75 |
| 38 | 454 |
| 39 | 19 |
| 47 | 82 |
| 48 | 160 |
| 49 | 284 |
| 50 | 292 |
| 51 | 246 |
| 52 | 1404 |
| 53 | 145 |
| 56 | 22 |
| 58 | 145 |
| 59 | 296 |
| 60 | 150 |
| 67 | 122 |
| 82 | 263 |
| 97 | 644 |
| 104 | 31 |
| 105 | 24 |
| 106 | 275 |
| 107 | 17 |
| 113 | 363 |
| 117 | 525 |
| 118 | 313 |
| 126 | 105 |
| 129 | 3963 |
| 130 | 436 |
| 136 | 952 |
| 137 | 569 |
| 138 | 16 |
| 139 | 38 |
| 140 | 66 |
| 141 | 2402 |
| 151 | 97 |
| 158 | 14 |
| 159 | 3946 |
| 160 | 258 |
| 161 | 23 |
| 162 | 14 |
| 163 | 15 |
| 164 | 9 |
| 165 | 28 |
| 166 | 3901 |
| 173 | 46 |
| 174 | 282 |
| 176 | 229 |
| 177 | 151 |
| 181 | 221 |
| 195 | 1405 |

Experimental Example 3

Assay for Analgesic Effect

A PBQ-induced writhing test was conducted in mice to assay for the analgesic effect of the novel compounds. Five-week-old ICR male mice were treated with PBQ (phenyl-p-quinone, 0.02%). A suspension of 20 mg of test material in 10 mL of physiological saline was used per kg of weight of mice. Test materials in combination with a carrier were orally administered one hour before the intraabdominal injection of PBQ in a dose of 10 mL per kg weight. From 5 min after the injection, individual mice in each test group were measured for numbers of writhes at regular intervals of 10 min. Analgesic effects of test compounds were expressed as percentages of the decrease in number of writhes compared to a control.

[% Inhibition=(Control administered with carrier alone−Group administered with test material)/ control administered with carrier alone×100]

TABLE 4

Analgesic Effects of Test Compounds

| Cpds. | % Inhibition |
|---|---|
| 1 | 33 |
| 3 | 58 |
| 6 | 33 |
| 12 | 35 |
| 25 | 23 |
| 29 | 41 |
| 31 | 35 |
| 33 | 31 |
| 36 | 70 |
| 37 | 50 |
| 67 | 23 |
| 105 | 50 |
| 107 | 46 |
| 138 | 22 |
| 139 | 26 |
| 158 | 53 |
| 162 | 28 |
| 163 | 41 |
| 164 | 53 |
| 165 | 60 |
| 167 | 55 |
| 169 | 57 |

Experimental Test 4

Toxicity Test

The novel compounds were assayed for acute oral toxicity in mice.

To four groups of 10 ICR lineage male mice, the compounds of the present invention, 2-[4-(3-chloropyridin-2-yl)-phenyl]-6-trifluoromethyl-1H-benzoimidazole (1), 6-tert-butyl-2-[4-(3-chloropyridin-2-yl)phenyl]-1H-benzoimidazole (3), N-[4'-(4,6-bistrifluoromethyl-1H-benzoimidazole-2-yl)-3-fluorobiphenyl-4-yl]methanesulfonamide (29), 4-bromo-6-(trifluoromethyl)-2-(4-(3-(trifluoromethyl)pyridin-2-yl)phenyl)-1H-benzoimidazole (36), 6-tert-butyl-2-[4-(3-chloropyridin-2-yl)naphthalen-1-yl]-1H-benzoimidazole (105), 3-trifluoromethyl-6'-(6-trifluoromethyl-1H-benzoimidazole-2-yl)-[2,3']bipyridine (158), 6-bromo-2-(5-(3-(trifluoromethyl)pyridin-2-yl)pyridin-2-yl)-1H-benzoimidazole (165) and 6'-(6-morpholin-4-yl-1H-benzoimidazole-2-yl)-3-trifluoromethyl-[2,3']bipyridine (169) were orally administered at doses of zero mg/kg for control, and 125, 250 and 500 mg/kg for test groups, and observations were made of the death, clinical symptoms, and weight changes, and microscopic diagnosis of the animals for 14 days.

None of the mice to which the compounds of interest were administered died or differed from the control with respect to clinical symptoms, weight change, and microscopic diagnosis, indicating that the compounds of the present invention are safe.

INDUSTRIAL APPLICABILITY

As described hereinbefore, the compounds of the present invention are useful in the prevention and treatment of pain, acute pain, chronic pain, neuropathic pain, postoperative pain, migraines, arthralgia, neuropathy, nerve injury, diabetic neuropathy, neurological illness, neurodermatitis, strokes, bladder hypersensitivity, irritable bowel syndrome, respiratory disorders such as asthma, chronic obstructive pulmonary disease, etc., burns, psoriasis, itching, vomiting, irritation of the skin, eyes, and mucous membranes, gastric-duodenal ulcers, inflammatory intestinal diseases, and inflammatory diseases.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:

1. A compound having the following Chemical Formula 1, or a pharmaceutically acceptable salt thereof:

Chemical Formula 1

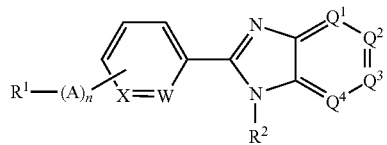

wherein:
$R^1$ is 3-methylpyridin-2-yl, unsubstituted pyridinyl, pyridinyl substituted with one or more $R^a$, or phenyl substituted with a fluoro and a methanesulfonamide group;
each $R^a$ is independently selected from a non-substituted lower alkenyl having 2 to 6 carbon atoms; a non-substituted lower alkoxy having 1 to 8 carbon atoms; a non-substituted haloalkyl having 1 to 6 carbon atoms; a non-substituted haloalkoxy having 1 to 6 carbon atoms; a halogen atom; a nitro; a hydroxyl; a cyano; an amino, an amide and a sulfonamide group, wherein the amino, amide and sulfonamide groups are mono- or di-substituted with a non-substituted alkyl having 1 to 6 carbon atoms or are non-substituted;
A is O or CO;
n is an integer equal to 0 or 1;
W is N or $CR^3$;
X is N or $CR^4$;
$R^2$ is hydrogen;
$R^3$ and $R^4$ may be the same or different, and are each independently hydrogen; or a halogen atom;
$Q_1$ is N or $CR^6$;
$Q_2$ is $CR^7$;
$Q_3$ is $CR^8$;
$Q_4$ is N or $CR^9$;
$R^6$ is hydrogen; a non-substituted lower alkyl having 1 to 8 carbon atoms; a non-substituted lower alkoxy having 1 to 8 carbon atoms; a non-substituted haloalkyl having 1 to 6 carbon atoms; a non-substituted haloalkoxy having 1 to 6 carbon atoms; a halogen atom; an amino which is mono- or di-substituted with a non-substituted lower alkyl having 1 to 6 carbon atoms or is non-substituted; a cyclic group selected from the group consisting of morpholine, thiomorpholine and pyrrolidine;
$R^9$ is hydrogen; a non-substituted lower alkyl having 1 to 8 carbon atoms; a non-substituted lower alkoxy having 1 to 8 carbon atoms; a non-substituted haloalkyl having 1 to 6 carbon atoms; a non-substituted haloalkoxy having 1 to 6 carbon atoms; a halogen atom; an amino which is mono- or di-substituted with a non-substituted lower alkyl having 1 to 6 carbon atoms; a cyclic group selected from the group consisting of morpholine, thiomorpholine and pyrrolidine;
$R^7$ is hydrogen, or a halogen atom;
$R^8$ is hydrogen; a non-substituted lower alkyl having 1 to 8 carbon atoms; a non-substituted lower alkenyl having 2 to 6 carbon atoms; a non-substituted lower alkoxy having 1 to 8 carbon atoms; a non-substituted haloalkyl having 1 to 6 carbon atoms; a non-substituted haloalkoxy having 1 to 6 carbon atoms; a halogen atom; hydroxy; hydroxymethyl; an amino which is mono- or di-substituted with a non-substituted lower alkyl having 1 to 6 carbon atoms; sulfanyl; a cyclic group selected from the group consisting of pyridine, pyrimidine, pyrazole, phenyl, benzyl, imidazole, morpholine, benzodioxole, benzothiazole, indole, pyrazolone, thiophene, thiazole, isothiazole, oxazole, isooxazole, triazole, oxodiazole, thiadiazole, indazole, thiomorpholine, thiazolidine, oxazolidine, pyrrolidine, chromonyl, piperidine, morpholineethyl, and dihydropyrazole, wherein the cyclic group is non-substituted or substituted with one or more $R^d$; and
each $R^d$ is independently selected from a non-substituted lower alkyl having 1 to 8 carbon atoms; a non-substituted lower alkenyl having 2 to 6 carbon atoms; a non-substituted lower alkoxy having 1 to 8 carbon atoms; a non-substituted haloalkyl having 1 to 6 carbon atoms; a non-substituted haloalkoxy having 1 to 6 carbon atoms; a halogen atom; a nitro; a hydroxyl; a cyano; an amino, amide, sulfanyl, and a carboxylic acid which is mono- or di-substituted with a non-substituted lower alkyl having 1 to 6 carbon atoms or is non-substituted.

2. A compound or the pharmaceutically acceptable salt thereof selected from the group consisting of 2-[4-(3-chloropyridin-2-yl)phenyl]-6-trifluoromethyl-1H-benzoimidazole,
6-chloro-2-[4-(3-chloropyridin-2-yl)phenyl]-1H-benzoimidazole,
6-tert-butyl-2-[4-(3-chloropyridin-2-yl)phenyl]-1H-benzoimidazole,
2-[4-(3-chloropyridin-2-yl)phenyl]-6-fluoro-1H-benzoimidazole,
2-[4-(3-chloropyridin-2-yl)phenyl]-6-methoxy-1H-benzoimidazole,
4-chloro-2-[4-(3-chloropyridin-2-yl)phenyl]-6-trifluoromethyl-1H-benzoimidazole,
2-[4-(3-chloropyridin-2-yl)phenyl]-4,6-bistrifluoromethyl-1H-benzoimidazole,
2-[4-(3-chloropyridin-2-yl)phenyl]-6-trifluoromethyl-1H-imidazo[4,5-b]pyridine,
2-[4-(3-chloropyridin-2-yl)phenyl]-3H-imidazo[4,5-b]pyridine,
2-[4-(3-chloropyridin-2-yl)phenyl]-6,7-dimethyl-1H-benzoimidazole,
2-[4-(3-chloropyridin-2-yl)phenyl]-1H-benzoimidazole,
2-[4-(3-chloropyridin-2-yl)phenyl]-5,6-dichloro-1H-benzoimidazole,
6-bromo-2-(4-(3-chloropyridin-2-yl)phenyl)-1H-benzoimidazole,
4-bromo-2-(4-(3-chloropyridin-2-yl)phenyl)-6-(trifluoromethyl)-1H-benzoimidazole,
6-bromo-2-(4-(3-chloropyridin-2-yl)phenyl)-1H-imidazo[4,5-b]pyridine,
4,6-dibromo-2-[4-(3-chloropyridin-2-yl)phenyl]-1H-benzoimidazole,
2-[4-(3-chloropyridin-2-yl)phenyl]-6-morpholin-4-yl-1H-benzoimidazole,
2-[4-(3-chloropyridin-2-yl)phenyl]-6-thiomorpholin-4-yl-1H-benzoimidazole,
2-[4-(3-chloropyridin-2-yl)phenyl]-4-morpholin-4-yl-6-trifluoromethyl-1H-benzoimidazole,
2-[4-(3-chloropyridin-2-yl)phenyl]-4-thiomorpholin-4-yl-6-trifluoromethyl-1H-benzoimidazole,
2-[4-(3-chloropyridin-2-yl)phenyl]-4-pyrrolidin-1-yl-6-trifluoromethyl-1H-benzoimidazole,
{2-[4-(3-chloropyridin-2-yl)phenyl]-6-trifluoromethyl-1H-benzoimidazole-4-yl}diethylamine,
2-[4-(3-chloropyridin-2-yl)phenyl]-6-morpholin-4-yl-1H-imidazo[4,5-b]pyridine,
2-[4-(3-chloropyridin-2-yl)phenyl]-6-pyrrolidin-1-yl-1H-imidazo[4,5-b]pyridine,
6-tert-butyl-2-[4-(3,5-dichloropyridin-2-yl)phenyl]-1H-benzoimidazole,
2-[4-(3,5-dichloropyridin-2-yl)phenyl]-4,6-bistrifluoromethyl-1H-benzoimidazole,
6-tert-butyl-2-[4-(3-chloro-5-trifluoromethylpyridin-2-yl)phenyl]-1H-benzoimidazole,
2-[4-(3-chloro-5-trifluoromethylpyridin-2-yl)phenyl]-4,6-bistrifluoromethyl-1H-benzoimidazole,
2-[4-(3-chloro-5-trifluoromethylpyridin-2-yl)phenyl]-5,7-bistrifluoromethyl-1H-benzoimidazole,
N-[4'-(4,6-bistrifluoromethyl-1H-benzoimidazole-2-yl)-3-fluorobiphenyl-4-yl]methanesulfonamide,
6-tert-butyl-2-[4-(3-trifluoromethylpyridin-2-yl)phenyl]-1H-benzoimidazole,
4-chloro-6-trifluoromethyl-2-[4-(3-trifluoromethylpyridin-2-yl)phenyl]-1H-benzoimidazole,
6-chloro-2-[4-(3-trifluoromethylpyridin-2-yl)phenyl]-1H-benzoimidazole,
4,6-bistrifluoromethyl-2-[4-(3-trifluoromethylpyridin-2-yl)phenyl]-1H-benzoimidazole,
6-trifluoromethyl-2-[4-(3-trifluoromethylpyridin-2-yl)phenyl]-1H-imidazo[4,5-b]pyridine,
5,6-dichloro-2-[4-(3-trifluoromethylpyridin-2-yl)phenyl]-1H-benzoimidazole,
4-bromo-6-(trifluoromethyl)-2-(4-(3-(trifluoromethyl)pyridin-2-yl)phenyl)-1H-benzoimidazole,
6-bromo-2-(4-(3-(trifluoromethyl)pyridin-2-yl)phenyl)-1H-benzoimidazole,
6-fluoro-2-(4-(3-(trifluoromethyl)pyridin-2-yl)phenyl)-1H-benzoimidazole,
6-bromo-2-(4-(3-(trifluoromethyl)pyridin-2-yl)phenyl)-1H-imidazo[4,5-b]pyridine,
4,6-dibromo-2-[4-(3-trifluoromethylpyridin-2-yl)phenyl]-1H-benzoimidazole,
6-morpholin-4-yl-2-[4-(3-trifluoromethylpyridin-2-yl)phenyl]-1H-benzoimidazole,
6-thiomorpholin-4-yl-2-[4-(3-trifluoromethylpyridin-2-yl)phenyl]-1H-benzoimidazole,
diethyl-{2-[4-(3-trifluoromethylpyridin-2-yl)phenyl]-3H-benzoimidazo-5-yl}amine,
4-morpholin-4-yl-6-trifluoromethyl-2-[4-(3-trifluoromethylpyridin-2-yl)phenyl]-1H-benzoimidazole,
4-thiomorpholin-4-yl-6-trifluoromethyl-2-[4-(3-trifluoromethylpyridin-2-yl)phenyl]-1H-benzoimidazole,
4-pyrrolidin-1-yl-6-trifluoromethyl-2-[4-(3-trifluoromethylpyridin-2-yl)phenyl]-1H-benzoimidazole,
6-tert-butyl-2-(4-pyridin-2-ylphenyl)-1H-benzoimidazole,
6-(trifluoromethyl)-2-(4-(pyridin-2-yl)phenyl)-1H-benzoimidazole,
4-chloro-6-(trifluoromethyl)-2-(4-(pyridin-2-yl)phenyl)-1H-benzoimidazole,
5,6-dichloro-2-(4-(pyridin-2-yl)phenyl)-1H-benzoimidazole,
4,6-bis(trifluoromethyl)-2-(4-(pyridin-2-yl)phenyl)-1H-benzoimidazole,
6-fluoro-2-(4-(pyridin-2-yl)phenyl)-1H-benzoimidazole,
6-bromo-2-(4-(pyridin-2-yl)phenyl)-1H-imidazo[4,5-b]pyridine,
4,6-dibromo-2-(4-pyridin-2-ylphenyl)-1H-benzoimidazole,
2-(4-(6-(trifluoromethyl)-1H-benzoimidazole-2-yl)phenyl)pyridin-3-carbonitrile,
2-(4-(6-(tert-butyl)-1H-benzoimidazole-2-yl)phenyl)pyridin-3-carbonitrile,
6'-(4,6-dibromo-1H-benzoimidazole-2-yl)-[2,3']bipyridyl-3-carbonitrile,
6-tert-butyl-2-[4-(3-chloropyridin-2-yl)-2-fluorophenyl]-1H-benzoimidazole,
4-chloro-2-[4-(3-chloropyridin-2-yl)-2-fluorophenyl]-6-trifluoromethyl-1H-benzoimidazole,
2-[4-(3-chloropyridin-2-yl)-2-fluorophenyl]-6-methoxy-1H-benzoimidazole,
6-tert-butyl-2-[4-(3,5-dichloropyridin-2-yl)-2-fluorophenyl]-1H-benzoimidazole,
4-chloro-2-[4-(3,5-dichloropyridin-2-yl)-2-fluorophenyl]-6-trifluoromethyl-1H-benzoimidazole,
2-[4-(3,5-dichloropyridin-2-yl)-2-fluorophenyl]-4,6-bistrifluoromethyl-1H-benzoimidazole, 4-chloro-2-[4-(3-chloro-5-trifluoromethylpyridin-2-yl)-2-fluorophenyl]-6-trifluoromethyl-1H-benzoimidazole,
2-[4-(3-chloro-5-trifluoromethylpyridin-2-yl)-2-fluorophenyl]-6-trifluoromethyl-1H-imidazo[4,5-b]pyridine,
2-[4-(3-chloro-5-trifluoromethylpyridin-2-yl)-2-fluorophenyl]-6-methoxy-1H-benzoimidazole,
N-[3,3'-difluoro-4'-(6-methoxy-1H-benzoimidazole-2-yl)biphenyl-4-yl]methanesulfonamide,
2-[2-fluoro-4-(3-trifluoromethylpyridin-2-yl)phenyl]-6-trifluoromethyl-1H-benzoimidazole,
6-tert-butyl-2-[2-fluoro-4-(3-trifluoromethylpyridin-2-yl)phenyl]-1H-benzoimidazole,
6-chloro-2-[2-fluoro-4-(3-trifluoromethylpyridin-2-yl)phenyl]-1H-benzoimidazole,
5-chloro-2-[2-fluoro-4-(3-trifluoromethylpyridin-2-yl)phenyl]-1H-benzoimidazole,
4-chloro-2-[2-fluoro-4-(3-trifluoromethylpyridin-2-yl)phenyl]-6-trifluoromethyl-1H-benzoimidazole,
7-chloro-2-[2-fluoro-4-(3-trifluoromethylpyridin-2-yl)phenyl]-5-trifluoromethyl-1H-benzoimidazole,
2-(2-fluoro-4-pyridin-2-ylphenyl-6-trifluoromethyl-1H-benzoimidazole,
6-tert-butyl-2-(2-fluoro-4-pyridin-2-ylphenyl)-1H-benzoimidazole,
6-chloro-2-(2-fluoro-4-pyridin-2-yl)phenyl-1H-benzoimidazole,
2-(2-fluoro-4-pyridin-2-yl)phenyl-4,6-bistrifluoromethyl-1H-benzoimidazole,
2-[2-chloro-4-(3-chloropyridin-2-yl)phenyl]-6-trifluoromethyl-1H-benzoimidazole,
4-chloro-2-[2-chloro-4-(3-chloropyridin-2-yl)phenyl]-6-trifluoromethyl-1H-benzoimidazole,
2-[2-chloro-4-(3-chloropyridin-2-yl)phenyl]-6-trifluoromethyl-1H-imidazo[4,5-b]pyridine,
2-[2-chloro-4-(3,5-dichloropyridin-2-yl)phenyl]-6-trifluoromethyl-1H-benzoimidazole,
4-chloro-2-[2-chloro-4-(3,5-dichloropyridin-2-yl)phenyl]-6-trifluoromethyl-1H-benzoimidazole,
2-[2-chloro-4-(3,5-dichloropyridin-2-yl)phenyl]-4,6-bistrifluoromethyl-1H-benzoimidazole,
2-[2-chloro-4-(3,5-dichloropyridin-2-yl)phenyl]-6-trifluoromethyl-1H-imidazo[4,5-b]pyridine,
2-[2-chloro-4-(3-chloro-5-trifluoromethylpyridin-2-yl)phenyl]-6-trifluoromethyl-1H-benzoimidazole,
4-chloro-2-[2-chloro-4-(3-chloro-5-trifluoromethylpyridin-2-yl)phenyl]-6-trifluoromethyl-1H-benzoimidazole,
N-[4'-(6-tert-butyl-1H-benzoimidazole-2-yl)-3'-chloro-3-fluorobiphenyl-4-yl]methanesulfonamide,
N-[3'-chloro-4'-(4-chloro-6-trifluoromethyl-1H-benzoimidazole-2-yl)-3-fluorobiphenyl-4-yl]methanesulfonamide,
N-[4'-(4,6-bistrifluoromethyl-1H-benzoimidazole-2-yl)-3'-chloro-3-fluorobiphenyl-4-yl]methanesulfonamide,
2-[2-chloro-4-(3-trifluoromethylpyridin-2-yl)phenyl]-6-trifluoromethyl-1H-benzoimidazole,
4-chloro-2-[2-chloro-4-(3-trifluoromethylpyridin-2-yl)phenyl]-6-trifluoromethyl-1H-benzoimidazole,
2-[2-chloro-4-(3-trifluoromethylpyridin-2-yl)phenyl]-4,6-bistrifluoromethyl-1H-benzoimidazole,
6-tert-butyl-2-[2-chloro-4-(3-methylpyridin-2-yl)phenyl]-1H-benzoimidazole,
6-chloro-2-(2-chloro-4-pyridin-2-ylphenyl)-1H-benzoimidazole,
2-(2-chloro-4-pyridin-2-ylphenyl)-6-trifluoromethyl-1H-imidazo[4,5-b]pyridine,
2-(2-chloro-4-pyridin-2-ylphenyl)-6-methoxy-1H-benzoimidazole,
6-tert-butyl-2-[3-chloro-4-(3-chloropyridin-2-yl)phenyl]-1H-benzoimidazole,
2-[3-chloro-4-(3,5-dichloropyridin-2-yl)phenyl]-6-trifluoromethyl-1H-benzoimidazole,
6-tert-butyl-2-[3-chloro-4-(3,5-dichloropyridin-2-yl)phenyl]-1H-benzoimidazole,
2-[3-chloro-4-(3,5-dichloropyridin-2-yl)phenyl]-6-methoxy-1H-benzoimidazole,
2-[3-chloro-4-(3,5-dichloropyridin-2-yl)phenyl]-5-methoxy-1H-benzoimidazole,
2-[3-chloro-4-(3-chloro-5-trifluoromethylpyridin-2-yl)phenyl]-6-trifluoromethyl-1H-benzoimidazole,
6-tert-butyl-2-[3-chloro-4-(3-chloro-5-trifluoromethylpyridin-2-yl)phenyl]-1H-benzoimidazole,
2-[3-chloro-4-(3-chloro-5-trifluoromethylpyridin-2-yl)phenyl]-6-methoxy-1H-benzoimidazole,
2-[3-chloro-4-(3-chloro-5-trifluoromethylpyridin-2-yl)phenyl]-5-methoxy-1H-benzoimidazole,
N-[2'-chloro-4'-(4-chloro-6-trifluoromethyl-1H-benzoimidazole-2-yl)-3-fluorobiphenyl-4-yl]methanesulfonamide,
N-[4'-(4,6-bistrifluoromethyl-1H-benzoimidazole-2-yl)-2'-chloro-3-fluorobiphenyl-4-yl]methanesulfonamide,
2-(3-chloro-4-pyridin-2-ylphenyl)-6-trifluoromethyl-1H-benzoimidazole,
6-tert-butyl-2-(3-chloro-4-pyridin-2-ylphenyl)-1H-benzoimidazole,
6-chloro-2-(3-chloro-4-pyridin-2-ylphenyl)-1H-benzoimidazole,
4-chloro-2-(3-chloro-4-pyridin-2-ylphenyl)-6-trifluoromethyl-1H-benzoimidazole,
5,6-dichloro-2-(3-chloro-4-(pyridin-2-yl)phenyl)-1H-benzoimidazole,
6-bromo-2-(3-chloro-4-(pyridin-2-yl)phenyl)-1H-benzoimidazole,
2-[3-chloro-4-(3-trifluoromethylpyridin-2-yl)phenyl]-6-trifluoromethyl-1H-benzoimidazole,
6-tert-butyl-2-[3-chloro-4-(3-trifluoromethylpyridin-2-yl)phenyl]-1H-benzoimidazole,
6-chloro-2-[3-chloro-4-(3-trifluoromethylpyridin-2-yl)phenyl]-1H-benzoimidazole,
2-[3-chloro-4-(3-trifluoromethylpyridin-2-yl)phenyl]-6-methoxy-1H-benzoimidazole,
2-[3-chloro-4-(3-methylpyridin-2-yl)phenyl]-6-trifluoromethyl-1H-benzoimidazole,
3-chloro-6'-(6-trifluoromethyl-1H-benzoimidazole-2-yl)-[2,3']bipyridine,
3-chloro-6'-(6-chloro-1H-benzoimidazole-2-yl)-[2,3']bipyridine,
3-chloro-6'-(4-chloro-6-trifluoromethyl-1H-benzoimidazole-2-yl)-[2,3']bipyridine,
6'-(4,6-bistrifluoromethyl-1H-benzoimidazole-2-yl)-3-chloro-[2,3']bipyridine,
4-bromo-2-(5-(3-chloropyridin-2-yl)pyridin-2-yl)-6-(trifluoromethyl)-1H-benzoimidazole,
6-bromo-2-(5-(3-chloropyridin-2-yl)pyridin-2-yl)-1H-benzoimidazole,
6'-(6-tert-butyl-1H-benzoimidazole-2-yl)-3-chloro-[2,3']bipyridine,
3-chloro-6'-(5,6-dichloro-1H-benzoimidazole-2-yl)-[2,3']bipyridine,
3-chloro-6'-(4,6-dibromo-1H-benzoimidazole-2-yl)-[2,3']bipyridine,
6'-(6-bromo-1H-imidazo[4,5-b]pyridine-2-yl)-3-chloro-[2,3']bipyridine, 3-chloro-6'-(6-morpholin-4-yl-1H-benzoimidazole-2-yl)-[2,3']bipyridine,
3-chloro-6'-(6-thiomorpholin-4-yl-1H-benzoimidazole-2-yl)-[2,3']bipyridine,
3-chloro-6'-(4-morpholin-4-yl-6-trifluoromethyl-1H-benzoimidazole-2-yl)-[2,3']bipyridine,
3-chloro-6'-(4-thiomorpholin-4-yl-6-trifluoromethyl-1H-benzoimidazole-2-yl)-[2,3']bipyridine,
3-chloro-6'-(4-pyrrolidin-1-yl-6-trifluoromethyl-1H-benzoimidazole-2-yl)-[2,3']bipyridine,
3,5-dichloro-6'-(6-trifluoromethyl-1H-benzoimidazole-2-yl)-[2,3']bipyridine,
6'-(6-tert-butyl-1H-benzoimidazole-2-yl)-3,5-dichloro-[2,3']bipyridine,
3,5-dichloro-6'-(6-chloro-1H-benzoimidazole-2-yl)-[2,3']bipyridine,
3,5-dichloro-6'-(4-chloro-6-trifluoromethyl-1H-benzoimidazole-2-yl)-[2,3']bipyridine,
6'-(4,6-bistrifluoromethyl-1H-benzoimidazole-2-yl)-3,5-dichloro-[2,3']bipyridine,
6'-(4,6-bistrifluoromethyl-1H-benzoimidazole-2-yl)-3-chloro-5-trifluoromethyl-[2,3']bipyridine,
6'-(6-methoxy-1H-benzoimidazole-2-yl)-3-chloro-5-trifluoromethyl-[2,3']bipyridine,
3-trifluoromethyl-6'-(6-trifluoromethyl-1H-benzoimidazole-2-yl)-[2,3']bipyridine,
6'-(6-tert-butyl-1H-benzoimidazole-2-yl)-3-trifluoromethyl-[2,3']bipyridine,
6'-(6-chloro-1H-benzoimidazole-2-yl)-3-trifluoromethyl-[2,3']bipyridine,
6'-(4-chloro-6-trifluoromethyl-1H-benzoimidazole-2-yl)-3-trifluoromethyl-[2,3']bipyridine,
6'-(5-trifluoromethyl-7-chloro-1H-benzoimidazole-2-yl)-3-trifluoromethyl-[2,3']bipyridine,
6'-(4,6-bistrifluoromethyl-1H-benzoimidazole-2-yl)-3-trifluoromethyl-[2,3']bipyridine,
6'-(5,6-dichloro-1H-benzoimidazole-2-yl)-3-trifluoromethyl-[2,3']bipyridine,
4-bromo-6-(trifluoromethyl)-2-(5-(3-(trifluoromethyl)pyridin-2-yl)pyridin-2-yl)-1H-benzoimidazole,
6-bromo-2-(5-(3-(trifluoromethyl)pyridin-2-yl)pyridin-2-yl)-1H-benzoimidazole,
6-fluoro-2-(5-(3-(trifluoromethyl)pyridin-2-yl)pyridin-2-yl)-1H-benzoimidazole,
6'-(6-bromo-1H-imidazo[4,5-b]pyridine-2-yl)-3-trifluoromethyl[2,3']bipyridine,
6'-(4,6-dibromo-1H-benzoimidazole-2-yl)-3-trifluoromethyl-[2,3']bipyridine,
6'-(6-morpholin-4-yl-1H-benzoimidazo-2-yl)-3-trifluoromethyl-[2,3']bipyridine,
6'-(4-morpholin-4-yl-6-trifluoromethyl-1H-benzoimidazole-2-yl)-3-trifluoromethyl-[2,3']bipyridine,
6'-(6-chloro-1H-benzoimidazole-2-yl)-[2,3']bipyridine,
6'-(6-trifluoromethyl-1H-imidazo[4,5-b]pyridine-2-yl)-[2,3']bipyridine,
5,6-dichloro-2-(5-(pyridin-2-yl)pyridin-2-yl)-1H-benzoimidazole,
2-[4-(3-chloropyridin-2-yl)phenyl]-6-trifluoromethyl-1H-benzoimidazole hydrochloride,
6-tert-butyl-2-[4-(3-chloropyridin-2-yl)phenyl]-1H-benzoimidazole hydrochloride,
6-tert-butyl-2-[4-(3-chloropyridin-2-yl)naphthalen-1-yl]-1H-benzoimidazole hydrochloride,
6'-(4,6-bistrifluoromethyl-1H-benzoimidazole-2-yl)-3-chloro[2,3']bipyridine hydrochloride,
3-trifluoromethyl-6'-(6-trifluoromethyl-1H-benzoimidazole-2-yl)-[2,3']bipyridine hydrochloride,
6-tert-butyl-2-[4-(3-chloropyridin-2-yl)phenyl]-1H-benzoimidazole sodium salt,
3-trifluoromethyl-6'-(6-trifluoromethyl-1H-benzoimidazole-2-yl)-[2,3']bipyridine sulfate,
3-trifluoromethyl-6'-(6-trifluoromethyl-1H-benzoimidazole-2-yl)-[2,3']bipyridine phosphate,
3-trifluoromethyl-6'-(6-trifluoromethyl-1H-benzoimidazole-2-yl)-[2,3']bipyridine methansulfonate, and
3-trifluoromethyl-6'-(6-trifluoromethyl-1H-benzoimidazole-2-yl)-[2,3']bipyridine benzenesulfonate.

3. A pharmaceutical composition, comprising the compound of claim 1, or a pharmaceutically acceptable salt thereof, and a pharmaceutically acceptable carrier.

4. The compound, or the pharmaceutically acceptable salt thereof, of claim 1, wherein:
$R^1$ is 3 methylpyridin-2-yl, unsubstituted pyridinyl or pyridinyl substituted with one or more $R^a$, or phenyl substituted with a fluoro and a methanesulfonamide group; wherein each $R^a$ is independently selected from a haloalkyl having 1 to 6 carbon atoms; a halogen atom; a cyano; and a sulfonamide group, wherein the sulfonamide group is mono- or di-substituted with a non-substituted alkyl having 1 to 6 carbon atoms or is non-substituted;
A is O or CO;
n is an integer equal to 0 or 1;
W is N or $CR^3$;
X is N or $CR^4$;
$R^2$ is hydrogen;
$R^3$ and $R^4$ may be the same or different, and are each independently hydrogen; or a halogen atom;
$Q_1$ is N or $CR^6$;
$Q_2$ is $CR^7$;
$Q_3$ is $CR^8$;
$Q_4$ is N or $CR^9$;
$R^7$ is hydrogen, or a halogen atom;
$R^6$, $R^8$, and $R^9$ are the same or different, and are each independently hydrogen; a non-substituted lower alkyl having 1 to 8 carbon atoms; a non-substituted lower alkoxy having 1 to 8 carbon atoms; a non-substituted haloalkyl having 1 to 6 carbon atoms; a halogen atom; an amino group; morpholine; thiomorpholine or a pyrrolidine group, wherein the amino group is mono- or di-substituted with a lower alkyl having 1 to 6 carbon atoms.

5. The compound, or the pharmaceutically acceptable salt thereof, of claim 1, wherein:
$R^1$ is 3-methylpyridin-2-yl, unsubstituted pyridine, pyridine substituted with one or more $R^a$, or phenyl substituted with a fluoro and a methanesulfonamide group; wherein each $R^a$ is independently selected from trifluoromethyl; Cl; F, a cyano; and methanesulfonamide;
A is O or CO;
n is an integer equal to 0 or 1;
W is N or $CR^3$;
X is N or $CR^4$;
$R^2$ is hydrogen;
$R^3$ and $R^4$ may be the same or different, and are each independently hydrogen; F; or Cl;
$Q_1$ is N or $CR^6$;
$Q_2$ is $CR^7$;
$Q_3$ is $CR^8$;
$Q_4$ is N or $CR^9$;
$R^7$ is hydrogen, F, Cl or Br;
$R^6$, $R^8$, and $R^9$ may be the same or different, and are each independently hydrogen;

methyl; 2-butyl; tert-butyl; methoxy; trifluoromethyl; F; Cl; Br; diethylamino; morpholine, thiomorpholine or a pyrrolidine group.

6. A pharmaceutical composition, comprising a compound of claim 2, or a pharmaceutically acceptable salt thereof, and a pharmaceutically acceptable carrier.

7. A method for treating pain comprising administering to a person in need thereof a pharmaceutical composition comprising the compound of Chemical Formula 1 of claim 1, or a pharmaceutical acceptable salt thereof.

8. A method for treating pain comprising administering to a person in need thereof a pharmaceutical composition comprising the compound of claim 2, or a pharmaceutical acceptable salt thereof.

9. The method according to claim 7, wherein the pain is acute pain, chronic pain, neuropathic pain, postoperative pain, migraines, arthralgia, or a combination thereof.

10. The method according to claim 8, wherein the pain is acute pain, chronic pain, neuropathic pain, postoperative pain, migraines, arthralgia, or a combination thereof.

* * * * *